United States Patent
Jakobovits et al.

(10) Patent No.: US 12,221,480 B2
(45) Date of Patent: Feb. 11, 2025

(54) METHODS FOR SELECTIVE EXPANSION OF DELTA-3 GAMMA DELTA T-CELL POPULATIONS AND COMPOSITIONS THEREOF

(71) Applicant: ADICET THERAPEUTICS, INC., Redwood City, CA (US)

(72) Inventors: Aya Jakobovits, Beverly Hills, CA (US); Daulet Kadyl Satpayev, Redwood City, CA (US); Orit Foord, Foster City, CA (US); Yifeng Frank Jing, Hayward, CA (US); Hui Shao, Foster City, CA (US); Jason Michael Romero, East Palo Alto, CA (US); Mary Michael Brody, Menlo Park, CA (US); Matthew Ian Hoopes, Menlo Park, CA (US)

(73) Assignee: ADICET THERAPEUTICS, INC.

( * ) Notice: Subject to any disclaimer, the term of this patent is extended or adjusted under 35 U.S.C. 154(b) by 1174 days.

(21) Appl. No.: 16/764,796

(22) PCT Filed: Nov. 15, 2018

(86) PCT No.: PCT/US2018/061384
§ 371 (c)(1),
(2) Date: May 15, 2020

(87) PCT Pub. No.: WO2019/099744
PCT Pub. Date: May 23, 2019

(65) Prior Publication Data
US 2023/0257462 A1  Aug. 17, 2023

Related U.S. Application Data

(60) Provisional application No. 62/586,782, filed on Nov. 15, 2017.

(51) Int. Cl.
*C07K 16/28* (2006.01)
*A61K 39/00* (2006.01)
*C12N 5/0783* (2010.01)

(52) U.S. Cl.
CPC ...... *C07K 16/2809* (2013.01); *A61K 39/4611* (2023.05); *A61K 39/4631* (2023.05); *A61K 39/464424* (2023.05); *C12N 5/0636* (2013.01); *C07K 2317/92* (2013.01); *C12N 2510/00* (2013.01)

(58) Field of Classification Search
CPC ............ C07K 16/2809; C07K 2317/92; C12N 5/0636; C12N 2510/00
See application file for complete search history.

(56) References Cited

U.S. PATENT DOCUMENTS

| | | |
|---|---|---|
| 5,185,250 A | 2/1993 | Brenner et al. |
| 5,260,223 A | 11/1993 | Brenner et al. |
| 7,728,114 B2 | 6/2010 | Mach et al. |
| 7,985,739 B2 | 7/2011 | Kay et al. |
| 9,540,448 B2 | 1/2017 | Scheinberg et al. |
| 2003/0138433 A1 | 7/2003 | Newell et al. |
| 2006/0026986 A1 | 1/2006 | Wang et al. |
| 2006/0122130 A1 | 6/2006 | Rabbani |
| 2006/0205089 A1 | 9/2006 | Dratz et al. |
| 2008/0026986 A1 | 1/2008 | Wang et al. |
| 2008/0171014 A1 | 7/2008 | Wu et al. |
| 2010/0272739 A1 | 10/2010 | Gelfand et al. |
| 2012/0034221 A1 | 2/2012 | Bonvini et al. |
| 2014/0141513 A1 | 5/2014 | De Carvalho Silva Santos et al. |
| 2015/0259645 A1 | 9/2015 | Poupot et al. |
| 2018/0169147 A1 | 6/2018 | Anjos et al. |

FOREIGN PATENT DOCUMENTS

| | | |
|---|---|---|
| CN | 1506456 A | 6/2004 |
| CN | 102994448 A | 3/2013 |
| WO | WO 1993/020221 A1 | 10/1993 |
| WO | WO 2001/022816 A1 | 4/2001 |
| WO | WO 2003/087341 A2 | 10/2003 |
| WO | WO 2011/090804 A1 | 7/2011 |
| WO | WO 2012/012667 A2 | 1/2012 |
| WO | WO 2012/156958 A2 | 11/2012 |
| WO | WO 2013/074916 A1 | 5/2013 |
| WO | WO 2013/079174 A1 | 6/2013 |
| WO | WO 2014/009370 A2 | 1/2014 |
| WO | WO 2014/134412 A1 | 9/2014 |
| WO | WO 2015/061694 A2 | 4/2015 |
| WO | WO 2015/156673 A2 | 10/2015 |
| WO | WO 2016/081518 A2 | 5/2016 |
| WO | WO 2016/198480 A1 | 12/2016 |

(Continued)

OTHER PUBLICATIONS

Romagné et al. (Journal of Immunological Methods. 189(1):25-36 (1996)) (Year: 1996).*
Zhao et al. J Transl Med16(3):1-13. (2018) (Year: 2018).*
Zhou et al. Cell Mol. Immunol. 9:34-44 (2012) (Year: 2012).*
Almagro & Fransson, Frontiers in Bioscience 2008; 13:1619-33 (Year: 2018).*
Chiu et al., Antibodies, 8(55):1-80. (2019) (Year: 2019).*
Lobner et al., Immunol Rev 270:113-131 (2016) (Year: 2016).*

(Continued)

*Primary Examiner* — Jessica H Roark
*Assistant Examiner* — Francesca Edgington Giordano
(74) *Attorney, Agent, or Firm* — Todd Lorenz

(57) ABSTRACT

The present application is directed to agents that bind an epitope specific to a δ3 γδ TCR. Such agents can be, but are not limited to, an antibody or fragment thereof. Also described herein are methods for using the agents, e.g., to expand or selectively expand δ3 γδ T cells. Also described herein are methods of using expanded δ3 γδ T cells for treatment of a subject in need thereof.

28 Claims, 19 Drawing Sheets

Specification includes a Sequence Listing.

(56) References Cited

FOREIGN PATENT DOCUMENTS

| WO | WO 2017/011804 A1 | 1/2017 |
|----|-------------------|--------|
| WO | WO 2017/197347 A1 | 11/2017 |

OTHER PUBLICATIONS

Ali et al., "γδ T Cell Immune Manipulatino during Chroinic Phase of Simian HIV Infection Confers Immunological Benefits", J. Immunol., vol. 183, No. 8, pp. 5407-5417 (2009).
Appay et al, "Memory CD8+ T cells vary in differentiation phenotype in different persistent virus infections," Nature Medicine, vol. 8, pp. 379-385 (2002).
Bauer et al, Gene Therapey for HIV: From Inception 49 to a Possible Cure, SpringBriefs in Biochemistry and Molecular Biology, Chapter 7, pp. 49-54 (2014).
Biocompare, "Monoclonal Antibody Anti-Human TCR PAN [gamma]/[delta] PN IM1349—Purified—Freeze-dried—0.1 mg—Clone IMMU510 for Research Use Only. Not for use in diagnostic procedures", Beckman Coulter: Jan. 1, 2006, p. 1, left-hand col. paragraph 1, Retrieved from the Internet: at URL:https://www.bc-cytometry.com/PDF/DataSheet/IM1349.pdf [on Apr. 8, 2019].
Bornstein et al, "Development of a new fully human anti-CD20 monoclonal antibody for the treatment of B-cell malignancies," Investigational New Drugs., Vo. 28, Issue 5, pp. 561-574 (2010).
Boucherma et al., "HLA-A 01:03, HLA-A 24-02, HLA-B8:08-01, HLA-B 27:05, HLA-B 35:01, HLA-B 44:02, and HLA-C 07:01 Monochain Transgenic/H-2 Class | Null Mice: Novel Versatile Preclinical Models of Human T Cell Responses," J. Immunol., vol. 191, pp. 583-593 (2013).
Carding and Egan, "γδ TCells: Functional Plasticity and Heterogeneity," Nat Rev Immunol vol. 2, pp. 336-345 (2002).
Cheever et al., "The Prioritization of Cancer Antigens: A National Cancer Institute Pilot Project for the Acceleration of Translational Research,"Clin. Cancer Res., vol. 15(17), pp. 5323-5337 (2009).
Chen et al., "Selection and analysis of an optimized anti-VEGF antibody: crystal structure of an affinity-matured Fab in complex with antigen," J. Mol. Biol. vol. 293, pp. 865-881 (1999).
Chothia and Lesk, "Canonical Structures for the Hypervariable Regions of Immunoglobulins," J. Mol. Biol., vol. 196, pp. 901-917 (1987).
Chothia et al., "Conformations of immunoglobulin hypervariable regions,"Nature, vol. 342, pp. 878-883 (1989).
Ciccone, "A monoclonal antibody specific for a common determinant of the human T cell receptor gamma/delta directly activates CD3+WT31—lymphocytes to express their functional program(s)", The Journal of Experimental Medicine, vol. 168, pp. 1-11 (1988).
Dao et al. "Targeting the intracellular WT1 oncogene product with a therapeutic human antibody" Science translational medicine, vol. 5(176): 176ra33, pp. 1-22 (2013).
Damschroder et al., "Analysis of human and primate CD2 molecules by protein sequence and epitope mapping with anti-human CD2 antibodies," Mol Immunol, vol. 41(10) pp. 985-1000 (2004).
Daubenberger et al., "Functional and Structural Similarity of Vγ9V δ2 T Cells in Humans and Aotus Monkeys, a Primate Infection Model for *Plasmodium falciparum* Malaria," J Immunol, vol. 167, pp. 6421-6430 (2001).
Davis and Merwe, "The structure and ligand interactions of CD2: implications for T-cell function," Immunol. Today, vol. 17, Issue 4, pp. 177-187 (1996).
Deniger et al., "Bispecific T-cells Expressing Polyclonal Repertoire of Endogenous γδ T-cell Receptors and Introduced CD19-specific Chimeric Antigen Receptor," Molecular Therapy, vol. 21, No. 3, pp. 638-647 (2013).
Dohan & Reiter, "T-cell-receptor-like antibodies—generation, function and applications,"Expert Rev Mol Med., vol. 14(e6), pp. 1-17 (2012).
Dokouhaki et al, Adoptive immunotherapy of cancer using ex vivo expanded human γδ T cells: A new approach, Cancer Letters, vol. 297, pp. 126-136 (2010).

Edwards et al, "The Remarkable Flexibility of theHuman Antibody Repertoire; Isolation of Over One Thousand Different Antibodies to a Single Protein, BLyS", J. Mol. Biol., vol. 334, pp. 102-118 (2003).
Ehl et al., "A variant of SCID with specific immune responses and predominance of gamma delta T cells", J. of Clinical Investigation, vol. 115, No. 11, pp. 3140-3148 (2005).
Fisher et al., "Neuroblastoma Killing Properties of Vδ2 and Vδ2-Negative γδT Cells Following Expansion by Artificial Antigen-Presenting Cells," Clinical Cancer Research, vol. 20, No. 22, pp. 5720-5732 (2014).
Gonzalez et al., "Humanized mice: novel model for studying mechanisms of human immune-based therapies," Immunol. Res. vol. 57, pp. 326-334 (2013).
Gra et al., "Analysis of T-Cell Receptor-γ Gene Rearrangements Using Oligonucleotide Microchip: A Novel Approach for the Determination of T-Cell Clonality," Journal of Molecular Diagnostics, vol. 9, No. 2 pp. 249-257 (2007).
Green, et al., "Recognition of nonpeptide antigens by human V gamma 9V delta 2 T cells requires contact with cells of human origin", Clin Exp Immunol., vol. 136(3), pp. 472-482 (2004).
Groh et al., "Broad tumor-associated expression and recognition by tumor-derived gamma delta T cells of MICA and MICB," PNAS, vol. 96, pp. 6879-6884 (1999).
Hamers-Casterman et al., "Naturally occurring antibodies devoid of light chains," Nature, vol. 63, pp. 446-448 (1993).
Harlow et al. Antibodies, A Laboratory Manual, Cold Spring Harbor laboratory, pp. 37-47 (1988).
Hayday A.C., "γδ Cells: A Right Time and Right Place for a Conserved Third Way of Protection," Annu Rev Immunol. vol. 18, pp. 975-1026 (2000).
Hayday and Pennington, "Key factors in the organized chaos of early T cell development," Nature Immunology. vol. 8, No. pp. 137-144 (2007).
Hiasa et al., "Dual specificity of αβ-γδ TCR T cells: transformation of Vγ9Vδ2 T cells with MAGE-A4143-151 specific αβ type TCR genes," Annual Meeting of the Japanese Cancer Association, vol. 66, p. 423 (2007).
Hua et al., "Potentinal regulatory role of in vitro-expanded Vδ1 T cells from human peripheral blood," Immunol Res. vol. 56, pp. 172-180 (2013).
Jakobovits et al., "Production of fully human antibodies by transgenic mice," Curr. Opin. Biotechnol., vol. 6, Issue 5, pp. 561-566 (1995).
Janssens et al., "Generation of heavy-chain-only antibodies in mice," PNAS, vol. 103, No. 41, pp. 15130-15135 (2006).
Jin et al., "Oligoclonal expansion of TCR Vδ T cells may be a potential immune biomarker for clinical outcome of acute myeloid leukemia,"Journal of Hematology & Oncology vol. 9:126, pp. 1-7 (2016).
Kabelitz et al., "The primary response of human gamma/delta+ T cells to Mycobacterium tuberculosis is restricted to Vgamma 9-bearing cells.", The Journal of experimental medicine 173.6, pp. 1331-1338 (1991).
Kabelitz and He, "The Multifunctionality of Human Vγ9Vδ2 γδ T Cells: Clonal Plasticity or Distinct Subsets? : Plasticity of Human γδ T Cells," Scandinavian Journal of Immunology, vol. 76, pp. 213-222 (2012).
Kang et al., "Adoptive immunotherapy of lung cancer with immobilized anti-TCRγδ antibody-expanded human γδ T-cells in peripheral blood," Cancer Biology & Therapy, vol. 8, Issue 16, pp. 1540-1549 (2009).
Kim and Hong, "Humanization by CDR Grafting and Specificity-Determining Residue Grafting," Methods in Molecular Biology, vol. 907, pp. 237-245 (2012).
Klebanoff et al, "CD8+ T-cell memory in tumor immunology and immunotherapy,"Immunol Rev., vol. 211, pp. 214-224 (2006).
Kress et al., Distinct gene expression in human Vδ1 and Vδ2 γδ T cells following non-TCR agonist stimulation, Molecular Immunology, vol. 43, pp. 2002-2011 (2006).
Kondo et al., "Zoledronate facilitates large-scale ex vivo expansion of functional γδ T cells from cancer patients for use in adoptive immunotherapy," Cytotherapy, vol. 10, No. 8, pp. 842-856 (2008).

(56) References Cited

OTHER PUBLICATIONS

Lamb and Lopez, "γδ T cells: A New Frontier for Immunotherapy?," Biology of Blood and Marrow Transplantation, vol. 11, pp. 161-168 (2005).

Lang et al., "Pilot trial of interleukin-2 and zoledronic acid to augment γδ T cells as treatment for patients with refractory renal cell carcinoma," Cancer Immunol Immunother, vol. 60, pp. 1447-1460 (2011).

LeFranc et al., "IMGT unique numbering for immunoglobulin and T cell receptor variable domains and Ig superfamily V-like domains," Developmental & Comparative Immunology, vol. 27, pp. 55-77 (2003).

Li et al, "Transgenic mice with a diverse human T cell antigen receptor repertoire," Nature Med. vol. 16, pp. 1029-1035 (2010).

Linguiti et al, "Genomic and expression analyses of T cell receptor gamma (TRG) and alph/delta (TRA/TRD) loci reveal a similar basic public γδ repertoire in dolphin and human," MBC Genomics, vol. 17, No. 634, pp. 1-17 (2016).

Lloyd et al, "Modelling the human immune response: perfomance of a $10^{11}$ human antibody reperoire against a broad panel of therapeutically relevant antigens", Protein Engineering, Design & Selection, vol. 22, No. 3, pp. 1590168 (2009).

Lopez et al., "CD2-mediated IL0120dependent signals render human −T cells resistant to mitogen-induced apoptosis, permitting the large-scale ex vivo expansion of functionally distinct lymphocytes: implications for the development of adoptive immunotherapy strategies," Blood, vol. 96, pp. 3827-3837 (2000).

Luoma et al., "γδ T cell surveillance via CD1 molecules," Trens in Immunolgoy, vol. 35, No. 12, pp. 613-621 (2014).

Malmborg et al., "BIAcore as a tool in antibody engineering," J. Immunol. Methods, vol. 183, pp. 7-13 (1995).

Mangan et al., "Cutting Edge: CD1d Restriction and Th1/Th2/Th17 Cytokine Secretion by Human V 3 T Cells," J. of Immunol., vol. 191, pp. 30-34 (2013).

Michie et al., "Lifespan of human lymphocyte subsets defined by CD45 isoforms," Nature, vol. 360, pp. 364-365 (1992).

Moonka and Loh, "A consensus primer to amplify both α and β chains of the human T cell receptor," Journal of Immunological Methods, vol. 169, pp. 41-51 (1994).

Nagamine et al., Induction of γδ T Cells Using Zoledronate Plus Interleukin-2 in Patients with Metastatic Cancer, Hiroshima J. Med. Sci, vol. 58, No. 2, pp. 37-44 (2009).

Nakajima et al., "A phase I study of adoptive immunotherapy for recurrent non-small-cell lung cancer patients with autologous γδ T cells," European Journal of Cardio-thoracic Surgery, vol. 37, pp. 1191-1197 (2010).

Nicol et al., "Clinical evaluation of autologous gamma delta T cell-based immunotherapy for metastatic solid tumours," British Journal of Cancer, vol. 105, pp. 778-786 (2011).

Nussbaumer et al., "Essential Requirements of Zoledronate-Induced Cytokine and γδ T Cell Proliferative Responses,", J. of Immunol., vol. 191, No. 3, pp. 1346-1355 (2013).

Oberg et al., "γδ T cell activation by bispecific antibodies," Cellular Immunology, vol. 296, pp. 41-49 (2015).

Petros et al., "Improved analysis of TCR γδ variable region expression in humans," Journal of Immunological Methods, vol. 434, pp. 66-72 (2016).

Peyrat et al., "Repertoire analysis of human peripheral blood lymphocytes using a human V delta 3 region-specific monoclonal antibody. Characterization of dual T cell receptor (TCR) delta-chain expressors and alpha beta T cells expressing V delta 3J alpha C alpha-encoded TCR chains", J of Immunology, vol. 155, pp. 3060-3067 (1995).

Qi et al., "Immobilized MICA Could Expand Human Vδ1 γδT Cells in Vitro that Displayed Major Histocompatibility Complex Class I Chain-Related A-Dependent Cytotoxicity to Human Epithelial Carcinomas." Scandinavian Journal of Immunology, vol. 58, No. 2, pp. 211-220 (2003).

Rei et al., "The Emerging Protumor Role of γδ T Lymphocytes: Implications for Cancer Immunotherapy," Cancer Research, vol. 75(5), pp. 798-802 (2015).

Romagne F et al, "Structural analysis of gammadelta TCR using a novel set of TCR gamma and delta chain-specific monoclonal antibodies generated against soluble gammadelta TCR Evidence for a specific conformation adopted by the Jdelta2 region and for a Vdelta1 polymorphism", Journal of Immunological Methods, vol. 189, No. 1, pp. 25-36 (1996).

Sagar et al., "In vivo immunogenicity of Tax(11-19) epitope in HLA-A2/DTR transgenic mice: Implication for dendritic cell-based anti-HTLV-1 vaccine," Vaccine, vol. 32, , pp. 3274-3284 (2014).

Saitoh et al., "Anti-tumor cytotoxicity of γδ T cells expanded from peripheral blood cells of patients with myeloma and lymphoma," Med Oncol., vol. 25, pp. 137-147 (2008).

Sallusto et al., "Two subsets of memory T lymphocytes with distinct homing potentials and effector functions," Nature, vol. 401, p. 708-712 (1999).

Scheinberg et al., "Reaching Un-Drugable Intracellular Targets with the Long Arm of Antibodies," Oncotarget, vol. 4(5), pp. 647-648 (2013).

Scheper et al., "Hunting for clinical translation with innate-like immune cells and their receptors", Leukemia, vol. 28, No. 6, pp. 1181-1190 (2014).

Shang et al., "Rational optimization of tumor epitopes using in silico analysis-assisted substitution of TCR contact residues," European Journal of Immunology, vol. 39, pp. 2248-2258 (2009).

Sheriff and Constantine, "Redefining the minimal antigen-binding fragment," Nature Struct. Biol., vol. 3, No. 9, pp. 733-736 (1996).

Siegers et al., "Human V delta 1 gamma delta T cells expanded from peripheral blood exhibit specific cytotoxicity against B-cell chronic lymphocytic leukemia-derived cells", Cytoherapy, vol. 13, No. 6, pp. 753-764 (2011).

Siegers et al., "Extensive expansion of primary human gamma delta T cells generates cytotoxic effector memory cells that can be labeled with Feraheme for cellular MRI", Cancer Immunol. Immunother, vol. 62(3), pp. 571-583 (2012).

Taupin et al., "An enlarged subpopulation of T lymphocytes bearing two distinct [gamma][delta] TCR in an HIV-positive patient", International Immunology, vol. 11, No. 4, pp. 545-552 (1999).

TermoFisher Cientific—Useful Numbers for Cell Culture—obtained from www.thermofisher.com/US/en/home/references/gibo-cell-culture-basics/cell-culture-protocols/cell-culture-useful-numbers.html on Apr. 5, 2016 via the WayBackMachine, p. 1 (2016).

Vantourout et al., "Specific requirements for Vγ9Vδ2 T cell stimulation by a natural adenylated photphoantigen", J. Immunol., vol. 183(6), pp. 3848-3857 (2009).

Weidanz et al., "TCR-Like Biomolecules Target Peptide/MHC Class I Complexes on the Surface of Infected and Cancerous Cells," Int. Rev. Immunol., vol. 30, pp. 328-340 (2011).

Wild et al., "Dependence of T Cell Antigen Recognition on the Dimensions of an Accessory Receptor-Ligand Complex," J. Exp. Med, vol. 190, No. 1, pp. 31-41 (1999).

Wilhelm et al., "γδ T cells for immune therapy of patients with lymphoid malignancies, " Blood, vol. 102, No. 1, pp. 200-206 (2003).

Wilhelm et al., "Successful adoptive transfer and in vivo expansion of haploidentical γδ T Cells," J Transl Med., vol. 12, pp. 1-6 (2014).

Wistuba-Hamprecht K, Pawelec G, Derhovanessian E. OMIP-020: phenotypic characterization of human γδ T-cells by multicolor flow cytometry. Cytometry A., vol. 85(6) pp. 522-524 (2014).

Wu et al., "Ex vivo expanded human circulating Vδ1 γδ T cells exhibit favorable therapeutic potential for colon cancer," Oncoimmunology, vol. 4:3, pp. e992749-13 (2015).

Xu et al., "Diversity in the CDR3 region of V(H) is sufficient for most antibody specificities," Immunity, vol. 13, pp. 37-45 (2000).

Yin, et al., "Hyperactivation and in situ recruitment of inflammatory Vδ2 T cells contributes to disease pathogensissi in systemic lupus erythematosus,", Scientific Reports 5:14432, pp. 1-12 (2015).

Yoon et al., "The Cell Cycle Time of CD8+ T Cells Responding in Vivo is Controlled by the Type of Antigenic Stimulus," PLOS One, vol. 5(11), pp. 1-12 (2010).

(56) References Cited

OTHER PUBLICATIONS

Yu et al., "Expansion and Immunological Study of Human Tumor Infiltrating Gamma-Delta T Lymphocytes in vitro," Int Arch Allergy Immunol, vol. 119, pp. 31-37 (1999).

Zapata et al., "Engineering linear F(ab')2 fragments for efficient production in *Escherichia coli* and enhanced antiproliferative activity," Protein Eng. vol. 8, No. 10, pp. 1057-1062 (1995).

Zhou et al., "Anti-γδ TCR antibody-expanded γδ T cells: a better choice for the adoptive immunotherapy of lymphoid malignancies," Cellular & Molecular Immunology, vol. 9, pp. 34-44 (2012).

\* cited by examiner

| mAb | FW1 | CDRH1 | FW2 | CDRH2 | FW3 | CDRH3 | FW4 | SEQ ID |
|---|---|---|---|---|---|---|---|---|
| δ3-08 | EEKLEESGGGLVQPGGSMKLSCVASGFIFS | IYWMN | WVRQSPEKGLEWVG | QIRLKSDNYATHYAESVK | GRFTISRDDSKSSVYLQMNNLRAEDTGIYYCMY | YGSSYERFAY | WGQGTLVTVSA | 1 |
| δ3-20 | QVQLQQSGAELVRPGTSVRMSCKATGYTFS | NYWTG | WVKQRPGHGLERIG | DIYPGGGYTNYNEEFKG | KATLTADTSSSTVYMLLSSLTFEDSAIYYCAR | WGSDYAMDY | WGQGTSVTVSS | 2 |
| δ3-23 | EVQLQQSGAELVKPGASVKLSCTASGFNIRD | TYMH | WVKQRPEQGLEWIG | RIDPANGNTKYDPKFRG | KATITADTSSNTAYLQLSLTSEGTAVYYCSE | GIYFDY | WGQGTTLTVSS | 3 |
| δ3-31 | SDVQLQESGPDLVKPSQSLSLTCTVTGYSIT | SGYGWH | WIRQFPGNKLEWMG | YISFSGSNKYNPSLKS | RISITRDTSKNQFFLQLNSVTTEDTATYYCAN | LDY | WGQGTTLTVSS | 4 |
| δ3-42 | SDVQLQESGPDLVKPSQSLSLTCTVTGYSIT | SGYNWH | WIRQFPGNKLEWMG | YIHYSGNTDYNPSLRS | RISITRDTSKNQFFLHLNSVPTEDTATYYCAR | SGTITDWYFDV | WGAGTVTVSS | 5 |
| δ3-47 | EVQLQQSGAELVRPGASVKLSCTASGFNIK | DDYMN | WVKQRPEQGLDWIG | GIDPANGNTKYAPKFQD | KATITADTSSNTAYIQLSLTSEDTAVFYCAR | YRDYAVDYWGQG | WGQGTSVTVSS | 6 |
| δ3-58 | EVKLVESGGGLVQPGGSLKLSCAASGFTFS | SYAMS | WVRQTPEKRLEWVA | YIRDGGGGTYYPDTVEG | RFTISRDNAKNTLYLQMSLKSEDTAMYCAR | HPPMNDWFLY | WGQGTLVTVSA | 7 |

| mAb | FW1 | CDRL1 | FW2 | CDRL2 | FW3 | CDRL3 | FW4 | SEQ ID |
|---|---|---|---|---|---|---|---|---|
| δ3-08 | DIQMTQSPASLSVSVGETVTITC | RASENIYSNLA | WYQQKQGKSPQLLVYV | ATKLAD | GVPSRFSGSGSGTQYSLKINSLQSEDFGSYYC | QHFWGTPPWT | FGGGTKLEIK | 8 |
| δ3-20 | QIVLTQSPAIMSASPGEKVTMTC | SASSSVSSRYLH | WYQQKSGASPKFWIYG | TSNLAS | GVPARFSGSGSGTSYSLTISSVEAEDAATYYC | QQYHSDPPT | FGGGTKLEIK | 9 |
| δ3-23 | DILLTQSPAILSVSPGERVSFSC | RASQNIGTIIH | WYQQRANGSPRLLIKY | ASESIS | GIPSRFSGSGSGTDFTLSINSVESEDIADYYC | QQSNSWPYT | FGGGTKLEIKR | 10 |
| δ3-31 | SASQDINYLH | SASQDINYLH | WFQQKPDGTVKLLIY | YTSTLHS | GVPSRFSGSGSGTDYSLTISNLEPEDIATYYC | QQYSKLPYT | FGGGTKLEITR | 11 |
| δ3-42 | QIVLSQSPAIISASPGEKVTMTC | RASSSVNYMH | WYQQKPGSSPKPWIY | ATSNLAS | GVPARFSGSGSGTSYSLTISKVEAEDAATYYC | QQWSSHQPT | FGAGTKLELK | 12 |
| δ3-47 | DIRMTQSPSSMYASLGERVTITC | KASQDINTYLR | WCQQKPGKSPKTLIY | GANRLVD | GVPSRFSGSGSGQDYSLIISSLEYEDMGIYYC | LQYDEFPLT | FGAGTKLELK | 13 |
| δ3-58 | DIQMTQSPASLSVSVGETVTITC | RASENIYSHLA | WYQQKQGKSPQLLVY | AATNLAD | GVPSRFSGSGSGTQYSLKINSLQSEDFGSYYC | QHFWGTPYT | FGGGTKLEIKR | 14 |

FIG. 1

| | | Bin 1A | | | Bin 1B | Bin 2 |
|---|---|---|---|---|---|---|
| | MAb | δ3-23 | δ3-42 | δ3-58 | δ3-08 | δ3-31 |
| Bin 1A | δ3-23 | 0.06 | 0.04 | 0.03 | 0.04 | 0.40 |
| | δ3-42 | 0.12 | 0.04 | 0.06 | 0.01 | 0.37 |
| | δ3-58 | 0.07 | 0.03 | 0.03 | 0.04 | 0.38 |
| Bin 1B | δ3-08 | 0.29 | 0.21 | 0.22 | 0.16 | 0.44 |
| Bin 2 | δ3-31 | 0.48 | 0.35 | 0.37 | 0.24 | 0.07 |

FIG. 7

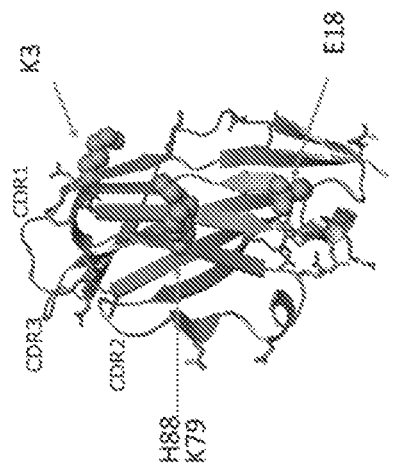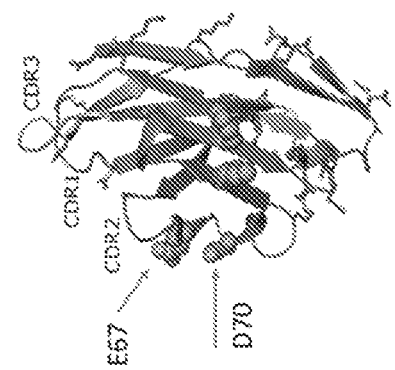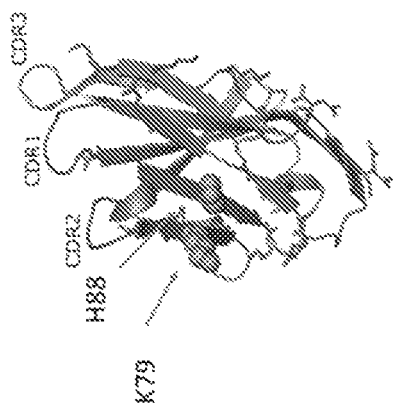
FIG. 13

METHODS FOR SELECTIVE EXPANSION OF DELTA-3 GAMMA DELTA T-CELL POPULATIONS AND COMPOSITIONS THEREOF

CROSS-REFERENCE TO RELATED APPLICATION

The present application claims the benefit of priority to U.S. Provisional Appl. No. 62/586,782, filed Nov. 15, 2017, the contents of which are hereby incorporated in the entirety and for all purposes.

SEQUENCE LISTING

The instant application contains a Sequence Listing which has been submitted electronically in ASCII format and is hereby incorporated by reference in its entirety. Said ASCII copy, created on Mar. 27, 2019, is named ADC-0003-WO_SL.txt and is 17,126 bytes in size.

BACKGROUND

Antigen recognition by T lymphocytes may be achieved by highly diverse heterodimeric receptors, the T-cell receptors (TCRs). Approximately 95% of human T-cells in blood and lymphoid organs express a heterodimeric αβ TCR receptor (αβ T-cell lineage). Approximately 5% of human T-cells in the blood and lymphoid organs express heterodimeric γδ TCR receptor (γδ T-cell lineage). These T-cell subsets may be referred to as 'αβ ' and 'γδ' T-cells, respectively. αβ and γδ T-cells are different in function. Activation of αβ T-cells then occurs when an antigen presenting cell (APC) presents an antigen in the context of class I/II MHC. In contrast to αβ T-cells, γδ T-cells can recognize an antigen independent of MHC restriction. In addition, γδ T-cells combine both innate and adoptive immune recognition and responses.

γδ T cells utilize a distinct set of somatically rearranged variable (V), diversity (D), joining (J), and constant (C) genes. γδ T cells contain fewer V, D, and J segments than αβ T cells. Although the number of germline Vγ and Vδ genes is more limited than the repertoire of Vα and Vβ TCR genes, more extensive junctional diversification processes during TCR γ and δ chain rearrangement leads to a potential larger γδ TCRs repertoire than that of αβTCRs (Carding and Egan, Nat Rev Immunol (2002) 2:336).

Human γδ T-cells use 3 main Vδ (Vδ1, Vδ2, Vδ3) and at most six Vγ region genes to make their TCRs (Hayday AC., Annu Rev Immunol. 2000;18, 975-1026). Two main Vδ subsets are Vδ1 and Vδ2 γδ T cells. Vδ1 T cells with different Vγ predominate in the intraepithelial subset of mucosal γδ T cells where the TCRs appear to recognize stress molecules on epithelial cells (Beagley K W, Husband AJ. Crit Rev Immunol. 1998; 18(3):237-254). Vδ2 T cells that generally coexpress Vγ9 are abundant in the peripheral blood and lymphatic system.

The ability of γδ T-cells to recognize an antigen on diseased cells directly and to exhibit inherent ability to kill tumor cells renders γδ T-cells an attractive therapeutic tool. Adoptive transfer of Vγ9Vδ2 T cells has yielded limited objective clinical responses for investigational treatment of cancer (Kondo et al, Cytotherapy, 10:842-856, 2008; Lang et al, Cancer Immunology, Immunotherapy: CII, 60: 1447-1460, 2011; Nagamine et al, 2009; Nicol et al, British Journal of Cancer, 105:778-786, 2011; Wilhelm et al, Blood. 2003 Jul. 1; 102(1):200-6), indicating the need to isolate and test clinically new γδ T-cell populations.

The ability to selectively expand γδ T-cell subset populations having potent anti-tumor activity with improved purity and in clinically-relevant levels is highly desirable. Although antibodies and cytokine cocktails have been used to propagate a more diverse set of γδ T cells, activation of specific γδ T-cell subsets to sufficient purity and clinically-relevant levels, was not achieved (Dokouhaki et al, 2010; Kang et al, 2009; Lopez et al, 2000; Kress, 2006). Therefore, clinically-relevant methods of expanding specific γδ T cell subsets ex vivo, and the cells produced thereby, are greatly needed.

SUMMARY OF THE INVENTION

The present invention, in one aspect, provides ex vivo methods for producing enriched γδ T cell populations. The enriched γδ T cell populations can be produced from isolated mixed cell populations by a method comprising contacting the mixed cell population, or a purified fraction thereof, with one or more agents that selectively expand δ3 T cells by binding to an epitope specific to a δ3 TCR. The expanded T cell populations can be used, e.g., individually or in combination with other T cell populations, in methods of treatment by administering to a subject in need thereof. In some cases, the agents are antibodies or fragments thereof.

In a first aspect, the present invention provides an agent that selectively binds an epitope specific to a δ3 γδ TCR. In some embodiments, the agent is an antibody or a fragment thereof. In some embodiments, the agent is an activating agent that selectively binds an activating epitope specific to a δ3 γδ TCR.

In some embodiments, the agent (e.g., antibody or fragment thereof) binds the same epitope, or essentially the same epitope, as (or competes with) an antibody selected from the group consisting of δ3-08, δ3-20, δ3-23, δ3-31, δ3-42, δ3-47, and δ3-58. In some embodiments, the agent (e.g., antibody or fragment thereof) binds the same epitope, or essentially the same epitope, as (or competes with) an antibody selected from the group consisting of δ3-08, δ3-23, δ3-31, δ3-42, δ3-47, and δ3-58. In some embodiments, the agent (e.g., antibody or fragment thereof) comprises the complementarity determining regions of an antibody selected from the group consisting of δ3-08, δ3-20, δ3-23, δ3-31, δ3-42, δ3-47, and δ3-58. In some embodiments, the agent (e.g., antibody or fragment thereof) comprises the complementarity determining regions of an antibody selected from the group consisting of δ3-08, δ3-23, δ3-31, δ3-42, δ3-47, and δ3-58.

In some embodiments, the agent (e.g., antibody or fragment thereof) competes with binding of antibody δ3-23, δ3-42, and/or δ3-58 to a δ3 TCR (e.g., a 7263 TCR). In some embodiments, the agent (e.g., antibody or fragment thereof) competes with binding of antibody δ3-08 to a δ3 TCR (e.g., a γ2 δ3 TCR). In some embodiments, the agent (e.g., antibody or fragment thereof) competes with binding of antibody δ3-08, δ3-23, δ3-42, and/or δ3-58 to a δ3 TCR (e.g., a γ2 δ3 TCR). In some embodiments, the agent (e.g., antibody or fragment thereof) competes with binding of antibody δ3-31 to a δ3 TCR (e.g., a γ2 δ3 TCR).

In some embodiments, the agent (e.g., antibody or fragment thereof) selectively expands a δ3 γδ T cell as compared to αβ T cells in a mixed cell population comprising γδ T cells and αβ T cells. In some embodiments, the agent (e.g., antibody or fragment thereof) is bound to a δ3 γδ TCR. In some embodiments, the δ3 γδ TCR is expressed on the surface of an engineered δ3 γδ T cell. In some embodiments, the δ3 γδ TCR is expressed on the surface of a non-engineered δ3 γδ T cell, such as a selectively expanded non-engineered δ3 γδ T cell. In some embodiments, the agent (e.g., antibody or fragment thereof) is bound to a δ3 γδ TCR expressed on the surface of a δ3 γδ T cell. In some cases, the agent (e.g., antibody or fragment thereof) bound to the δ3 γδ TCR expressed on the surface of a δ3 γδ T cell forms an isolated complex with the δ3 γδ T cell, is in a subject, is in an ex vivo or in vitro culture, or is in a container. In some embodiments, the agent (e.g., antibody or fragment thereof) is bound to a δ3 γδ TCR expressed on the surface of a δ3 γδ T cell in an ex vivo expansion culture.

In some embodiments, the agent (e.g., antibody or fragment thereof) is bound to an extracellular surface of an antigen presenting cell (APC). In some embodiments, the agent (e.g., antibody or fragment thereof) is anchored in the membrane of the APC. In some embodiments, an Fc region of the agent (e.g., antibody or fragment thereof) is bound to an Fc-receptor expressed by the APC. In some cases, the APC is an artificial APC (aAPC). In some cases, the APC is in a subject, isolated, in an ex vivo or in vitro culture, or is in a container.

In some cases, the agent (e.g., antibody or fragment thereof) binds to a region distal from the γ-chain binding interface of Vδ3. In some cases, the agent (e.g., antibody or fragment thereof) binds to R strand D and E of the Vδ3 of the γδ TCR according to IMGT nomenclature. In some cases, the agent (e.g., antibody or fragment thereof) binds to β strand C" and D and a loop between R strands E and F of the Vδ3 of the γδ TCR according to IMGT nomenclature. In some cases, the agent (e.g., antibody or fragment thereof) binds to R strand A, B, D, and E of the Vδ3 of the γδ TCR according to IMGT nomenclature.

In some cases, the agent (e.g., antibody or fragment thereof) binds to amino acids K79 and H88 of Vδ3 (IMGT nomenclature). In some cases, the agent (e.g., antibody or fragment thereof) binds to amino acids R75 and R95 of Vδ3 (IMGT nomenclature). In some cases, the agent (e.g., antibody or fragment thereof) binds to amino acids K79, E18, and H88 of Vδ3 (IMGT nomenclature). In some cases, the agent (e.g., antibody or fragment thereof) binds to amino acids E67, D70, R75, R95, and E97 of Vδ3 (IMGT nomenclature). In some cases, the agent (e.g., antibody or fragment thereof) binds to amino acids K3, K79, and H88 of Vδ3 (IMGT nomenclature). In some cases, the agent (e.g., antibody or fragment thereof) binds to amino acids K79, L82, and H88 of Vδ3 (IMGT nomenclature). Typically, the agent binds the specified amino acids or groups thereof in the context of a Vδ3 γδ TCR, such as a Vδ3 γδ TCR expressed on the surface of a Vδ3 γδ T cell.

In a second aspect, the present invention provides a nucleic acid encoding any one of the foregoing agents (e.g., antibodies or fragments thereof). In some cases, the nucleic acid is operably linked to a heterologous promoter. In a third aspect, the present invention provides a host cell comprising any one of the foregoing agents or any one of the foregoing nucleic acids. In some cases, the host cell is an artificial antigen presenting cell (aAPC).

In a fourth aspect, the present invention provides a method of making an agent (e.g., antibody or fragment thereof) that binds an epitope specific to a δ3 γδ TCR, the method comprising culturing any one of the foregoing host cells under conditions sufficient to produce the antibody or fragment thereof.

In a fifth aspect, the present invention provides an ex vivo method for producing an enriched γδ T cell population, comprising contacting a first cell population comprising γδ T cells with one or more of the foregoing agents (e.g., antibodies or fragments thereof). In some embodiments, the first cell population is an isolated mixed cell population comprising αβ T cells and γδ T cells (e.g., δ3 γδ T cells). In some embodiments, the first cell population is selected from a peripheral blood sample, a leukapheresis sample, a cord blood sample, a tumor sample, or a tissue sample. In some cases, the first cell population is a sample isolated from a single donor. In some cases, the first cell population is a sample isolated from multiple donors. In some cases, the first cell population is a PBMC sample. In some cases, the first cell population is a sample of PBMCs isolated from a single donor. In some cases, the first cell population is a sample of PBMCs isolated from multiple donors.

In some embodiments, the method comprises directly contacting the isolated mixed cell population with the one or more of the foregoing agents (e.g., antibodies or fragments thereof). In some embodiments, the first cell population is a population comprising one or more engineered γδ T cells. In some embodiments, the first cell population is a first population of expanded γδ T cells. In some embodiments, the method comprises a first γδ T cell expansion and a second γδ T cell expansion. In some embodiments, the method comprises producing an enriched γδ T cell population comprising at least $10^8$ δ3 γδ T cells. In some embodiments, the enriched γδ T cell population comprising at least $10^8$ δ3 γδ T cells is produced within 12 to 21 days. In some embodiments, the method comprises expanding the γδ T cells in the first cell population at least 1,000-fold. In some embodiments, the at least 1,000-fold expansion is achieved within 12 to 21 days.

In a sixth aspect, the present invention provides an ex vivo method for producing an enriched γδ T cell population, comprising: a) contacting a first cell population comprising γδ T cells with one or more first activating agents that activate and expand γδ T cells, thereby producing an expanded first γδ T cell population; and b) contacting the expanded first γδ T cell population with one or more second activating agents that activate and expand γδ T cells, thereby producing the enriched γδ T cell population, wherein, at least one of the one or more first activating agents or at least one of the one or more second activating agents is an agent (e.g., antibody or fragment thereof) according to the first aspect. In some embodiments, the method comprises isolating the expanded first γδ T cell population after a) and before b). In some embodiments, a) comprises culturing the first cell population in the presence of an antigen presenting cell (APC) and the one or more first activating agents. In some embodiments, b) comprises culturing the activated γδ T cell population in the presence of an antigen presenting cell (APC) and the one or more second activating agents.

In some embodiments, the first cell population is an isolated mixed cell population comprising αβ T cells and γδ T cells. In some embodiments, the first cell population is selected from a peripheral blood sample, a leukapheresis sample, a cord blood sample, a tumor sample, or a tissue sample. In some embodiments, the first cell population is a population of engineered γδ T cells. In some embodiments, the method comprises genetically modifying the expanded first γδ T cell population or genetically modifying the enriched γδ T cell population. In some embodiments, the method comprises producing an enriched γδ T cell population comprising at least $10^8$ δ3 γδ T cells. In some embodiments, the enriched γδ T cell population comprising at least $10^8$ δ3 γδ T cells is produced within 12 to 21 days.

In some embodiments, the method comprises expanding the γδ T cells in the first cell population at least 1,000-fold. In some embodiments, the at least 1,000-fold expansion is achieved within 12 to 21 days.

In some embodiments, at least one of the one or more first activating agents is structurally identical to at least one of the one or more second activating agents. In some embodiments, at least one of the one or more first activating agents is structurally different than at least one of the one or more second activating agents. In some embodiments, at least one of the one or more first activating agents or at least one of the one or more second activating agents is immobilized. In some embodiments, the immobilized activating agent is immobilized on a surface of a culture vessel. In some embodiments, the immobilized activating agent is immobilized on a surface of an antigen presenting cell (APC). In some embodiments, the immobilized activating agent is the agent (e.g., antibody or fragment thereof) that binds the epitope specific to a δ3 γδ TCR.

In a seventh aspect, the present invention provides an expanded γδ T cell population (e.g., before positive or negative selection for δ3 γδ T cells), wherein greater than 10%, 20%, 30%, 40%, 50%, 60%, 70%, 75%, or 80% of the expanded γδ T cells are δ3 γδ T cells. In some embodiments, from 10% to 80% of the expanded γδ T cells are δ3 γδ T cells (e.g., before positive or negative selection for δ3 γδ T cells). In some embodiments, from 10% to 60% of the expanded γδ T cells are δ3 γδ T cells (e.g., before positive or negative selection for δ3 γδ T cells). In some embodiments, from 10% to 40% of the expanded γδ T cells are δ3 γδ T cells (e.g., before positive or negative selection for δ3 γδ T cells). In some embodiments, from 20% to 80% of the expanded γδ T cells are δ3 γδ T cells (e.g., before positive or negative selection for δ3 γδ T cells). In some embodiments, from 20% to 60% of the expanded γδ T cells are δ3 γδ T cells (e.g., before positive or negative selection for δ3 γδ T cells). In some embodiments, from 20% to 50% of the expanded γδ T cells are δ3 γδ T cells (e.g., before positive or negative selection for δ3 γδ T cells). In some embodiments, from 20% to 40% of the expanded γδ T cells are δ3 γδ T cells (e.g., before positive or negative selection for δ3 γδ T cells).

In some embodiments, the expanded γδ T cell population comprises polyclonal TCR diversity. In some embodiments, greater than 30%, 40%, 50%, 60%, or 70% of the δ3 γδ T cells in the expanded γδ T cell population express the phenotype CD45RA+/CD27+ and/or CD45RA−/CD27+. In some embodiments, from 20% to 70% of the δ3 γδ T cells in the expanded γδ T cell population express the phenotype CD45RA+/CD27+ and/or CD45RA−/CD27+. In some embodiments, greater than 30%, 40%, 50%, 60%, or 70% of the δ1−/δ2− γδ T cells in the expanded γδ T cell population express the phenotype CD45RA+/CD27+ and/or CD45RA−/CD27+. In some embodiments, from 20% to 70% of the δ1−/δ2− γδ T cells in the expanded γδ T cell population express the phenotype CD45RA+/CD27+ and/or CD45RA−/CD27+.

In some embodiments, the expanded γδ T cell population is derived from a tissue such as skin. In some embodiments, the expanded γδ T cell population is derived from tumor infiltrating lymphocytes. In some embodiments, the expanded γδ T cell population comprises γδ T-cells that express an endogenous or heterologous tumor recognition moiety. In some embodiments, the population comprises a therapeutically effective amount (e.g., >10δ) of γδ T-cells. In some embodiments, the γδ T cell population comprises anti-tumor cytotoxicity that is independent of NKp30 activity, NKp44 activity, and/or NKp46 activity. In some embodiments, the γδ T cell population does not comprise NKp30 activity-dependent anti-tumor cytotoxicity, NKp44 activity-dependent anti-tumor cytotoxicity, and/or NKp46 activity-dependent anti-tumor cytotoxicity. In some embodiments, less than 40% of the γδ T cells express (e.g., as protein or mRNA) a detectable level of NKp30, NKp44, and/or NKp46.

In an eighth aspect, the present invention provides an expanded γδ T cell population, which is produced by any one of the foregoing methods. In a ninth aspect, the present invention provides a method of treating cancer, an inflammatory disease, or an autoimmune disease in a subject in need thereof, the method comprising administering a therapeutically effective amount of δ3 γδ T cells to the subject, administering a therapeutically effective amount of a γδ T cell population that is enriched in δ3 γδ T cells to the subject, or administering to the subject a therapeutically effective amount of a γδ T cell population obtained by a method described herein.

In a tenth aspect, the present invention provides a method of treating cancer, an inflammatory disease, or an autoimmune disease in a subject in need thereof, the method comprising: a) providing a therapeutically effective amount of δ3 γδ T cells isolated from any one or more of the foregoing expanded γδ T cell populations; and administering the therapeutically effective amount of δ3 γδ T cells to the subject. In some embodiments, the method further comprises admixing the expanded γδ T cell population with a different expanded γδ T cell population to form an admixed population and administering the admixed population to the subject.

In some embodiments, the different expanded γδ T cell population comprises an amount of expanded δ1 γδ T cells, and/or an amount of expanded δ2 γδ T cells. In some embodiments, the different expanded γδ T cell population comprises >5% δ1 (e.g., >10%, 20%, 30%, 40%, 50%, 60%, 70%, 80%, or 90% δ1) or >5% δ2 (e.g., >10%, 20%, 30%, 40%, 50%, 60%, 70%, 80%, or 90% δ2) γδ T cells. In some embodiments, the different expanded γδ T cell population comprises from about, or at least about, 60% to about 90% δ1 γδ T cells, or from about, or at least about, 60% to about 80% δ1 γδ T cells. In some embodiments, the different expanded γδ T cell population comprises from about, or at least about, 60% to about 90% δ2 γδ T cells, from about, or at least about, 70% to about 80% δ2 γδ T cells, or from about, or at least about, 80% to about 90% δ2 γδ T cells.

In some embodiments, the admixed γδ T cell population comprises an amount of δ1 γδ T cells, and/or an amount of δ2 γδ T cells, and an amount of δ3 γδ T cells. In some embodiments, the admixed γδ T cell population comprises >5% δ1 (e.g., >10%, 20%, 30%, 40%, 50%, 60%, 70%, 80%, or 90% δ1) or >5% δ2 (e.g., >10%, 20%, 30%, 40%, 50%, 60%, 70%, 80%, or 90% δ2) γδ T cells. In some embodiments, the admixed γδ T cell population comprises >5% δ3 (e.g., >10%, 20%, 30%, 40%, 50%, 60%, 70%, 80%, or 90% δ3) γδ T cells. In some embodiments, the admixed γδ T cell population comprises from about, or at least about, 5% to about 90% δ3 γδ T cells, from about, or at least about, 10% to about 90% δ3 γδ T cells, from about, or at least about, 20% to about 90% δ3 γδ T cells, from about, or at least about, 30% to about 90% δ3 γδ T cells, from about, or at least about, 40% to about 90% δ3 γδ T cells, from about, or at least about, 50% to about 90% δ3 γδ T cells, from about, or at least about, 60% to about 90% δ3 γδ T cells, from about, or at least about, 70% to about 90% δ3 γδ T cells, or from about, or at least about, 80% to about 90% δ3 γδ T cells.

In some embodiments, the admixed γδ T cell population comprises from about, or at least about, 5% to about 90% δ1 γδ T cells, from about, or at least about, 10% to about 90% δ1 γδ T cells, from about, or at least about, 20% to about 90% δ1 γδ T cells, from about, or at least about, 30% to about 90% δ1 γδ T cells, from about, or at least about, 40% to about 90% δ1 γδ T cells, from about, or at least about, 50% to about 90% δ1 γδ T cells, from about, or at least about, 60% to about 90% δ1 γδ T cells, from about, or at least about, 70% to about 90% δ1 γδ T cells, or from about, or at least about, 80% to about 90% δ1 γδ T cells. In some embodiments, the admixed γδ T cell population comprises from about, or at least about, 5% to about 90% δ2 γδ T cells, from about, or at least about, 10% to about 90% δ2 γδ T cells, from about, or at least about, 20% to about 90% δ2 γδ T cells, from about, or at least about, 30% to about 90% δ2 γδ T cells, from about, or at least about, 40% to about 90% δ2 γδ T cells, from about, or at least about, 50% to about 90% δ2 γδ T cells, from about, or at least about, 60% to about 90% δ2 γδ T cells, from about, or at least about, 70% to about 90% δ2 γδ T cells, or from about, or at least about, 80% to about 90% δ2 γδ T cells.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 1 shows variable region sequences of δ3-specific anti-γδ TCR antibodies. Top sequence of heavy chain variable regions. Bottom sequence of light chain variable regions.

FIG. 7 illustrates results of a competition assay for binding of the indicated δ3 γδ TCR specific antibodies to γ2δ3TCR-hFc recombinant protein.

FIG. 13 illustrates 3 different projections of a 3D model of antigen binding hot spots identified by fine epitope mapping via mutagenesis as described in Example 7.

DETAILED DESCRIPTION OF THE INVENTION

Figure 2:
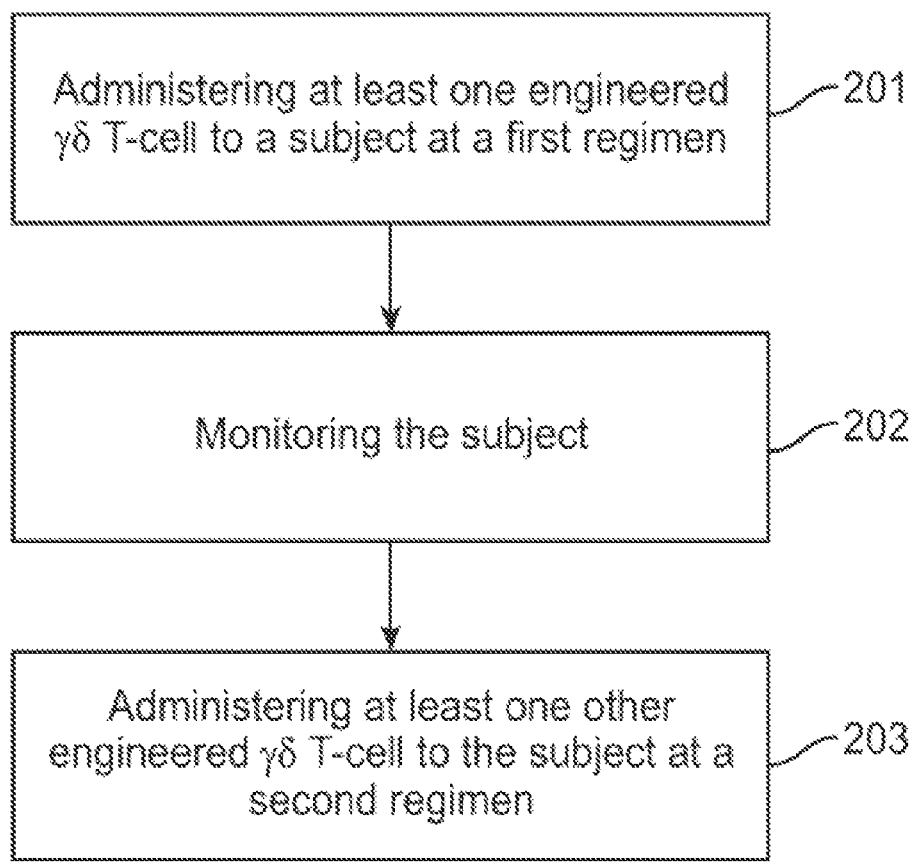
FIG. 2 schematically illustrates a method for treating a subject.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Unless defined otherwise, all technical and scientific terms used herein have the same meaning as commonly understood to one of ordinary skill in the art to which the inventions described herein belong. For purposes of interpreting this specification, the following definitions will apply and whenever appropriate, terms used in the singular will also include the plural and vice versa. In the event that any definition set forth conflicts with any document incorporated herein by reference, the definition set forth below shall control.

The term "γδ T cells (gamma delta T cells)" as used herein refers to a subset of T-cells that express a distinct T-cell receptor (TCR), γδ TCR, on their surface, composed of one T-chain and one δ-chain. The term "γδ T cells" specifically includes all subsets of γδ T cells and combinations thereof, including, without limitation, Vδ3 γδ T cells, as well as naïve, effector memory, central memory, and terminally differentiated γδ T-cells. As a further example, the term "γδ T-cells" includes Vδ1, Vδ2, Vδ3, Vδ4, Vδ5, Vδ7, and Vδ8 γδ T cells, as well as Vγ2, Vγ3, Vγ5, Vγ8, Vγ9, Vγ10, and Vγ11 γδ T cells. As a further example, the term "γδ T-cells" includes Vδ3γ2 T cells, and optionally can include or refer to Vδ3γ8 T cells.

As used herein, the term "T lymphocyte" or "T cell" refers to an immune cell expressing CD3 (CD3+) and a T Cell Receptor (TCR+). T cells play a central role in cell-mediated immunity.

As used herein, the term "TCR" or "T cell receptor" refers to a dimeric heterologous cell surface signaling protein forming an alpha-beta or gamma-delta receptor. αβ TCR recognize an antigen presented by an MHC molecule, whereas γδ TCR recognize an antigen independently of MHC presentation.

The term "MHC" (major histocompatibility complex) refers to a subset of genes that encodes cell-surface antigen-presenting proteins. In humans, these genes are referred to as human leukocyte antigen (HLA) genes. Herein, the abbreviations MHC or HLA are used interchangeably.

As used herein, the term "peripheral blood lymphocyte(s)" or "PBL(s)" is used in the broadest sense and refers to white blood cell(s) comprising T cells and B cells of a range of differentiation and functional stages, plasma cells, monocytes, macrophages, natural killer cells, basocytes, eosinophils, etc. The range of T lymphocytes in peripheral blood is about 20-80%.

As used herein, the term "cell population" refers to a number of cells obtained by isolation directly from a suitable source, usually from a mammal. The isolated cell population may be subsequently cultured in vitro. Those of ordinary skill in the art will appreciate that various methods for isolating and culturing cell populations are suitable for use with the present invention and various numbers of cells in a cell population are suitable for use in the present invention. A cell population may be purified to homogeneity, substantial homogeneity, or to deplete one or more cell types (e.g., αβ T cells) by various culture techniques and/or negative or positive selection for a specified cell type. A cell population may be, for example, a mixed heterogeneous cell population derived (e.g., directly isolated) from a peripheral blood sample, a cord blood sample, a tumor, a stem cell precursor, a tumor biopsy, a tissue, a lymph, skin, a sample of or containing tumor infiltrating lymphocytes, or from epithelial sites of a subject directly contacting the external milieu, or derived from stem precursor cells. Alternatively, the mixed cell population may be derived from in vitro cultures of mammalian cells, established from a peripheral blood sample, a cord blood sample, a tumor, a stem cell precursor, a tumor biopsy, a tissue, a lymph, skin, a sample of or containing tumor infiltrating lymphocytes, or from epithelial sites of a subject directly contacting the external milieu, or derived from stem precursor cells.

An "enriched" cell population or preparation refers to a cell population derived from a starting mixed cell population that contains a greater percentage of a specific cell type than the percentage of that cell type in the starting population. For example, a starting mixed cell population can be enriched for a specific γδ T-cell population. In one embodiment, the enriched γδ T-cell population contains a greater percentage of δ3 cells than the percentage of that cell type in the starting population. As another example, an enriched γδ T-cell population can contain a greater percentage of both δ1 cells and a greater percentage of δ3 cells than the percentage of that cell type in the starting population. As yet another example, an enriched γδ T-cell population can contain a greater percentage of both δ3 cells and a greater percentage of δ4 cells than the percentage of that cell type in the starting population. As yet another example, an enriched γδ T-cell population can contain a greater percentage of δ1 T cells, δ3 T cells, δ4 T cells, and δ5 T cells than the percentage of that cell type in the starting population. In another embodiment, the enriched γδ T cell population contains a greater percentage of δ2 T cells and δ3 T cells than the percentage of that cell type in the starting population. In yet another embodiment, the enriched γδ T cell population contains a greater percentage of δ1 T cells δ2 T cells and δ3 T cells than the percentage of that cell type in the starting population. In all embodiments, the enriched γδ T cell population contains a lesser percentage of αβ T cells than the percentage of αβ T cells in the starting population.

By "expanded" as used herein is meant that the number of the desired or target cell type (e.g., δ3 T cells) in the enriched preparation is higher than the number in the initial or starting cell population. By "selectively expand" is meant that the target cell type (e.g., δ3 T cells) are preferentially expanded over one or more other non-target cell types, e.g., αβ T-cells, NK cells, and/or one or more γδ T cell sub-populations not expanded by a selective activating agent used in the selective expansion. In certain embodiments, the activating agents of the invention selectively expand, e.g., engineered or non-engineered, δ3 T-cells without, or without significant, expansion of αβ T cells. In certain embodiments, the activating agents of the invention selectively expand, e.g., engineered or non-engineered, δ3 T-cells without, or without significant, expansion of δ1 T cells. In other embodiments, the activating agents of the invention selectively expand, e.g., engineered or non-engineered, δ3 T cells without, or without significant, expansion of δ2 T cells. In certain embodiments, the activating agents of the invention selectively expand, e.g., engineered or non-engineered, δ3 T-cells without, or without significant, expansion of δ1 T cells and δ2 T cells. In certain embodiments, the activating agents of the invention selectively expand, e.g., engineered or non-engineered, δ1 and δ3 T cells without, or without significant, expansion of δ2 T cells. In this context, the term "without significant expansion of" means that the preferentially expanded cell population are expanded at least 10-fold, preferably 100-fold, and more preferably 1,000-fold more than the reference cell population.

The term "admixture" as used herein refers to a combination of two or more isolated, enriched cell populations derived from a mixed, heterogeneous cell population. According to certain embodiments, the cell populations of the present invention are isolated γδ T cell populations.

The term "isolated," as applied to a cell population, refers to a cell population, isolated from the human or animal body, which is substantially free of one or more cell populations that are associated with said cell population in vivo or in vitro.

The term "contacting" in the context of a cell population, as used here refers to incubation of an isolated cell population with a reagent, such as, for example, an antibody, cytokine, ligand, mitogen, or co-stimulatory molecule that can be linked either to beads or to cells. The antibody or cytokine can be in a soluble form, or it can be immobilized. In one embodiment, the immobilized antibody or cytokine is tightly bound or covalently linked to a bead or plate. In one embodiment, the antibody is immobilized on Fc-coated wells. In one embodiment, the antibody is immobilized on a surface of a cell such as an antigen presenting cell (APC) or an artificial antigen presenting cell (aAPC). In desirable embodiments, the contact occurs ex vivo (e.g., in vitro) or in vivo.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "directed against" is meant that the antibody reacts with one or more antigenic determinants of the desired antigen and does not react with other polypeptides or binds at much lower affinity ($K_D$>$10^{-6}$ molar). Antibodies include, but are not limited to, polyclonal, monoclonal, chimeric, sdAb (heavy or light single domain antibody), single chain, $F_{ab}$, $F_{ab'}$ and $F_{(ab')2}$ fragments, scFvs, diabodies, minibodies, nanobodies, and $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "Fab" refers to an antibody fragment that consists of an entire L chain ($V_L$ and $C_L$) along with the variable region domain of the H chain ($V_H$), and the first constant domain of one heavy chain (CH1). Papain digestion of an intact antibody can be used to produce two Fab fragments, each of which contains a single antigen-binding site. Typically, the L chain and H chain fragment of the Fab produced by papain digestion are linked by an interchain disulfide bond.

The term "Fc" refers to an antibody fragment that comprises the carboxy-terminal portions of both H chains (CH2 and CH3) and a portion of the hinge region held together by disulfide bonds. The effector functions of antibodies are determined by sequences in the Fc region; this region is also the part recognized by Fc receptors (FcR) found on certain types of cells. One Fc fragment can be obtained by papain digestion of an intact antibody.

The term "F(ab')$_2$" refers to an antibody fragment produced by pepsin digestion of an intact antibody. F(ab')$_2$ fragments contain two Fab fragments and a portion of the hinge region held together by disulfide bonds. F(ab')$_2$ fragments have divalent antigen-binding activity and are capable of cross-linking antigen.

The term Fab' refers to an antibody fragment that is the product of reduction of an F(ab')$_2$ fragment. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group.

The term "Fv" refers to an antibody fragment that consists of a dimer of one heavy-chain variable region and one light-chain variable region domain in tight, non-covalent association.

From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

The term "single-chain Fv" also abbreviated as "sFv" or "scFv" refer to antibody fragments that comprise the VH and VL antibody domains connected into a single polypeptide chain. Typically, the scFv polypeptide further comprises a polypeptide linker between the VH and VL domains, which enables the scFv to form the desired structure for antigen binding. For a review of scFv, see, e.g., Pluckthun, *The Pharmacology of Monoclonal Antibodies*, vol. 113, Rosenburg and Moore eds., Springer-Verlag, New York, pp. 269-315 (1994); and Malmborg et al., J. Immunol. Methods 183:7-13, 1995.

The expression "linear antibody" is used to refer to a polypeptide comprising a pair of tandem $V_H$-$C_H$1 segments ($V_H$-$C_H$1-$V_H$-$C_H$1) which form a pair of antigen binding regions. Linear antibodies can be bispecific or monospecific and are described, for example, by Zapata et al., *Protein Eng.* 8(10):1057-1062 (1995).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The term "hypervariable region," "HVR," or "HV," refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

"Framework regions" (FR) are those variable domain residues other than the CDR residues. Each variable domain typically has four FRs identified as FR1, FR2, FR3, and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In certain instances, for the VL, the subgroup is subgroup kappa I as in Kabat. In certain instances, for the VH, the subgroup is subgroup III as in Kabat.

An antibody described herein can be humanized. "Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma and Immunol., 1:105-115 (1998); Harris, Biochem. Soc. Transactions, 23:1035-1038 (1995); Hurle and Gross, Curr. Op. Biotech., 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

As used herein, the "Kd" or "Kd value" refers to a dissociation constant measured by using surface plasmon resonance assays, for example, using a BIAcore™-2000 or a BIAcore™-3000 (BIAcore, Inc., Piscataway, N.J.) at 25° C. with CM5 chips immobilized with antigen or antibody at about 10 response units (RU). For divalent or other multivalent antibodies, typically the antibody is immobilized to avoid avidity-induced interference with measurement of the dissociation constant. For further details see, e.g., Chen et al., *J. Mol. Biol.* 293:865-881 (1999).

"Or better" when used herein to refer to binding affinity refers to a stronger binding between a molecule and its binding partner. "Or better" when used herein refers to a stronger binding, represented by a smaller numerical $K_D$ value. For example, an antibody which has an affinity for an antigen of "0.6 nM or better", the antibody's affinity for the antigen is <0.6 nM, i.e. 0.59 nM, 0.58 nM, 0.57 nM etc. or any value less than or equal to 0.6 nM.

The term "epitope" includes any protein determinant, lipid or carbohydrate determinant capable of specific binding to an immunoglobulin or T-cell receptor. Epitopic determinants usually consist of active surface groupings of molecules such as amino acids, lipids or sugar side chains and usually have specific three dimensional structural characteristics, as well as specific charge characteristics. An antibody is said to specifically bind an antigen when the equilibrium dissociation constant ($K_D$) is within the range of $10^{-6}$-$10^{-12}$M, or better. Specific binding can refer to binding to a target epitope with at least a 10-fold; preferably 100-fold; or more preferably 1,000-fold tighter dissociation constant (lower $K_D$), as compared to the dissociation constant for binding to other non-target epitopes. In some cases, the target epitope is an epitope of a delta-3 chain of a delta-3 TCR. In some cases, the non-target epitope is an $\alpha\beta$ TCR. In some cases, the non-target epitope is a delta chain of a $\delta$-TCR that is not delta-3. For example, in some cases, the non-target epitope can be a delta-1, delta-2, delta-4, delta-5, or delta-8 chain of a $\delta$-TCR. Specificity of binding can be determined in the context of binding to a extracellular region of a $\gamma\delta$-TCR and/or $\alpha\beta$-TCR (e.g., as an Fc fusion immobilized on an ELISA plate or as expressed on a cell).

An "activating epitope" is capable of activation of the specific $\gamma\delta$ T-cell population upon binding. T cell proliferation indicates T cell activation and expansion.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in a number of different formats, using either labeled antigen or labeled antibody. In some embodiments, the antigen is immobilized on a 96-well plate, and the ability of unlabeled antibodies to block the binding of labeled antibodies is measured using radioactive or enzyme labels. Alternatively, the competition studies, using labelled and unlabeled antibodies, are performed using flow cytometry on antigen-expressing cells.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. "Epitope binning", as defined herein, is the process of grouping antibodies based on the epitopes they recognize. More particularly, epitope binning comprises methods and systems for discriminating the epitope recognition properties of different antibodies, combined with computational processes for clustering antibodies based on their epitope recognition properties and identifying antibodies having distinct binding specificities.

The term "chimeric antigen receptors (CARs)," as used herein, may refer to artificial T-cell receptors, T-bodies, single-chain immunoreceptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain (allowing the T cell to activate upon engagement of targeting moiety with target cell, such as a target tumor cell), a transmembrane domain, and an extracellular domain that may vary in length and comprises a disease- or disorder-associated, e.g., a tumor-antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP 10/12, and/or OX40, ICOS, TLRs, etc. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

An "agent" or "compound" according to the present invention comprises small molecules, polypeptides, proteins, antibodies or antibody fragments. Small molecules, in the context of the present invention, mean in one embodiment chemicals with molecular weight smaller than 1000 Daltons, particularly smaller than 800 Daltons, more particularly smaller than 500 Daltons. The term "therapeutic agent" refers to an agent that has biological activity. The term "anti-cancer agent" refers to an agent that has biological activity against cancer cells.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including stem cells, blood cells, embryonic cord blood cells, tumor cells, transduced cells, etc.

The terms "treat" or "treatment" refer to both therapeutic treatment and prophylactic or preventative measures, wherein the object is to prevent or slow down (lessen) an undesired physiological change or disorder. Beneficial or desired clinical results include, but are not limited to, alleviation of symptoms, diminishment of extent of disease (e.g., decrease of tumor size, tumor burden, or tumor distribution), stabilized (i.e., not worsening) state of disease, delay or slowing of disease progression, amelioration or palliation of the disease state, and remission (whether partial or total), whether detectable or undetectable. "Treatment" can also mean prolonging survival, as compared to expected survival if not receiving treatment. Those in need of treatment include those already with the condition or disorder as well as those prone to have the condition or disorder or those in which the condition or disorder is to be prevented.

Administration "in combination with" one or more further therapeutic agents includes simultaneous (concurrent) and consecutive administration in any order.

The term "identical," as used herein, refers to two or more sequences or subsequences that are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75 to about 100 nucleic acids in length, over a region that is about 50 nucleic acids in length, or, where not specified, across the entire sequence of a polynucleotide sequence.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "subject," or "patient", as used herein, refers to a vertebrate. In certain embodiments, the vertebrate is a mammal. Mammals include, but are not limited to, humans, non-human primates, farm animals (such as cows), sport animals, and pets (such as cats, dogs, and horses). In certain embodiments, a mammal is a human.

The term "therapeutically effective amount," as used herein, refers to the amount of a composition containing the expanded cell populations and/or admixtures of the present invention administered to a subject, e.g., a human patient, already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

The term antigen presenting cell (APC) refers to a wild-type APC, or an engineered or artificial antigen presenting cell (aAPC). APCs can be provided as an irradiated population of APCs. APCs can be provided from a immortalized cell line (e.g., K562 or an engineered aAPC derived from an immortalized cell line) or as a fraction of cells from a donor (e.g., PBMCs).

As used herein, the terms "structurally different" and "structurally distinct," in reference to a protein or polypeptide fragment thereof, such as an antibody or an epitope, refer to a covalent (i.e., structural) difference between at least two different proteins, polypeptide fragments thereof, or epitopes. For example, two structurally different proteins (e.g., antibodies) can refer to two proteins that have different primary amino acid sequences. In some cases, structurally different activating agents bind structurally different epitopes, such as epitopes having a different primary amino acid sequence.

As used herein, the term "anti-tumor cytotoxicity" that is "independent of" a specified receptor activity (e.g., NKp30 activity, NKp44 activity, and/or NKp46 activity), refers to anti-tumor cytotoxicity that is exhibited whether or not the specified receptor or specified combination of receptors is expressed by the cell or is functional to mediate cytolysis. As such, a γδ T cell that exhibits anti-tumor cytotoxicity that is independent of NKp30 activity, NKp44 activity, and/or NKp46 activity can also exhibit NKp30 activity-dependent anti-tumor cytotoxicity, NKp44 activity-dependent anti-tumor cytotoxicity, and/or NKp46 activity-dependent anti-tumor cytotoxicity.

As used herein, the terms "NKp30 activity-dependent anti-tumor cytotoxicity," "NKp44 activity-dependent anti-tumor cytotoxicity," and "NKp46 activity-dependent anti-tumor cytotoxicity" refer to anti-tumor cytotoxicity that requires functional expression of the specified receptor. The presence or absence of such receptor dependent anti-tumor cytotoxicity can be determined by performing standard in vitro cytotoxicity assays in the presence or absence of an antagonist to the specified receptor. For example, presence or absence of NKp30 activity-dependent anti-tumor cytotoxicity can be determined by comparing the results of an in vitro cytotoxicity assays in the presence of an anti-NKp30 antagonist to the results obtained in the absence of an anti-NKp30 antagonist.

As used herein, a γδ T-cell population that comprises anti-tumor cytotoxicity, wherein at least a specified "%" of the anti-tumor cytotoxicity is "independent of" a specified receptor activity (e.g., NKp30 activity, NKp44 activity, and/or NKp46 activity), refers to a cell where blocking specified receptor reduces measured anti-tumor cytotoxicity by no more than the numerical % value. Thus, a γδ T-cell population that comprises anti-tumor cytotoxicity, wherein at least 50% of the anti-tumor cytotoxicity is independent of NKp30 activity would exhibit a reduction of 50% or less of in vitro anti-tumor cytotoxicity in the presence of an NKp30 antagonist as compared to in the absence of the NKp30 antagonist.

Overview

In humans, γδ T-cell(s) are a subset of T-cells that provide a link between the innate and adaptive immune responses. These cells undergo V-(D)-J segment rearrangement to generate antigen-specific γδ T-cell receptors (γδ TCRs), and γδ T-cell(s) and can be directly activated via the recognition of an antigen by either the γδ TCR or other, non-TCR proteins, acting independently or together to activate γδ T-cell effector functions. γδ T-cells represent a small fraction of the overall T-cell population in mammals, approximately 1-5% of the T-cells in peripheral blood and lymphoid organs, and they appear to reside primarily in epithelial cell-rich compartments like skin, liver, digestive, respiratory, and reproductive tracts. Unlike αβ TCRs, which recognize antigens bound to major histocompatibility complex molecules (MHC), γδ TCRs can directly recognize bacterial antigens, viral antigens, stress antigens expressed by diseased cells, and tumor antigens in the form of intact proteins or non-peptide compounds. δ3-08, δ3-20, δ3-23, δ3-31, δ3-42, δ3-47 and δ3-58 can activate and expand γδ T cells, and in some embodiments can be used to preferentially activate and expand δ3 γδ T cells, e.g., to clinically relevant levels. Without being bound by theory, different levels of activation and expansion of cultures originating from different donors may be due to the donor γδ variable TCR repertoire and the specificity of the antibody binding epitope. It has been discovered that not every agent which binds to specific γδ T-cell subsets is capable of activating the specific γδ T-cell and particularly activating and expanding the specific γδ T-cell population to clinically-relevant levels, i.e., >10⁸ target γδ T cells in an enriched culture. Similarly, not every binding epitope of a γδ T-cell population is an activating epitope, i.e., capable of activation of the specific γδ T-cell population upon binding.

The inventors of the present invention have identified specific γδ TCR binding regions associated with potent activation and expansion of the δ3 γδ T cell subtype. In some cases, the binding regions are within, or overlap with, a δ3 variable region. Thus, agents that bind these activating regions can be developed and used to selectively activate and expand the δ3 γδ T cell subtype. Exemplary activating agents are described herein. Thus, the present invention enables the specific activation and expansion of the δ3 γδ T cell subtype which produces clinically relevant levels of highly enriched δ3 γδ T-cell populations with increased purity, and admixtures thereof, that can be administered to patients. Such admixtures can include admixtures of other expanded γδ T cell subpopulations, such as δ1 and/or δ2 γδ T cells. Novel activating ligands, including antibodies, which specifically bind the activating epitopes capable of inducing enhanced activation and expansion of δ3 γδ T cell subtypes are also contemplated and further described herein. The activating ligands, methods, and compositions described herein can be used in combination with the activating ligands, methods, and compositions described in PCT/US17/32530, herein incorporated by reference in the entirety, to obtain and use expanded γδ T cell populations, and admixtures, and/or purified fractions thereof comprising essentially any desired proportion of δ1, δ2, δ3, δ4, and/or δ8 (e.g., δ1, δ2, and δ3) engineered or non-engineered γδ T cells by ex vivo expansion and/or post-expansion isolation. For example, one or more of the δ3 specific γδ T cell activating ligands described herein can be used in a culture medium in combination with one or more of the δ1 specific and/or δ2 specific γδ T cell activating ligands described in PCT/US17/32530 for ex vivo expansion. As another example, activating ligands, methods or compositions described herein can be used in a first or second ex vivo γδ T cell expansion step and activating ligands, methods or compositions described in PCT/US17/32530 can be used in a subsequent or previous ex vivo γδ T cell expansion step. Activating ligands can also be used for purification of specified γδ T cell populations by positive or negative selection.

In some cases, the production of clinically relevant levels (i.e., >10⁸) of γδ T cells using the methods of the present invention can be obtained with relatively small volumes of culture medium. For example, in some embodiments, the clinically relevant levels of γδ T cells can be obtained from expansion of a population of cells (e.g., an isolated mixed population of cells), in a final culture volume of approximately 25 L; 20 L; 10 L; 5 L; 3 L; 2 L; 1,500 mL; 1,000 mL; 500 mL; 200 mL; 150 mL; 100 mL, or less (e.g., from about 10 mL to about 100 mL, from about 100 mL to about 500 mL, from about 500 mL to about 5,000 mL, or from about 5 L to about 25 L). As another example, in some embodiments, the clinically relevant levels of γδ T cells can be obtained under conditions such that the expansion from an isolated mixed population of cells obtained from a donor, or multiple donors can be achieved using a total volume of culture media of less than about 50 L, 25 L, 20 L, 10 L, 5 L, 1 L, or 750 mL (e.g., about 750 mL to less than about 50 L, from about 100 mL to about 750 mL, from about 750 mL to about 5 L, from about 1 L to about 10 L, from about 10 L to about 50 L, or from about 10 L to about 25 L).

Described herein are methods for the selective activation and expansion of γδ T cell subtypes (e.g., δ3 γδ T cells) directly from isolated mixed cell populations, e.g., without prior depletion of non-target cell types, providing clinically-relevant levels of enriched γδ T cell population(s) having cytotoxic properties. Activating γδ variable TCR epitopes of specific γδ cell population(s) are also described. The present invention also provides methods of treatment with compositions comprising the enriched γδ T cell population(s) of the invention.

Described herein are methods of producing or providing clinically relevant levels (>10⁸) of engineered or non-engineered γδ T cells, including one or more specific subsets of γδ T cells (e.g., δ3 γδ T cells). Such methods can be used to produce such clinically relevant levels from a single donor, including from a single sample of a single donor. Moreover, such methods can be used to produce significantly greater than 10⁸ engineered or non-engineered γδ T cells. For example, in some embodiments about, or at least about, 10⁹, 10¹⁰, 10¹¹, or 10¹² engineered or non-engineered γδ T cells, including one or more specific subsets of γδ T cells (e.g., δ3 γδ T cells), can be produced in the methods described herein. In some cases, such population sizes can be achieved in as few as 14-30 days, 19-30 days, or 21-30 days, and/or with a total volume of culture media used of less than about 1 L.

Isolation of γδ T-Cells

In some aspects, the instant invention provides ex vivo methods for expansion of engineered or non-engineered γδ T cells. In some cases, the methods employ one or more (e.g., first and/or second) expansion steps that do not include a cytokine that favors expansion of a specific population of γδ T cells, such as IL-4, IL-2, or IL-15, or a combination thereof. In some embodiments, the instant invention provides ex vivo methods for producing enriched γδ T cell populations from isolated mixed cell populations, comprising contacting the mixed cell population with one or more agents which selectively expand δ3 T cells by binding to an epitope specific to a δ3 TCR (e.g., a δ3 γδ TCR) to provide an enriched γδ T cell population.

In other aspects, the present disclosure provides methods for the genetic engineering of γδ T cells that have been isolated from a subject. Methods of enrichment, activation, expansion, or genetic engineering can be performed singly or in combination, in any order. In one embodiment, γδ T cells can be isolated, genetically engineered, and then activated and expanded. In a preferred embodiment, γδ T cells can be isolated, the isolated cells can be directly activated and expanded, optionally purified, and then optionally genetically engineered. In some embodiments, such activated and expanded and then genetically engineered γδ T cells can be further activated and/or expanded and/or purified.

An, e.g., non-engineered, γδ T cell population can be expanded from a complex sample of a subject. A complex sample can be a peripheral blood sample (e.g., PBLs or PBMCs), a leukapheresis sample, a cord blood sample, a tumor, a stem cell precursor, a tumor biopsy, a tissue, a lymph, or from epithelial sites of a subject directly contacting the external milieu, or derived from stem precursor cells. In some cases, the present disclosure provides methods for selective expansion of Vδ3⁺ cells. In some cases, the present disclosure provides methods for expansion of Vδ3⁺ cells in combination with expansion of, Vδ1⁺ cells, Vδ2⁺ cells, Vδ1⁺ cells and Vδ3⁺ cells, Vδ1⁺ cells and Vδ4⁺ cells, Vδ1⁺ cells, Vδ3⁺ cells, Vδ4⁺ cells, and Vδ5⁺ cells, or any grouping thereof.

Peripheral blood mononuclear cells can be collected from a subject, for example, with an apheresis machine, including the Ficoll-Paque™ PLUS (GE Healthcare) system, or another suitable device/system. γδ T cell(s), or a desired subpopulation of γδ T cell(s), can be purified from the collected sample with, for example, flow cytometry techniques. Cord blood cells can also be obtained from cord blood during the birth of a subject. See WO 2016/081518, incorporated by reference herein in its entirety for all purposes including but not limited to methods and compositions for PBMC isolation, γδ T cell activation and expansion, and making and using γδ T cell activation agents.

A γδ T cell may be expanded from an isolated complex sample or mixed cell population that is cultured in vitro by contacting the mixed cell population with one or more agents which expand γδ T cell by specifically binding to an epitope of a δ3 γδ TCR to provide an enriched γδ T cell population, e.g., in a first enrichment step. In some embodiments, γδ T cells comprised in a whole PBMC population, without prior depletion of one or more specific cell populations such as one or more or all of the following non-γδ T cell monocytes: αβ T cells, B cells, and NK cells, can be activated and expanded, resulting in an enriched γδ T cell population. In some aspects, activation and expansion of γδ T cells are performed without the presence of native or engineered APCs. In some aspects, activation and expansion of γδ T cells are performed in the presence of native or engineered APCs. In some aspects, activation and expansion of γδ T cells are performed in the presence of native or engineered APCs in a first or second step, and activation and expansion are also performed in a step (first or second) without native or engineered APCs. In some aspects, isolation and expansion of γδ T cells from, e.g., tumor specimens, can be performed using immobilized γδ T cell mitogens, including antibodies specific to activating epitopes of a γδ TCR (e.g., δ3' TCR), and other activating agents, including lectins, which can, e.g., bind the activating epitopes of a γδ TCR provided herein.

In certain embodiments, the isolated mixed cell population is contacted with one or more agents which expand (e.g., selectively expand) δ3 γδ T cells for about, or at least about, 2 days, about 3 days, about 4 days, about 5 days, about 6 days, about 7 days, about 8 days, about 9 days, about 10 days, about 11 days, about 12 days, about 13 days, about 14 days, about 15 days, about 17 days, about 19 days, about 21 days, about 25 days, about 29 days, about 30 days, or any range therein. For example, the isolated mixed cell population is contacted with one or more agents which expand (e.g., selectively expand) δ3 γδ T cells for about 1 to about 4 days, about 2 to about 4 days, about 2 to about 5 days, about 3 to about 5 days, about 5 to about 21 days, about 5 to about 19 days, about 5 to about 15 days, about 5 to about 10 days, or about 5 to about 7 days, to provide a first enriched γδ T cell population. As another example, the isolated mixed cell population is contacted with one or more agents which expand (e.g., selectively expand) δ3 γδ T cells for about 7 to about 21 days, about 7 to about 19 days, about 7 to about 23 days, or about 7 to about 15 days to provide a first enriched γδ T-cell population.

In some cases, a purification or isolation step is performed between a first and second expansion step. In some cases, the isolation step includes removal of one or more activating agents. In some cases, the isolation step includes specific isolation of γδ T cells, or a subtype thereof (e.g., δ3 γδ T cells). In some cases, one or more (e.g., all) activating agents (e.g., all activating agents that are not common components of cell culture media such as serum components and/or IL-2)) are removed between first and second expansion steps, but γδ T-cells are not specifically isolated from other cell types (αβ T-cells). In some cases, one or more (e.g., all) soluble activating agents are removed between first and second expansion steps, but γδ T-cells are not specifically isolated from other cell types (αβ T-cells).

In some embodiments, following the activation and expansion of γδ T cells using activating agents which bind to an activating epitope of a γδ TCR, in a first enrichment step, and optionally a second enrichment step, the, e.g., first, enriched γδ T cell population(s) of the invention may be further enriched or purified using techniques known in the art to obtain a second or further enriched γδ T cell population(s) in a second, third, fourth, fifth, etc. enrichment step. For example, the, e.g., first, enriched γδ T cell population(s) may be depleted of αβ T cells, B cells and NK cells. Positive and/or negative selection of cell surface markers expressed on the collected γδ T cell(s) can be used to directly isolate a γδ T cell, or a population of γδ T cell(s) expressing similar cell surface markers from the, e.g., first, enriched γδ T-cell population(s). For instance, a γδ T cell can be isolated from an enriched γδ T cell population (e.g., after a first and/or second step of expansion) based on positive or negative expression of markers such as CD2, CD3, CD4, CD8, CD24, CD25, CD44, Kit, TCR α, TCR β, TCR γ (including one or more TCR γ sub-types), TCR δ (including one or more TCR δ sub-types), NKG2D, CD70, CD27, CD28, CD30, CD16, OX40, CD46, CD161, CCR7, CCR4, NKp30, NKp44, NKp46, DNAM-1, CD242, JAML, and other suitable cell surface markers.

In some embodiments, after a first step of expansion (e.g., after an isolation step performed subsequent to the first step of expansion), the expanded cells are, optionally diluted, and cultured in a second step of expansion. In preferred embodiments, the second step of expansion is performed under conditions in which culture media is replenished about every 1-2, 1-3, 1-4, 1-5, 2-5, 2-4, or 2-3 days in a second expansion step. In some embodiments, the second step of expansion is performed under conditions in which the cells are diluted or adjusted to a density that supports further γδ T cell expansion 1, 2, 3, 4, 5, 6, or more times. In some cases, the cell density adjustment is performed contemporaneously with (i.e., on the same day as, or at the same time as) replenishment of culture media. For example, cell density can be adjusted every 1-2, 1-3, 1-4, 1-5, 2-5, 2-4, or 2-3 days in a second expansion step. Typical cell densities that support further γδ T cell expansion include, but are not limited to, about $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$ cells/mL, $10\times10^6$ cells/mL, $15\times10^6$ cells/mL, $20\times10^6$ cells/mL, or $30\times10^6$ cells/mL of culture.

In some embodiments, cell density is adjusted to a density of from about $0.5\times10^6$ to about $1\times10^6$ cells/mL, from about $0.5\times10^6$ to about $1.5\times10^6$ cells/mL, from about $0.5\times10^6$ to about $2\times10^6$ cells/mL, from about $0.75\times10^6$ to about $1\times10^6$ cells/mL, from about $0.75\times10^6$ to about $1.5\times10^6$ cells/mL, from about $0.75\times10^6$ to about $2\times10^6$ cells/mL, from about $1\times10^6$ to about $2\times10^6$ cells/mL, or from about $1\times10^6$ to about $1.5\times10^6$ cells/mL, from about $1\times10^6$ to about $2\times10^6$ cells/mL, from about $1\times10^6$ to about $3\times10^6$ cells/mL, from about $1\times10^6$ to about $4\times10^6$ cells/mL, from about $1\times10^6$ to about $5\times10^6$ cells/mL, from about $1\times10^6$ to about $10\times10^6$ cells/mL, from about $1\times10^6$ to about $15\times10^6$ cells/mL, from about $1\times10^6$ to about $20\times10^6$ cells/mL, or from about $1\times10^6$ to about $30\times10^6$ cells/mL.

In some embodiments, the second step of expansion is performed under conditions in which the cells are monitored and maintained at a predetermined cell density (or density interval) and/or maintained in culture medium having a predetermined glucose content. For example, the cells can be maintained at a viable cell density of from about $0.5 \times 10^6$ to about $1 \times 10^6$ cells/mL, from about $0.5 \times 10^6$ to about $1.5 \times 10^6$ cells/mL, from about $0.5 \times 10^6$ to about $2 \times 10^6$ cells/mL, from about $0.75 \times 10^6$ to about $1 \times 10^6$ cells/mL, from about $0.75 \times 10^6$ to about $1.5 \times 10^6$ cells/mL, from about $0.75 \times 10^6$ to about $2 \times 10^6$ cells/mL, from about $1 \times 10^6$ to about $2 \times 10^6$ cells/mL, or from about $1 \times 10^6$ to about $1.5 \times 10^6$ cells/mL, from about $1 \times 10^6$ to about $3 \times 10^6$ cells/mL, from about $1 \times 10^6$ to about $4 \times 10^6$ cells/mL, from about $1 \times 10^6$ to about $5 \times 10^6$ cells/mL, from about $1 \times 10^6$ to about $10 \times 10^6$ cells/mL, from about $1 \times 10^6$ to about $15 \times 10^6$ cells/mL, from about $1 \times 10^6$ to about $20 \times 10^6$ cells/mL, from about $1 \times 10^6$ to about $30 \times 10^6$ cells/mL.

In some cases, the cells can be maintained at a higher concentration for at least a portion of the expansion. For example, for a first portion of a first or second expansion, cells viability may be enhanced at a higher cell concentration. As another example, for a final portion of a first or second expansion culture volume may be most efficiently utilized at a higher cell concentration. Thus, in some embodiments, cells can be maintained at a viable cell density of from about $1 \times 10^6$ cells/mL to about $20 \times 10^6$ cells/mL for at least a portion of a first or second expansion culture or all of a first or second expansion culture.

As another example, the cells can be maintained in culture medium having a glucose content of from about 0.5 g/L to about 1 g/L, from about 0.5 g/L to about 1.5 g/L, from about 0.5 g/L to about 2 g/L, from about 0.75 g/L to about 1 g/L, from about 0.75 g/L to about 1.5 g/L, from about 0.75 g/L to about 2 g/L, from about 1 g/L to about 1.5 g/L, from about 1 g/L to about 2 g/L, from 1 g/L to 3 g/L, or from 1 g/L to 4 g/L. In some embodiments, the cells can be maintained in culture medium having a glucose content of about 1.25 g/L. In some cases, such as where a high cell density culture is maintained, cells can be maintained in culture medium having a glucose content of about 1 g/L to about 5 g/L, from about 1 g/L to about 4 g/L, from about 2 g/L to about 5 g/L, or from about 2 g/L to about 4 g/L.

Typically glucose content is maintained by addition of fresh serum containing or serum free culture medium to the culture. In some embodiments, the cells can be maintained at a predetermined viable cell density interval and in a culture medium having a predetermined glucose content interval, e.g., by monitoring each parameter and adding fresh media to maintain the parameters within the predetermined limits. In some embodiments, glucose content is maintained by adding fresh serum containing or serum free culture medium in the culture while removing spent medium in a perfusion bioreactor while retaining the cells inside. In some embodiments, additional parameters including, without limitation, one or more of: pH, partial pressure of $O_2$, $O_2$ saturation, partial pressure of $CO_2$, $CO_2$ saturation, lactate, glutamine, glutamate, ammonium, sodium, potassium, and calcium, are monitored and/or maintained during a γδ T cell expansion (e.g., selective γδ T cell expansion) or during a first or second step of γδ T cell expansion (e.g., selective γδ T cell expansion) described herein.

A δ3 γδ T cell population may be selectively expanded from an isolated complex sample or mixed cell population that is cultured in vitro by contacting the mixed cell population with one or more agents which selectively expand δ3 T-cells by specifically binding to an epitope of a δ3 TCR to provide an enriched γδ T-cell population, e.g., in a first enrichment step. In some cases, the one or more agents specifically bind to a δ3J1, δ3J2, or δ3J3 TCR, δ3J4 TCR, or two thereof, or three thereof, or all thereof.

In some embodiments, δ3 γδ cells in a whole PBMC population, without prior depletion of specific cell populations such as monocytes, αβ T cells, B cells, and NK cells, can be activated and expanded, resulting in an enriched γδ T cell population (e.g., an enriched δ3 γδ T cell population). In some aspects, activation and expansion of δ3 γδ T cells are performed without the presence of native or engineered APCs. In some aspects, isolation and expansion of γδ T cells from tumor specimens can be performed using immobilized γδ T cell mitogens, including antibodies specific to activating epitopes specific to a δ3 TCR; a δ1 TCR; a δ1, δ3, δ4, and δ5 TCR, a δ1 and δ4 TCR; or a δ2 TCR, and other activating agents, including lectins, which, e.g., bind the activating epitopes specific to a δ3 TCR; a δ1 TCR; a δ1, δ3, δ4 and δ5 TCR; a δ1 and δ4 TCR; or a δ2 TCR provided herein.

In certain embodiments, the isolated mixed cell population is contacted with one or more agents which selectively expand δ3 T cells for about 5 days, 6 days, about 7 days, about 8 days, about 9 days, about 10 days, about 11 days, about 12 days, about 13 days, about 14 days, about 15 days, or any range therein. For example, the isolated mixed cell population is contacted with one or more agents which selectively expand δ3 T cells for about 1 to about 3 days, about 1 to about 4 days, about 1 to about 5 days, about 2 to about 3 days, about 2 to about 4 days, about 2 to about 5 days, about 3 to about 4 days, about 3 to about 5 days, about 4 to about 5 days, about 5 to about 15 days, or about 5 to about 7 days, to provide a first enriched γδ T-cell population. In some embodiments selectively expanded γδ T cells are further expanded in a second step of expansion as described herein.

In certain embodiments, the starting isolated mixed cell population, e.g., peripheral blood sample, comprises T lymphocytes in the range of about 20-80%. In certain embodiments, the percent of residual αβ T cells and NK cells in enriched γδ T-cell population(s) of the invention is about, or less than about, 2.5% and 1%, respectively. In certain embodiments, the percent of residual αβ T cells or NK cells in enriched γδ T-cell population(s) of the invention is about, or less than about, 1%, 0.5%, 0.4%, 0.2%, 0.1%, or 0.01%. In certain embodiments, the percent of residual αβ T cells in enriched γδ T cell population(s) of the invention is about, or less than about, 0.4%, 0.2%, 0.1%, or 0.01% (e.g., after a step of positive selection for γδ T cells or a sub-type thereof such as δ3 γδ T cells or after depletion of αβ T cells). In some embodiments, αβ T cells are depleted, but NK cells are not depleted before or after a first and/or second γδ T-cell expansion. In certain aspects, the isolated mixed cell population is derived from a single donor. In other aspects, the isolated mixed cell population is derived from more than one donor or multiple donors (e.g., 2, 3, 4, 5, or from 2-5, 2-10, or 5-10 donors, or more).

As such, in some embodiments, the methods of the present invention can provide a clinically relevant number ($>10^8$, $>10^9$, $>10^{10}$, $>10^{11}$, or $>10^{12}$, or from about $10^8$ to about $10^{12}$) of expanded γδ T-cells from as few as one donor. In some cases, the methods of the present invention can provide a clinically relevant number ($>10^8$, $>10^9$, $>10^{10}$, $>10^{11}$, or $>10^{12}$, or from about $10^8$ to about $10^{12}$) of expanded γδ T-cells within less than 19, 21, or 30 days from the time of obtaining a donor sample.

Following the specific activation and expansion of the specific γδ T cell subsets using activating agents which bind to an activating epitope specific to a δ3 TCR, in a first enrichment step, the first enriched γδ T cell population(s) of the invention may be further enriched or purified using techniques known in the art to obtain a second or further enriched γδ T cell population(s) in a second, third, fourth, fifth, etc. enrichment step. For example, the first enriched γδ T cell population(s) may be depleted of αβ T cells, B cells and/or NK cells. Positive and/or negative selection of cell surface markers expressed on the collected γδ T cell(s) can be used to directly isolate a γδ T cell, or a population of γδ T cell(s) expressing similar cell surface markers from the first enriched γδ T cell population(s). For instance, a γδ T cell can be isolated from a first enriched γδ T cell population based on positive or negative expression of markers such as CD2, CD3, CD4, CD8, CD24, CD25, CD44, Kit, TCR α, TCR β, TCR γ (or one or more subtypes thereof), TCR δ (or one or more subtypes thereof), NKG2D, CD70, CD27, CD28, CD30, CD16, OX40, CD46, CD161, CCR7, CCR4, DNAM-1, JAML, and other suitable cell surface markers.

In some embodiments, following the first γδ T cell expansion, first enrichment step, second γδ T-cell expansion, and/or second enrichment step, of the invention, the enriched γδ T cell population comprises clinically-relevant levels of γδ T cell subsets of $>10^8$ cells, e.g., in a culture volume of less than 10 mL, 25 mL, 50 mL, 100 mL, 150 mL, 200 mL, 500 mL, 750 mL, 1 L, 2 L, 3 L, 4 L, 5 L, 10 L, 20 L, or 25 L. For example, the methods of the present invention can provide clinically-relevant levels of γδ T cell subsets of $>10^8$ cells in an expansion culture having a volume of from 10-100 mL; from 25-100 mL; from 50-100 mL; from 75-100 mL; from 10-150 mL; from 25-150 mL; from 50-150 mL; from 75-150 mL; from 100-150 mL; from 10-200 mL; from 25-200 mL; from 50-200 mL; from 75-200 mL, from 100-200 mL; from 10-250 mL; from 25-250 mL; from 50-250 mL; from 75-250 mL, from 100-250 mL; from 150-250 mL; from 5-1,000 mL; from 10-1,000 mL, or from 100-1,000 mL; from 150-1,000 mL; from 200-1,000 mL; from 250-1,000 mL, 400 mL to 1 L, 1 L to 2 L, 2 L to 5 L, 2 L to 10 L, 4 L to 10 L, 4 L to 15 L, 4 L to 20 L, or 4 L to 25 L. In other embodiments, following the second, third, fourth, fifth, etc. enrichment step of the invention, the enriched γδ T-cell population comprises clinically-relevant levels $>10^8$ of one or more γδ T cell subsets (e.g., $>10^8$ δ3 γδ T cells).

In some embodiments, γδ T cell(s) can rapidly expand in response to contact with one or more antigens. Some γδ T cell(s), such as Vγ9Vδ2$^+$ γδ T cell(s) rapidly expand in vitro in response to contact with some antigens, like prenyl-pyrophosphates, alkyl amines, and metabolites or microbial extracts during tissue culture. In addition, some wild-type γδ T cell(s), such as Vγ2Vδ2+γδ T cell(s) rapidly expand in vivo in humans in response to certain types of vaccination(s). Stimulated γδ T cells can exhibit numerous antigen-presentation, co-stimulation, and adhesion molecules that can facilitate the isolation of a γδ T-cell(s) from a complex sample. A γδ T-cell(s) within a complex sample can be stimulated in vitro with at least one antigen for 1 day, 2 days, 3 days, 4 days, 5 days, 6 days, 7 days, about 5-15 days, 5-10 days, or 5-7 days, or another suitable period of time, e.g., in combination with, before, or after expansion with a selective γδ T-cell expansion agent described herein such as an antibody or an immobilized antibody. Stimulation of the γδ T cell with a suitable antigen can expand the γδ T cell population ex vivo or in vitro.

Non-limiting examples of antigens that may be used to stimulate the expansion of γδ T-cell(s) from a complex sample in vitro include, prenyl-pyrophosphates, such as isopentenyl pyrophosphate (IPP), alkyl-amines, metabolites of human microbial pathogens, metabolites of commensal bacteria, -methyl-3-butenyl-1-pyrophosphate (2M3B1PP), (e)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

Activation and expansion of γδ T-cells can be performed using activation and co-stimulatory agents described herein to trigger specific γδ T cell proliferation and persistent populations. In some embodiments, activation and expansion of γδ T cells from different cultures can achieve distinct clonal or mixed polyclonal population subsets by using different culture conditions such as different activating agents or mixtures thereof. In some cases, the distinct populations subsets can be purified and/or admixed to produce additional clonal or mixed polyclonal population subsets. In some embodiments, different agonist agents can be used to identify agents that provide specific γδ T cell activating signals. In one aspect, agents that provide specific γδ T cell activating signals can be different monoclonal antibodies (MAbs) directed against the γδ TCRs.

In one aspect, the MAbs can bind to different epitopes on the constant or variable regions of δ TCR and/or γ TCR. In one aspect, the MAbs can include pan γδ TCR MAbs. In one aspect, the pan γδ TCR MAbs may recognize domains shared by different γ and δ TCRs on either the γ or δ chain or both, including δ3$^+$ cell populations. In one aspect, the antibodies may be 5A6.E9 (Thermo scientific), B1 (Biolegend), IMMU510 and/or 11F2 (11F2) (Beckman Coulter). In one aspect, the MAbs can be directed to specific domains unique to the variable regions of the γ chain (7A5 Mab, directed to Vγ9 TCR (Thermo Scientific #TCR1720)), or domains on Vδ1 variable region (Mab TS8.2 (Thermo scientific #TCR1730; MAb TS-1 (ThermoFisher #TCR 1055), MAb R9.12 (Beckman Coulter #IM1761)), or Vδ2 chain (MAb 15D (Thermo Scientific #TCR1732 or Life technologies #TCR2732) B6 (Biolegend #331402), one or more of the δ1-#antibodies described in PCT/US17/32530, one or more of the δ2-#antibodies described in PCT/US17/32530, or one or more of δ3-08, δ3-20, δ3-23, δ3-31, δ3-42, δ3-47 and δ3-58.

In some embodiments, antibodies against different domains of the γδ TCR (pan antibodies and antibodies recognizing specific variable region epitopes on subset populations) can be combined to evaluate or make use of their ability to enhanced activation and expansion of γδ T cells and/or one or more subpopulations thereof. In some embodiments, γδ T cell activators can include γδ TCR-binding agents such as MICA, an agonist antibody to NKG2D, an, e.g., Fc tag, fusion protein of MICA, ULBP1, or ULBP3 (R&D systems Minneapolis, MN) ULBP2, or ULBP6 (Sino Biological Beijing, China). In some embodiments, companion co-stimulatory agents to assist in triggering specific γδ T cell proliferation without induction of cell anergy and apoptosis can be identified or used in the methods and compositions of the present invention. These co-stimulatory agents can include ligands to receptors expressed on γδ cells, such as ligand(s) to one or more of the following: NKG2D, CD161, CD70, JAML, DNAX, CD81 accessory molecule-1 (DNAM-1) ICOS, CD27, CD196, CD137, CD30, HVEM, SLAM, CD122, DAP, and CD28. In some aspects, co-stimulatory agents can be antibodies specific to unique epitopes on CD2 and CD3 molecules. CD2 and CD3 can have different conformation structures when expressed on αβ or γδ T cells (s), and in some cases, specific antibodies to CD3 and CD2 can lead to selective activation and expansion of γδ T-cells.

A population of γδ T cells (e.g., a population comprising δ3 γδ T cells) may be expanded ex vivo prior to engineering of the γδ T cells. Non-limiting example of reagents that can be used to facilitate the expansion of a γδ T cell population in vitro include anti-CD3 or anti-CD2, anti-CD27, anti-CD30, anti-CD70, anti-OX40 antibodies, IL-2, IL-4, IL-7, IL-9, IL-12, IL-15, IL-18, IL-19, IL-21, IL 23, IL-33, IFNγ, granulocyte-macrophage colony stimulating factor (GM-CSF), granulocyte colony stimulating factor (G-CSF), CD70 (CD27 ligand), concavalin A (ConA), pokeweed (PWM), protein peanut agglutinin (PNA), soybean agglutinin (SBA), Les *Culinaris* Agglutinin (LCA), *Pisum Sativum* Agglutinin (PSA), *Helix pomatia* agglutinin (HPA), *Vicia graminea* Lectin (VGA), *Phaseolus Vulgaris* Erythroagglutinin (PHA-E), *Phaseolus Vulgaris* Leucoagglutinin (PHA-L), *Sambucus Nigra* Lectin (SNA, EBL), *Maackia Amurensis*, Lectin II (MAL II), *Sophora Japonica* Agglutinin (SJA), *Dolichos Biflorus* Agglutinin (DBA), *Lens Culinaris* Agglutinin (LCA), *Wisteria Floribunda* Lectin (WFA, WFL) or another suitable mitogen capable of stimulating T cell proliferation.

Genetic engineering of the γδ T cell(s) may comprise stably integrating a construct expressing a tumor recognition moiety, such as an αβ TCR, a γδ TCR, a CAR encoding an antibody, an antigen binding fragment thereof, and/or a lymphocyte activation domain into the genome of the isolated γδ T-cells, a cytokine (e.g., IL-15, IL-12, IL-2, IL-7, IL-21, IL-18, IL-19, IL-33, IL-4, IL-9, IL-23, or IL-1) to enhance T-cell proliferation, survival, and function ex vivo and in vivo. Genetic engineering of the isolated γδ T-cell may also comprise deleting or disrupting gene expression from one or more endogenous genes in the genome the isolated γδ T-cell, such as the NMC locus (loci).

Ex-Vivo Expansion of γδ T-Cells

In other aspects, the present disclosure provides methods for the ex vivo expansion of a population of non-engineered and engineered γδ T cells for adoptive transfer therapy. A non-engineered or engineered γδ T cell of the disclosure may be expanded ex vivo. A non-engineered or engineered γδ T cell of the disclosure can be expanded in vitro without activation by APCs, or without co-culture with APCs and/or aminophosphonates. Additionally, or alternatively, a non-engineered or engineered γδ T cell of the disclosure can be expanded in vitro with at least one expansion step that includes activation by or co-culture with APCs and/or with one or more aminophosphonates.

In some embodiments, a non-engineered or engineered γδ T cell of the disclosure can be expanded in vitro without activation by APC in a first γδ T cell expansion, and then expanded in vitro with activation by APC in a second γδ T ell expansion. In some cases, the first γδ T cell expansion includes contacting the γδ T cells with one or more agents which (a) expand γδ T cells, or (b) selectively expand δ3 T cells by binding to an activating epitope specific to a δ3 TCR.

In some cases, the second γδ T cell expansion is performed in a culture medium that is free of the one or more agents used in the first γδ T cell expansion, or free of one of the one or more agents used in the first γδ T cell expansion. In some cases, the second γδ T cell expansion is performed in a culture medium that contains one or more second agents that (a) expand T cells, (b) selectively expand γδ T cells (e.g., compared to αβ T cells, B cells, or NK cells), or (c) selectively expand δ3 T cells by binding to an activating epitope specific to a δ3 TCR.

In some cases, the second agents are different (e.g., have a different primary amino acid sequence and/or bind a structurally different γδ TCR epitope) as compared to the agents used in the first γδ T cell expansion. In some cases, the second agents bind an overlapping γδ TCR epitope, the same γδ TCR epitope, or can compete for binding to γδ TCR with one or more of the agents used in the first γδ T-cell expansion. In some cases, the second agents are expressed on the cell surface of an APC. In some cases, the second agents are bound to the surface of an APC, e.g., by a binding interaction between a constant region of the second agent and an Fc-receptor on the surface of the APC. In some cases, the second agents are soluble. In some cases, the second γδ T cell expansion is performed in a culture medium containing soluble second agents and APCs, optionally wherein the APC express on their cell surface or bind to their cell surface an agent that expands or selectively expands a γδ T cell population. The soluble second agents and the agent expressed on the surface or bound to the surface of the APC can be the same or different, e.g., bind the same or different epitope on a γδ TCR.

In some cases, the first γδ T cell expansion is performed without an APC, and the second γδ T cell expansion is performed with an APC. In some cases, the second γδ T cell expansion is performed with an APC and one or more second agents that (a) expand T cells, (b) selectively expand γδ T cells, or (c) selectively expand δ3 T cells by binding to an activating epitope specific to a δ3 TCR.

One of skill in the art will appreciate that, in certain embodiments, the methods of the second expansion step described herein can be performed as a first expansion step and methods of the first step described herein can be performed as a second expansion step. As an example, and without limitation, in some embodiments, a mixed population of cells (e.g., PBMC) can be expanded by contacting with an APC in a first step, and then expanded in the absence of an APC, e.g., by contacting the expanded population from the first expansion step with an immobilized agent that selectively expands δ3 T-cells by binding to an activating epitope specific to a δ3 TCR. In some embodiments, a method of the invention can expand various γδ T cell populations, such as a Vγ1$^+$, a Vγ2$^+$, or Vγ3$^+$ γδ T-cell population.

In some instances, a γδ T cell population can be expanded in vitro in fewer than 36 days, fewer than 35 days, fewer than 34 days, fewer than 33 days, fewer than 32 days, fewer than 31 days, fewer than 30 days, fewer than 29 days, fewer than 28 days, fewer than 27 days, fewer than 26 days, fewer than 25 days, fewer than 24 days, fewer than 23 days, fewer than 22 days, fewer than 21 days, fewer than 20 days, fewer than 19 days, fewer than 18 days, fewer than 17 days, fewer than 16 days, fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, or fewer than 3 days.

In some aspects, provided are methods for selectively expanding various γδ T cells, including engineered and non-engineered γδ T cells by contacting the γδ T cells from the mixed cell population with an activation agent. In some cases, the activation agent binds to a specific epitope on a cell-surface receptor of a γδ T cell. The activation agent can be an antibody, such as a monoclonal antibody. The activation agent, or combinations thereof, can specifically activate the expansion of one or more types of γδ T-cells, such δ3, δ2, δ1, δ1 and δ4, or δ1 and δ3 cell populations. In some embodiments the activation agent specifically activates the expansion of δ3 cell populations to provide an enriched δ3 T cell population.

An activation agent may stimulate the expansion of engineered and non-engineered γδ T cells (e.g., δ3 γδ T cells) at a fast rate of growth. For instance, an agent can stimulate an expansion of the γδ T-cell population at a mean rate of 1 cell division in less than 30 hours, 1 cell division in less than 29 hours, 1 cell division in less than 28 hours, 1 cell division in less than 27 hours, 1 cell division in less than 26 hours, 1 cell division in less than 25 hours, 1 cell division in less than 24 hours, 1 cell division in less than 23 hours, 1 cell division in less than 22 hours, 1 cell division in less than 21 hours, 1 cell division in less than 20 hours, 1 cell division in less than 19 hours, 1 cell division in less than 18 hours, 1 cell division in less than 17 hours, 1 cell division in less than 16 hours, 1 cell division in less than 15 hours, 1 cell division in less than 14 hours, 1 cell division in less than 13 hours, 1 cell division in less than 12 hours, 1 cell division in less than 11 hours, 1 cell division in less than 10 hours, 1 cell division in less than 9 hours, 1 cell division in less than 8 hours, 1 cell division in less than 7 hours, 1 cell division in less than 6 hours, 1 cell division in less than 5 hours, 1 cell division in less than 4 hours, 1 cell division in less than 3 hours, 1 cell division in less than 2 hours. In some cases, the fast rate of expansion can be maintained for at least about 8 hours of culture (e.g., 8 to 24 hours, or 1-3, 1-4, 1-8, 2-3, 2-4, or 2-8 days, or less than about 19, 21, or 30 days).

In some cases, an activation agent may stimulate the expansion of engineered and non-engineered γδ T cells (e.g., δ3 γδ T cells) at a mean rate of about 1 division per about 4 hours, a mean rate of about 1 division per about 5 hours, a mean rate of about 1 division per about 6 hours, a mean rate of about 1 division per about 7 hours, a mean rate of about 1 division per about 8 hours, a mean rate of about 1 division per about 9 hours, a mean rate of about 1 division per about 10 hours, a mean rate of about 1 division per about 11 hours, a mean rate of about 1 division per about 12 hours, a mean rate of about 1 division per about 13 hours, a mean rate of about 1 division per about 14 hours, a mean rate of about 1 division per about 15 hours, a mean rate of about 1 division per about 16 hours, a mean rate of about 1 division per about 17 hours, a mean rate of about 1 division per about 18 hours, a mean rate of about 1 division per about 19 hours, a mean rate of about 1 division per about 20 hours, a mean rate of about 1 division per about 21 hours, a rate of about 1 division per about 22 hours, a rate of about 1 division per about 23 hours, a mean rate of about 1 division per about 24 hours, a mean rate of about 1 division per about 25 hours, a mean rate of about 1 division per about 26 hours, a mean rate of about 1 division per about 27 hours, a rate of about 1 division per about 28 hours, a rate of about 1 division per about 29 hours, a mean rate of about 1 division per about 30 hours, a mean rate of about 1 division per about 31 hours, a mean rate of about 1 division per about 32 hours, a mean rate of about 1 division per about 33 hours, a rate of about 1 division per about 34 hours, a rate of about 1 division per about 35 hours, a mean rate of about 1 division per about 36 hours. In some cases, the fast rate of expansion can be maintained for at least about 8 hours of culture (e.g., 8 to 24 hours, or 1-3, 1-4, 1-8, 2-3, 2-4, or 2-8 days, or less than about 19, 21, or 30 days).

In some cases, an activation agent may stimulate the rapid expansion of engineered and/or non-engineered γδ T cells (e.g., δ3 γδ T cells) in a γδ T cell expansion culture (e.g., δ3 γδ T cell expansion culture), wherein the rapid expansion is at any one of the foregoing mean rates of cell division and is maintained for between about 1 contiguous day and about 19 contiguous days, between about 1 contiguous day and about 14 contiguous days, between about 1 contiguous day and about 7 contiguous days, between about 1 contiguous day and about 5 contiguous days, between about 2 contiguous days and about 19 contiguous days, between about 2 contiguous days and about 14 contiguous days, between about 2 contiguous days and about 7 contiguous days, between about 2 contiguous days and about 5 contiguous days, between about 4 contiguous days and about 19 contiguous days, between about 4 contiguous days and about 14 contiguous days, between about 4 contiguous days and about 7 contiguous days, or between about 4 contiguous days and about 5 contiguous days.

In some cases, an activation agent may stimulate the expansion of engineered and/or non-engineered γδ T cells (e.g., δ3 γδ T cells) in a γδ T cell expansion culture (e.g., δ3 γδ T cell expansion culture) that has been maintained for between about 2 and about 7 contiguous days, or between about 2 and about 5 contiguous days, at a mean rate of about 1 division per about 12 hours (e.g., 10-12 hours), a mean rate of about 1 division per about 13 hours (e.g., 10-13 hours), a mean rate of about 1 division per about 14 hours (e.g., 10-14 hours), a mean rate of about 1 division per about 15 hours (e.g., 10-15 hours), a mean rate of about 1 division per about 16 hours (e.g., 10-16 hours), a mean rate of about 1 division per about 17 hours (e.g., 10-17 hours or 12-17 hours), a mean rate of about 1 division per about 18 hours (e.g., 10-18 hours or 12-18 hours), a mean rate of about 1 division per about 19 hours (e.g., 10-19 hours or 12-19 hours), a mean rate of about 1 division per about 20 hours (e.g., 12-20 hours, 16-20 hours or 18-20 hours), a mean rate of about 1 division per about 21 hours (e.g., 12-21 hours, 16-21 hours or 18-21 hours), a rate of about 1 division per about 22 hours (e.g., 12-22 hours, 16-22 hours or 18-22 hours), a rate of about 1 division per about 23 hours or less (e.g., 12-23 hours, 16-23 hours or 18-23 hours), a mean rate of about 1 division per about 24 hours (e.g., 12-24 hours, 16-24 hours or 18-24 hours).

In some cases, an activation agent may stimulate the expansion of engineered and/or non-engineered γδ T cells (e.g., δ3 γδ T cells) in a γδ T cell expansion culture (e.g., δ3 γδ T cell expansion culture) that has been maintained for between about 2 and about 7 contiguous days, or between about 2 and about 5 contiguous days at a mean rate of about 1 division per about 25 hours (e.g., 12-25 hours, 16-25 hours 18-25 hours, or 20-25 hours), a mean rate of about 1 division per about 26 hours (e.g., 12-26 hours, 16-26 hours 18-26 hours, or 20-26 hours), a mean rate of about 1 division per about 27 hours (e.g., 12-27 hours, 16-27 hours 18-27 hours, or 20-27 hours), a rate of about 1 division per about 28 hours (e.g., 12-28 hours, 16-28 hours 18-28 hours, 20-28 hours, or 22-28 hours), a rate of about 1 division per about 29 hours (e.g., 16-29 hours 18-29 hours, 20-29 hours, or 22-29 hours), a mean rate of about 1 division per about 30 hours (e.g., 16-30 hours 18-30 hours, 20-30 hours, or 22-30 hours), a mean rate of about 1 division per about 31 hours (e.g., 16-31 hours 18-31 hours, 20-31 hours, 22-31 hours, or 24-31 hours), a mean rate of about 1 division per about 32 hours (e.g., 18-32 hours, 20-32 hours, 22-32 hours, or 24-32 hours), a mean rate of about 1 division per about 33 hours (e.g., 18-33 hours, 20-33 hours, 22-33 hours, or 24-33 hours), a rate of about 1 division per about 34 hours (e.g., 18-34 hours, 20-34 hours, 22-34 hours, or 24-34 hours), a rate of about 1 division per about 35 hours (e.g., 18-35 hours, 20-35 hours, 22-35 hours, or 24-35 hours), a mean rate of about 1 division per about 36 hours (e.g., 18-36 hours, 20-36 hours, 22-36 hours, or 24-36 hours).

In some cases, an activation agent may stimulate the expansion of engineered and/or non-engineered γδ T cells (e.g., δ3 γδ T cells) in a γδ T cell expansion culture (e.g., δ3 γδ T cell expansion culture) that has been maintained for at least 14 contiguous days at a mean rate of about 1 division per about 12 hours (e.g., 10-12 hours), a mean rate of about 1 division per about 13 hours (e.g., 10-13 hours), a mean rate of about 1 division per about 14 hours (e.g., 10-14 hours), a mean rate of about 1 division per about 15 hours (e.g., 10-15 hours), a mean rate of about 1 division per about 16 hours (e.g., 10-16 hours), a mean rate of about 1 division per about 17 hours (e.g., 10-17 hours or 12-17 hours), a mean rate of about 1 division per about 18 hours (e.g., 10-18 hours or 12-18 hours), a mean rate of about 1 division per about 19 hours (e.g., 10-19 hours or 12-19 hours), a mean rate of about 1 division per about 20 hours (e.g., 12-20 hours, 16-20 hours or 18-20 hours), a mean rate of about 1 division per about 21 hours (e.g., 12-21 hours, 16-21 hours or 18-21 hours), a rate of about 1 division per about 22 hours (e.g., 12-22 hours, 16-22 hours or 18-22 hours), a rate of about 1 division per about 23 hours or less (e.g., 12-23 hours, 16-23 hours or 18-23 hours), a mean rate of about 1 division per about 24 hours (e.g., 12-24 hours, 16-24 hours or 18-24 hours).

In some cases, an activation agent may stimulate the expansion of engineered and/or non-engineered γδ T cells (e.g., δ3 γδ T cells) in a γδ T cell expansion culture that has been maintained for at least 14 contiguous days at a mean rate of about 1 division per about 25 hours (e.g., 12-25 hours, 16-25 hours 18-25 hours, or 20-25 hours), a mean rate of about 1 division per about 26 hours (e.g., 12-26 hours, 16-26 hours 18-26 hours, or 20-26 hours), a mean rate of about 1 division per about 27 hours (e.g., 12-27 hours, 16-27 hours 18-27 hours, or 20-27 hours), a rate of about 1 division per about 28 hours (e.g., 12-28 hours, 16-28 hours 18-28 hours, 20-28 hours, or 22-28 hours), a rate of about 1 division per about 29 hours (e.g., 16-29 hours 18-29 hours, 20-29 hours, or 22-29 hours), a mean rate of about 1 division per about 30 hours (e.g., 16-30 hours 18-30 hours, 20-30 hours, or 22-30 hours), a mean rate of about 1 division per about 31 hours (e.g., 16-31 hours 18-31 hours, 20-31 hours, 22-31 hours, or 24-31 hours), a mean rate of about 1 division per about 32 hours (e.g., 18-32 hours, 20-32 hours, 22-32 hours, or 24-32 hours), a mean rate of about 1 division per about 33 hours (e.g., 18-33 hours, 20-33 hours, 22-33 hours, or 24-33 hours), a rate of about 1 division per about 34 hours (e.g., 18-34 hours, 20-34 hours, 22-34 hours, or 24-34 hours), a rate of about 1 division per about 35 hours (e.g., 18-35 hours, 20-35 hours, 22-35 hours, or 24-35 hours), a mean rate of about 1 division per about 36 hours (e.g., 18-36 hours, 20-36 hours, 22-36 hours, or 24-36 hours).

In some cases, an activation agent may stimulate the expansion of engineered and/or non-engineered γδ T cells (e.g., δ3 γδ T cells) in a γδ T cell expansion culture that has been maintained for at least 19 contiguous days at a mean rate of about 1 division per about 12 hours (e.g., 10-12 hours), a mean rate of about 1 division per about 13 hours (e.g., 10-13 hours), a mean rate of about 1 division per about 14 hours (e.g., 10-14 hours), a mean rate of about 1 division per about 15 hours (e.g., 10-15 hours), a mean rate of about 1 division per about 16 hours (e.g., 10-16 hours), a mean rate of about 1 division per about 17 hours (e.g., 10-17 hours or 12-17 hours), a mean rate of about 1 division per about 18 hours (e.g., 10-18 hours or 12-18 hours), a mean rate of about 1 division per about 19 hours (e.g., 10-19 hours or 12-19 hours), a mean rate of about 1 division per about 20 hours (e.g., 12-20 hours, 16-20 hours or 18-20 hours), a mean rate of about 1 division per about 21 hours (e.g., 12-21 hours, 16-21 hours or 18-21 hours), a rate of about 1 division per about 22 hours (e.g., 12-22 hours, 16-22 hours or 18-22 hours), a rate of about 1 division per about 23 hours or less (e.g., 12-23 hours, 16-23 hours or 18-23 hours), a mean rate of about 1 division per about 24 hours (e.g., 12-24 hours, 16-24 hours or 18-24 hours).

In some cases, an activation agent may stimulate the expansion of engineered and/or non-engineered γδ T cells (e.g., δ3 γδ T cells) in a γδ T cell expansion culture (e.g., δ3 γδ T cell expansion culture) that has been maintained for at least 19 contiguous days at a mean rate of about 1 division per about 25 hours (e.g., 12-25 hours, 16-25 hours 18-25 hours, or 20-25 hours), a mean rate of about 1 division per about 26 hours (e.g., 12-26 hours, 16-26 hours 18-26 hours, or 20-26 hours), a mean rate of about 1 division per about 27 hours (e.g., 12-27 hours, 16-27 hours 18-27 hours, or 20-27 hours), a rate of about 1 division per about 28 hours (e.g., 12-28 hours, 16-28 hours 18-28 hours, 20-28 hours, or 22-28 hours), a rate of about 1 division per about 29 hours (e.g., 16-29 hours 18-29 hours, 20-29 hours, or 22-29 hours), a mean rate of about 1 division per about 30 hours (e.g., 16-30 hours 18-30 hours, 20-30 hours, or 22-30 hours), a mean rate of about 1 division per about 31 hours (e.g., 16-31 hours 18-31 hours, 20-31 hours, 22-31 hours, or 24-31 hours), a mean rate of about 1 division per about 32 hours (e.g., 18-32 hours, 20-32 hours, 22-32 hours, or 24-32 hours), a mean rate of about 1 division per about 33 hours (e.g., 18-33 hours, 20-33 hours, 22-33 hours, or 24-33 hours), a rate of about 1 division per about 34 hours (e.g., 18-34 hours, 20-34 hours, 22-34 hours, or 24-34 hours), a rate of about 1 division per about 35 hours (e.g., 18-35 hours, 20-35 hours, 22-35 hours, or 24-35 hours), a mean rate of about 1 division per about 36 hours (e.g., 18-36 hours, 20-36 hours, 22-36 hours, or 24-36 hours).

An activation agent may stimulate the expansion of sub-populations of engineered or non-engineered γδ T-cells at different rates of growth. For instance, an agent may stimulate the growth of a δ3 cell population at a faster rate such that over a period of time from 1 day to 90 days of culture (e.g., about 1 day to about 19, 21, or 23 days of culture) the expansion results in greater than about 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 50,000-fold, 70,000-fold, 100,000-fold or 1,000,000-fold expansion over another γδ T cell population, such as a δ1 or δ2 population; over a starting number of γδ T cells before the expansion; over a starting number of γδ3 T cells before the expansion; or over an αβ T cell population in the culture.

In some aspects, the disclosure provides an engineered or non-engineered γδ T cell population (e.g., δ3 γδ T cell population), in contact with an agent that stimulates an expansion of the γδ T cell population at a rapid rate, such as a rate of about 1 cell division per 30 hours or faster. In some cases, the agent selectively stimulates the proliferation of δ3

T cells. A γδ T cell population can comprise an amount of non-engineered γδ T-cells and an amount of engineered γδ T cells. In some cases, the γδ T cell population comprises different percentages of δ1, δ2, δ3, and/or δ4 T-cells. In some cases, the γδ T cell population comprises different percentages of δ1, δ2, δ3, and/or δ4 T-cells, contains more δ3 γδ T cells than any other γδ T cell subpopulation, and/or contains predominantly (>50%) δ3 γδ T cells. An engineered or non-engineered γδ T-cell population can comprise, for example, fewer than 90% δ3 T-cells, fewer than 80% δ3 T-cells, fewer than 70% δ3 T-cells, fewer than 60% δ3 T-cells, fewer than 50% δ3 T-cells, fewer than 40% δ3 T-cells, fewer than 30% δ3 T-cells, fewer than 20% δ3 T-cells, fewer than 10% δ3 T-cells, or fewer than 5% δ3 T-cells. Alternatively, an engineered or non-engineered γδ T-cell population can comprise greater than 5% δ3 T-cells, greater than 10% δ3 T-cells, greater than 20% δ3 T-cells, greater than 30% δ3 T-cells, greater than 40% δ3 T-cells, greater than 50% δ3 T-cells, greater than 60% δ3 T-cells, greater than 70% δ3 T-cells, greater than 80% δ3 T-cells, or greater than 90% δ3 T-cells. In some cases, the agent is one of the selective expansion agents described herein. In some cases, the agent is immobilized on a surface such as a cell culture surface, or a surface of an APC (e.g., expressed on the surface of the APC or bound to an Fc receptor expressed on the surface of the APC).

An engineered or non-engineered γδ T cell population can comprise, for example, fewer than 90% δ2 T-cells, fewer than 80% δ2 T-cells, fewer than 70% δ2 T-cells, fewer than 60% δ2 T-cells, fewer than 50% δ2 T-cells, fewer than 40% δ2 T-cells, fewer than 30% δ2 T-cells, fewer than 20% δ2 T-cells, fewer than 10% δ2 T-cells, or fewer than 5% δ2 T-cells. Alternatively, an engineered or non-engineered γδ T-cell population can comprise greater than 5% δ2 T-cells, greater than 10% δ2 T-cells, greater than 20% δ2 T-cells, greater than 30% δ2 T-cells, greater than 40% δ2 T-cells, greater than 50% δ2 T-cells, greater than 60% δ2 T-cells, greater than 70% δ2 T-cells, greater than 80% δ2 T-cells, or greater than 90% δ2 T-cells.

An engineered or non-engineered γδ T-cell population can comprise, for example, fewer than 90% δ1 and δ4 T-cells, fewer than 80% δ1 and δ4 T-cells, fewer than 70% δ1 and δ4 T-cells, fewer than 60% δ1 and δ4 T-cells, fewer than 50% δ1 and δ4 T-cells, fewer than 40% δ1 and δ4 T-cells, fewer than 30% δ1 and δ4 T-cells, fewer than 20% δ1 and δ4 T-cells, fewer than 10% δ1 and δ4 T-cells, or fewer than 5% δ1 and δ4 T-cells. Alternatively, an engineered or non-engineered γδ T-cell population can comprise greater than 5% δ1 and δ4 T-cells, greater than 10% δ1 and δ4 T-cells, greater than 20% δ1 and δ4 T-cells, greater than 30% δ1 and δ4 T-cells, greater than 40% δ1 and δ4 T-cells, greater than 50% δ1 and δ4 T-cells, greater than 60% δ1 and δ4 T-cells, greater than 70% δ1 and δ4 T-cells, greater than 80% δ1 and δ4 T-cells, or greater than 90% δ1 and δ4 T-cells.

An engineered or non-engineered γδ T-cell population can comprise, for example, fewer than 90% δ4 T-cells, fewer than 80% δ4 T-cells, fewer than 70% δ4 T-cells, fewer than 60% δ4 T-cells, fewer than 50% δ4 T-cells, fewer than 40% δ4 T-cells, fewer than 30% δ4 T-cells, fewer than 20% δ4 T-cells, fewer than 10% δ4 T-cells, or fewer than 5% δ4 T-cells. Alternatively, an engineered or non-engineered γδ T-cell population can comprise greater than 5% δ1 and δ4 T-cells, greater than 10% δ1 and δ4 T-cells, greater than 20% δ1 and δ4 T-cells, greater than 30% δ1 and δ4 T-cells, greater than 40% δ1 and δ4 T-cells, greater than 50% δ1 and δ4 T-cells, greater than 60% δ1 and δ4 T-cells, greater than 70% δ1 and δ4 T-cells, greater than 80% δ1 and δ4 T-cells, or greater than 90% δ1 and δ4 T-cells. An engineered or non-engineered γδ T-cell population can comprise, for example, fewer than 90% δ1 and δ4 T-cells, fewer than 80% δ1 and δ4 T-cells, fewer than 70% δ1 and δ4 T-cells, fewer than 60% δ1 and δ4 T-cells, fewer than 50% δ1 and δ4 T-cells, fewer than 40% δ1 and δ4 T-cells, fewer than 30% δ1 and δ4 T-cells, fewer than 20% δ1 and δ4 T-cells, fewer than 10% δ1 and δ4 T-cells, or fewer than 5% δ1 and δ4 T-cells.

In certain embodiments, the present invention provides admixtures of expanded γδ T-cell populations comprising 10-90% δ3 T-cells and 90-10% δ2 T-cells. In certain embodiments, the present invention provides admixtures of expanded γδ T-cell populations comprising 10-90% δ3 T-cells and 90-10% δ1 T-cells. In certain embodiments, the present invention provides admixtures of expanded γδ T-cell populations comprising 10-90% δ1 and δ3 T-cells and 90-10% δ2 T-cells. In certain embodiments, the present invention provides admixtures of expanded γδ T-cell populations comprising 10-90% δ3 and δ2 T-cells and 90-10% δ1 T-cells. In certain embodiments, the present invention provides admixtures of expanded γδ T-cell populations comprising 10-90% δ1, δ3, δ4 and δ5 T-cells and 90-10% δ2 T-cells.

One or more activation agent can contact the γδ T cells (for example an activator that binds a receptor on the surface of a γδ T cell, such as a γδ TCR) and thereafter a costimulatory molecule can contact the γδ T cells to provide further stimulation and to expand the γδ T cells. In some embodiments, the activation agent and/or costimulatory agent can be lectins of plant or non-plant origin, monoclonal antibodies that activate γδ T-cells, and other non-lectin/non-antibody agents. In other cases, the plant lectin can be concanavalin A (ConA) although other plant lectins such as may be used. Other examples of lectins include protein peanut agglutinin (PNA), soybean agglutinin (SBA), les culinaris agglutinin (LCA), Pisum sativum agglutinin (PSA), Helix pomatia agglutinin (HPA), Vicia graminea Lectin (VGA), Phaseolus Vulgaris Erythroagglutinin (PHA-E), Phaseolus Vulgaris Leucoagglutinin (PHA-L), Sambucus Nigra Lectin (SNA, EBL), Maackia Amurensis, Lectin II (MAL II), Sophora Japonica Agglutinin (SJA), Dolichos Biflorus Agglutinin (DBA), Lens Culinaris Agglutinin (LCA), and Wisteria Floribunda Lectin (WFA, WFL).

Non-limiting examples of activating agents and costimulatory molecules include any one or more antibodies selective for a δ or γ-chain or subtypes thereof described herein, antibodies such as 5A6.E9, B1, TS8.2, 15D, B6, B13, TS-1, 73.20, 7A5, IMMU510, R9.12, 11F2, or a combination thereof. Other examples of activating agents and costimulatory molecules include zoledronate, phorbol 12-myristate-13-acetate (TPA), mezerein, staphylococcal enterotoxin A (SEA), streptococcal protein A, or a combination thereof.

In other cases, the activation agent and/or costimulatory agent can be, antibodies or ligands to α TCR, β TCR, γ TCR, δ TCR, CD277, CD28, CD46, CD81, CTLA4, ICOS, PD-1, CD30, NKG2D, NKG2A, HVEM, 4-1 BB (CD137), OX40 (CD134), CD70, CD80, CD86, DAP, CD122, GITR, FcεRIγ, CD1, CD16, CD161, DNAX, accessory molecule-1 (DNAM-1), one or more NCRs (e.g., NKp30, NKp44, NKp46), SLAM, Coxsackie virus and adenovirus receptor or a combination thereof.

Engineered γδ T Cells

Engineered γδ T cells (e.g., δ3 γδ T cells) may be generated with various methods known in the art. An engineered γδ T-cell may be designed to stably express a particular tumor recognition moiety. A polynucleotide encoding an expression cassette that comprises a tumor recognition, or another type of recognition moiety, can be stably introduced into the γδ T-cell by a transposon/transposase system or a viral-based gene transfer system, such as a lentiviral or a retroviral system, or another suitable method, such as transfection, electroporation, transduction, lipofection, calcium phosphate (CaPO$_4$), nanoengineered substances, such as Ormosil, viral delivery methods, including adenoviruses, retroviruses, lentiviruses, adeno-associated viruses, or another suitable method. An antigen specific TCR, either αβ or γδ, can be introduced into the engineered γδ T-cell by stably inserting a polynucleotide comprising a genetic code for the antigen specific TCR into the genome of the γδ T-cell. A polynucleotide encoding a CAR with a tumor recognition moiety may be introduced into the engineered γδ T-cell by stably inserting the polynucleotide into the genome of the γδ T-cell. In some cases, the engineered tumor recognition moiety is an engineered T-cell receptor, and the expression cassette incorporated into the genome of an engineered γδ T-cell comprises a polynucleotide encoding an engineered TCR α (TCR alpha) gene, an engineered TCR β (TCR beta) gene, an TCR δ (TCR delta) gene, or an engineered TCR γ (TCR gamma) gene. In some cases, the expression cassette incorporated into the genome of the engineered γδ T-cell comprises a polynucleotide encoding an antibody fragment or an antigen binding portion thereof. In some cases, the antibody fragment or antigen binding fragment thereof is a polynucleotide encoding a whole antibody, an antibody fragment, a single-chain variable fragment (scFv), a single domain antibody (sdAb), a Fab, F(ab)$_2$, an Fc, the light or heavy chains on an antibody, the variable or the constant region of an antibody, or any combination thereof that binds to a cell surface tumor antigen as part of the Chimeric Antigen Receptor (CAR) construct, or a bi-specific construct, comprising a CAR and a T-cell receptor (TCR), or CARs with antibodies directed to different antigens. In some cases, the polynucleotide is derived from a human or from another species. An antibody fragment or antigen binding fragment polynucleotide that is derived from a non-human species can be modified to increase their similarity to antibody variants produced naturally in humans, and an antibody fragment or antigen binding fragment can be partially or fully humanized. An antibody fragment or antigen binding fragment polynucleotide can also be chimeric, for example a mouse-human antibody chimera. An engineered γδ T-cell that expresses a CAR can also be engineered to express a ligand to the antigen recognized by the tumor recognition moiety.

Various techniques known in the art can be used to introduce a cloned, or synthetically engineered, nucleic acid comprising the genetic code for a tumor recognition moiety into a specific location within the genome of an engineered γδ T-cell. The RNA-guided Cas9 nuclease from the microbial clustered regularly interspaced short palindromic repeats (CRISPR) system, zinc finger nucleases (ZFNs), transcription activator-like effector nucleases (TALENs), and meganuclease technologies, as described, respectively by WO201409370, WO2003087341, WO2014134412, and WO2011090804, each of which is incorporated by reference herein in its entireties, can be used to provide efficient genome engineering in γδ T-cell(s). The technologies described herein can also be used to insert the expression cassette into a genomic location that simultaneously provides a knock-out of one gene and a knock-in of another gene. For example, a polynucleotide comprising an expression cassette of the disclosure can be inserted into a genomic region that encodes for an MHC gene. Such engineering can simultaneously provide the knock-in of one or more genes, e.g. the genes comprised in the expression cassette, and a knock-out of another gene, e.g. an MHC locus.

In one case, a Sleeping Beauty transposon that includes a nucleic acid coding for the tumor recognition moiety is introduced into the cell γδ T-cell that is being engineered. A mutant Sleeping Beauty transposase that provides for enhanced integration as compared to the wild-type Sleeping Beauty, such as the transposase described in U.S. Pat. No. 7,985,739, which is incorporated by reference herein in its entirety, may be used to introduce a polynucleotide in the engineered γδ T-cell.

In some cases, a viral method is used to introduce a polynucleotide comprising a tumor recognition moiety into the genome of an engineered γδ T-cell. A number of viral methods have been used for human gene therapy, such as the methods described in WO 1993020221, which is incorporated herein in its entirety. Non-limiting examples of viral methods that can be used to engineer a γδ T-cell include retroviral, adenoviral, lentiviral, herpes simplex virus, vaccinia virus, pox virus, or adeno-virus associated viral methods.

A polynucleotide containing the genetic code for a tumor recognition moiety may comprise mutations or other transgenes that affect the growth, proliferation, activation status of the engineered γδ T-cell or an antigen specific to tumor cells such as testis-specific cancer antigens. A γδ T-cell of the disclosure may be engineered to express a polynucleotide comprising an activation domain that is linked to the antigen recognition moiety, such as a molecule in TCR-CD3 complex or a co-stimulatory factor. An engineered γδ T-cell can express an intracellular signaling domain that is a T-lymphocyte activation domain. The γδ T-cell may be engineered to express an intracellular activation domain gene or an intracellular signaling domain. The intracellular signaling domain gene, may be, for example CD3ζ, CD28, CD2, ICOS, JAML, CD27, CD30, OX40, NKG2D, CD4, OX40/CD134, 4-1BB/CD137, FcεRIγ, IL-2RB/CD 122, IL-2RG/CD132, DAP molecules, CD70, cytokine receptor, CD40, or any combination thereof. In some cases, the engineered γδ T-cell is also engineered to express a cytokine, an antigen, a cellular receptor, or other immunomodulatory molecule.

The appropriate tumor recognition moiety to be expressed by the engineered γδ T-cell can be selected based on the disease to be treated. For example, in some cases a tumor recognition moiety is a TCR. In some cases, a tumor recognition moiety is a receptor to a ligand that is expressed on a cancer cell. Non-limiting examples of suitable receptors include NKG2D, NKG2A, NKG2C, NKG2F, LLT1, AICL, CD26, NKRP1, CD244 (2B4), DNAM-1, NKp30, NKp44, NKp46, and NKp80. In some cases, a tumor recognition moiety can include a ligand, e.g. IL-13 ligand, or a ligand mimetic to the tumor antigen, such as the IL-13 mimetic to IL13R.

A γδ T-cell may be engineered to express a chimeric tumor recognition moiety comprising a ligand binding domain derived from NKG2D, NKG2A, NKG2C, NKG2F, LLT1, AICL, CD26, NKRP1, CD244 (2B4), DNAM-1, or an anti-tumor antibody such as anti-Her2neu or anti-EGFR and a signaling domain obtained from CD3-ζ, Dap 10, Dap 12, CD28, 41BB, and CD40L. In some examples, the chimeric receptor binds MICA, MICB, Her2neu, EGFR, EGFRvIII, mesothelin, CD38, CD20, CD19, BCMA, PSA, RON, CD30, CD22, CD37, CD38, CD56, CD33, CD138, CD123, CD79b, CD70, CD75, CA6, GD2, alphafetoprotein (AFP), CS1, carcinoembryonic antigen (CEA), CEACAM5, CA-125, MUC-16, 5T4, NaPi2b, ROR1, ROR2, PLIF, Her2/

Neu, EGFRvIII, GPMNB, LIV-1, glycolipidF77,fibroblast activation protein (FAP), PSMA, STEAP-1, STEAP-2, c-Met, CSPG4, CD44v6, PVRL-4, VEGFR2, C4.4a, PSCA, folate binding protein/receptor, SLC44A4, Cripto, CTAG1B, AXL, IL-13Ra2, IL-3R, EPHA3, SLTRK6, gp100, MART1, Tyrosinase, SSX2, SSX4, NYESO-1, epithelial tumor antigen (ETA), MAGEA family genes (such as MAGEA3. MAGEA4), KKLC1, mutated ras (H, N, K), BRaf, p53, Ocatenin, EGFRT790, MHC class I chain-related molecule A (MICA), or MHC class I chain-related molecule B (MICB), or one or more antigens of HPV, CMV, or EBV.

In some cases, the tumor recognition moiety targets an MHC class I molecule (HLA-A, HLA-B, or HLA-C) in complex with a tumor-associated peptide. Methods and compositions for generating and using tumor recognition moieties that target a tumor-associated peptide in complex with a MHC class I molecule include those described in Weidanz et al., Int. Rev. Immunol. 30:328-40, 2011; Scheinberg et al, Oncotarget. 4(5):647-8, 2013; Cheever et al, Clin. Cancer Res. 15(17):5323-37, 2009; Dohan & Reiter Expert Rev Mol Med. 14:e6, 2012; Dao et al., Sci Transl Med. 2013 Mar. 13; 5(176):176ra33; U.S. Pat. No. 9,540, 448; and WO 2017/011804. In some embodiments, the targeted tumor-associated peptide of the peptide MHC complex is a peptide of Wilms' tumor protein 1 (WT1), human telomerase reverse transcriptase (hTERT), survivin, mouse double minute 2 homolog (MDM2), cytochrome P450 (CYP1B), KRAS, or BRAF.

Two or more tumor recognition moieties may be expressed in the γδ T-cell from genetically different, substantially different, or substantially identical, αβ TCR polynucleotides stably expressed from the engineered γδ T-cell or from genetically distinct αβ TCR polynucleotides stably incorporated in the engineered γδ T-cell. In the case of genetically distinct αβ TCR(s), αβ TCR(s) recognizing different antigens associated with the same condition may be utilized. In one preferred embodiment, a γδ T-cell is engineered to express different TCRs, from human or mouse origin, from one or more expression cassettes that recognize the same antigen in the context of different MHC haplotypes. In another preferred embodiment, a γδ T-cell is engineered to express one TCR and two or more antibodies directed to the same or different peptides from a given antigen complexed with different MHC haplotypes. In some cases, expression of a single TCR by an engineered γδ T-cell facilitates proper TCR pairing. An engineered γδ T-cell that expresses different TCRs can provide a universal allogeneic engineered γδ T-cell. In a second preferred embodiment, a γδ T-cell is engineered to express one or more different antibodies directed to peptide-MHC complexes, each directed to the same or different peptide complexed with the same or different MHC haplotypes. In some cases, a tumor recognition moiety can be an antibody that binds to peptide-MHC complexes.

A γδ T-cell can be engineered to express TCRs from one or more expression cassettes that recognize the same antigen in the context of different MHC haplotypes. In some cases, an engineered γδ T-cell is designed to express a single TCR, or a TCR in combination with a CAR to minimize the likelihood of TCR mispairing within the engineered cell. The tumor recognition moieties expressed from two or more expression cassettes preferably have different polynucleotide sequences, and encode tumor recognition moieties that recognize different epitopes of the same target, e.g., in the context of different HLA haplotypes. An engineered γδ T-cell that expresses such different TCRs or CARs can provide a universal allogeneic engineered γδ T-cell.

In some cases, a γδ T-cell is engineered to express one or more tumor recognition moieties. Two or more tumor recognition moieties may be expressed from genetically identical, or substantially identical, antigen-specific chimeric (CAR) polynucleotides engineered in the γδ T-cell. Two or more tumor recognition moieties may be expressed from genetically distinct CAR polynucleotides engineered in the γδ T-cell. The genetically distinct CAR(s) may be designed to recognize different antigens associated with the same condition.

A γδ T-cell may alternatively be bi-specific. A bi-specific engineered γδ T-cell can express two or more tumor recognition moieties. A bi-specific engineered γδ T-cell can express both TCR and CAR tumor recognition moieties. A bi-specific engineered γδ T-cell can be designed to recognize different antigens associated with the same condition. An engineered γδ T-cell can express two or more CAR/TCR(s) bi-specific polynucleotides that recognize an identical or substantially identical antigen. An engineered γδ T-cell can express two or more CAR/TCR(s) bi-specific constructs that recognize distinct antigens. In some cases, a bi-specific construct of the disclosure binds to an activating and an inactivating domain of a target cell, thereby providing increased target specificity. The γδ T-cell may be engineered to express at least 1 tumor recognition moiety, at least 2 tumor recognition moieties, at least 3 tumor recognition moieties, at least 4 tumor recognition moieties, at least 5 tumor recognition moieties, at least 6 tumor recognition moieties, at least 7 tumor recognition moieties, at least 8 tumor recognition moieties, at least 9 tumor recognition moieties, at least 10 tumor recognition moieties, at least 11 tumor recognition moieties, at least 12 tumor recognition moieties, or another suitable number of tumor recognition moieties.

Proper TCR function may be enhanced by two functioning ζ (zeta) proteins comprising ITAM motifs. Proper TCR function may also be enhanced by expression of αβ or γδ activation domains, such as CD3ζ, CD28, CD2, CTLA4, ICOS, JAML, PD-1, CD27, CD30, 41-BB, OX40, NKG2D, HVEM, CD46, CD4, FcεRIγ, IL-2RB/CD122, IL-2RG/CD132, DAP molecules, and CD70. The expressed polynucleotide may include the genetic code for a tumor recognition moiety, a linker moiety, and an activation domain. Translation of the polynucleotide by the engineered γδ T-cell may provide a tumor recognition moiety and an activation domain linked by a protein linker. Often, the linker comprises amino acids that do not obstruct the folding of the tumor recognition moiety and the activation domain. A linker molecule can be at least about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 amino acids in length. In some cases, at least 50%, at least 70% or at least 90% of the amino acids in the linker are serine or glycine.

In some cases, an activation domain can comprise one or more mutations. Suitable mutations may be, for example, mutations that render an activation domain constitutively active. Altering the identity of one or more nucleic acids changes the amino acid sequence of the translated amino acid. A nucleic acid mutation can be made such that the encoded amino acid is modified to a polar, non-polar, basic or acidic amino acid. A nucleic acid mutation can be made such that the tumor recognition moiety is optimized to recognize an epitope from a tumor. The engineered tumor recognition moiety, an engineered activation domain, or another engineered component of a γδ T-cell may include more than 1 amino acid mutation, 2 amino acid mutations, 3 amino acid mutations, 4 amino acid mutations, 5 amino acid mutations, 6 amino acid mutations, 7 amino acid mutations, 8 amino acid mutations, 9 amino acid mutations, 10 amino acid mutations, 11 amino acid mutations, 12 amino acid mutations, 13 amino acid mutations, 14 amino acid mutations, 15 amino acid mutations, 16 amino acid mutations, 17 amino acid mutations, 18 amino acid mutations, 19 amino acid mutations, 20 amino acid mutations, 21 amino acid mutations, 22 amino acid mutations, 23 amino acid mutations, 24 amino acid mutations, 25 amino acid mutations, 26 amino acid mutations, 27 amino acid mutations, 28 amino acid mutations, 29 amino acid mutations, 30 amino acid mutations, 31 amino acid mutations, 32 amino acid mutations, 33 amino acid mutations, 34 amino acid mutations, 35 amino acid mutations, 36 amino acid mutations, 37 amino acid mutations, 38 amino acid mutations, 39 amino acid mutations, 40 amino acid mutations, 41 amino acid mutations, 42 amino acid mutations, 43 amino acid mutations, 44 amino acid mutations, 45 amino acid mutations, 46 amino acid mutations, 47 amino acid mutations, 48 amino acid mutations, 49 amino acid mutations, or 50 amino acid mutations.

In some cases, a γδ T-cell of the disclosure does not express one or more MHC molecules. Deletion of one or more MHC loci in an engineered γδ T-cell can decrease the likelihood that the engineered γδ T-cell will be recognized by the host immune system. The human Major Histocompatibility Complex (MHC) loci, known as the human leukocyte antigen (HLA) system, comprises a large gene family that is expressed in antigen presenting cells, including γδ T-cells. The HLA-A, HLA-B, and HLA-C molecules function to present intracellular peptides as antigens to antigen presenting cells. The HLA-DP, HLA-DM, HLA-DOA, HLA-DOB, HLA-DQ, and HLA-DR molecules function to present extracellular peptides as antigens to antigen presenting cells. Some alleles of the HLA genes have been associated with GVHD, autoimmune disorders, and cancer. An engineered γδ T-cell described herein can be further engineered to lack, or to disrupt gene expression of one or more HLA genes. An engineered γδ T-cell described herein can be further engineered to lack, or to disrupt gene expression of one or more components of the MHC complex, such as complete deletion of one or more of the MHC genes, deletion of specific exons, or deletion of the $\beta_2$ microglobulin (B2m). Genetic excision or genetic disruption of at least one HLA gene can provides a clinically therapeutic γδ T-cell that can be administered to a subject with any HLA haplotype without causing host-versus-graft disease. An engineered γδ T-cell as described herein can be a universal donor for a human subject with any HLA haplotype.

A γδ T-cell can be engineered to lack one or various HLA locus (loci). An engineered γδ T-cell can be engineered to lack an HLA-A allele, an HLA-B allele, an HLA-C allele, an HLA-DR allele, an HLA-DQ allele, or an HLA-DP allele. In some cases, an HLA allele is associated with a human condition, such as an auto-immune condition. For instance, the HLA-B27 allele has been associated with arthritis and uveitis, the HLA-DR2 allele has been associated with systemic lupus erythematosus, and multiple sclerosis, the HLA-DR3 allele has been associated with 21-hydroxylase deficiency, the HLA-DR4 has been associated with rheumatoid arthritis and type 1 diabetes. An engineered γδ T-cell that lacks, for example, the HLA-B27 allele can be administered to a subject afflicted with arthritis without being readily recognized the immune system of the subject. In some cases, deletion of one or more HLA loci provides an engineered γδ T-cell that is a universal donor for any subject with any HLA haplotype.

In some cases, engineering a γδ T-cell requires the deletion of a portion of the γδ T-cell genome. In some cases, the deleted portion of the genome comprises a portion of the MHC locus (loci). In some instances, the engineered γδ T-cell is derived from a wild-type human γδ T-cell, and the MHC locus is an HLA locus. In some cases, the deleted a portion of the genome comprises a portion of a gene corresponding to a protein in the MHC complex. In some cases, the deleted portion of the genome comprises the β2 microglobulin gene. In some instances, the deleted portion of the genome comprises an immune checkpoint gene, such as PD-1, CTLA-4, LAG3, ICOS, BTLA, KIR, TIM3, A2aR, B7-H3, B7-H4, and CECAM-1. In some cases, an engineered γδ T-cell can be designed to express an activation domain that enhances T-cell activation and cytotoxicity. Non-limiting examples of activation domains that can be expressed by an engineered γδ T-cell include: CD2, ICOS, 4-1 BB (CD137), OX40 (CD134), CD27, CD70, CD80, CD86, DAP molecules, CD122, GITR, FcεRIγ.

Any portion of the genome of an engineered γδ T-cell can be deleted to disrupt the expression of an endogenous γδ T-cell gene. Non-limiting examples of genomic regions that can be deleted or disrupted in the genome of an γδ T-cell include a promoter, an activator, an enhancer, an exon, an intron, a non-coding RNA, a micro-RNA, a small-nuclear RNA, variable number tandem repeats (VNTRs), short tandem repeat (STRs), SNP patterns, hypervariable regions, minisatellites, dinucleotide repeats, trinucleotide repeats, tetranucleotide repeats, or simple sequence repeats. In some cases, the deleted a portion of the genome ranges between 1 nucleic acid to about 10 nucleic acids, 1 nucleic acid to about 100 nucleic acids, 1 nucleic acid to about 1,000 nucleic acids, 1 nucleic acid to about 10,000 nucleic acids, 1 nucleic acid to about 100,000 nucleic acids, 1 nucleic acid to about 1,000,000 nucleic acids, or other suitable range.

HLA gene expression in an engineered γδ T-cell can also be disrupted with various techniques known in the art. In some cases, large loci gene editing technologies are used to excise a gene from the engineered γδ T-cell genome, or to disrupt gene expression of at least one HLA locus in the engineered γδ T-cell. Non-limiting examples of gene editing technologies that can be used to edit a desired locus on a genome of an engineered γδ T-cell include Clustered Regularly Interspaced Short Palindromic Repeats (CRISPR)-Cas, zinc finger nucleases (ZFNs), Transcription activator-like effector nucleases (TALENs), and meganuclease technologies, as described, respectively by WO201409370, WO2003087341, WO2014134412, and WO 2011090804, and each of which is incorporated by reference herein in its entireties.

A γδ T-cell may be engineered from an isolated non-engineered γδ T-cell that already expresses a tumor recognition moiety. The engineered γδ T-cell can retain a tumor cell recognition moiety that is endogenously expressed by the isolated wild-type γδ T-cell, e.g., isolated from tumor infiltrating lymphocytes of a tumor sample. In some cases, the engineered γδ T-cell tumor cell recognition moiety replaces the wild-type γδ TCR.

A γδ T-cell can be engineered to express one or more homing molecules, such as a lymphocyte homing molecule. Homing molecules can be, for instance, lymphocyte homing receptors or cell adhesion molecules. A homing molecule can help an engineered γδ T-cell to migrate and infiltrate a solid tumor, including a targeted solid tumor upon administration of the engineered γδ T-cell to the subject. Non-limiting examples of homing receptors include members of the CCR family, e.g: CCR2, CCR4, CCR7, CCR8, CCR9, CCR10, CLA, CD44, CD103, CD62L, E-selectin, P-selectin, L-selectin, integrins, such as VLA-4 and LFA-1. Non-limiting examples of cell adhesion molecules include ICAM, N-CAM, VCAM, PE-CAM, L1-CAM, Nectins (PVRL1, PVRL2, PVRL3), LFA-1, integrin alphaXbeta2, alphavbeta7, macrophage-1 antigen, CLA-4, glycoprotein IIb/IIIa. Additional examples of cell adhesion molecules include calcium dependent molecules, such as T-cadherin, and antibodies to matrix metaloproteinases (MMPs) such as MMP9 or MMP2.

The steps involved in T-cell maturation, activation, proliferation, and function may be regulated through co-stimulatory and inhibitory signals through immune checkpoint proteins. Immune checkpoints are co-stimulatory and inhibitory elements intrinsic to the immune system. Immune checkpoints aid in maintaining self-tolerance and modulating the duration and amplitude of physiological immune responses to prevent injury to tissues when the immune system responds to disease conditions, such as cell transformation or infection. The equilibrium between the co-stimulatory and inhibitory signals used to control the immune response from either γδ and αβ T-cells can be modulated by immune checkpoint proteins. Immune checkpoint proteins, such as PD1 and CTLA4 are present on the surface of T-cells and can be used to turn an immune response "on" or "off." Tumors can dysregulate checkpoint protein function as an immune-resistance mechanism, particularly against T-cells that are specific for tumor antigens. An engineered γδ T-cell of the disclosure can be further engineered to lack one or more immune checkpoint locus (loci), such as PD-1, CTLA-4, LAG3, ICOS, BTLA, KIR, TIM3, A2aR, CEACAM1, B7-H3, and B7-H4. Alternatively, the expression of an endogenous immune check point gene in an engineered γδ T-cell of the disclosure can be disrupted with gene editing technologies.

Immunological checkpoints can be molecules that regulate inhibitory signaling pathways (exemplified by CTLA4, PD1, and LAG3) or molecules that regulate stimulatory signaling pathways (exemplified by ICOS) in an engineered γδ T-cell of the disclosure. Several proteins in the extended immunoglobulin superfamily can be ligands for immunological checkpoints. Non-limiting examples of immune checkpoint ligand proteins include B7-H4, ICOSL, PD-L1, PD-L2, MegaCD40L, MegaOX40L, and CD137L. In some cases, immune checkpoint ligand proteins are antigens expressed by a tumor. In some cases, the immune checkpoint gene is a CTLA-4 gene. In some cases, the immune checkpoint gene is a PD-1 gene.

PD1 is an inhibitory receptor belonging to the CD28/CTLA4 family and is expressed on activated T lymphocytes, B cells, monocytes, DCs, and T-regs. There are two known ligands for PD1, PD-L1 and PD-L2, which are expressed on T cells, APCs, and malignant cells function to suppress self-reactive lymphocytes and to inhibit the effector function of TAA-specific cytotoxic T lymphocytes (CTLs). Accordingly, an engineered γδ T-cell that lacks PD1 can retain its cytotoxic activity regardless of expression of PD-L1 and PD-L2 by tumor cells. In some cases, an engineered γδ T-cell of the disclosure lacks the gene locus for the PD-1 gene. In some cases, expression of the PD-1 gene in an engineered γδ T-cell is disrupted by gene editing technologies.

CTLA4 (cytotoxic T-lymphocyte antigen 4) is also known as CD152 (Cluster of differentiation 152). CTLA4 shares sequence homology and ligands (CD80/B7-1 and CD86/B7-2) with the costimulatory molecule CD28, but differs by delivering inhibitory signals to T-cells expressing CTLA4 as a receptor. CTLA4 has a much higher overall affinity for both ligands and can out-compete CD28 for binding when ligand densities are limiting. CTLA4 is often expressed on the surface of $CD8^+$ effector T-cells, and plays a functional role in the initial activation stages of both naïve and memory T-cells. CTLA4 counteracts the activity of CD28 via increased affinity for CD80 and CD86 during the early stages of T-cell activation. The major functions of CTLA4 include down-modulation of helper T-cells and enhancement of regulatory T-cell immunosuppressive activity. In some instances, an engineered γδ T-cell of the disclosure lacks the CTLA4 gene. In some cases, expression of the CTLA4 gene in an engineered γδ T-cell is disrupted by gene editing technologies.

LAG3 (Lymphocyte-activation gene 3) is expressed on activated antigen-specific cytotoxic T-cells, and can enhance the function of regulatory T-cells and independently inhibit $CD8^+$ effector T-cell activity. LAG3 is a CD-4-like negative regulatory protein with a high affinity binding to MHC Class II proteins, which are upregulated on some epithelial cancers, leading to tolerance of T cell proliferation and homeostasis. Reduction of the LAG-3/Class II interaction using a LAG-3-IG fusion protein may enhance antitumor immune responses. In some cases, an engineered γδ T-cell of the disclosure lacks the gene locus for the LAG3gene. In some instances, expression of the LAG3gene in an engineered γδ T-cell is disrupted by gene editing technologies.

Phenotype of Non-Engineered and Engineered γδ T-cells

An engineered γδ T-cell may home to a specific physical location in a subject's body. Migration and homing of engineered γδ T cells, can be dependent on the combined expression and actions of specific chemokines and/or adhesion molecules. Homing of engineered γδ T cells can be controlled by the interactions between chemokines and their receptors. For example, cytokines including but not limited to CXCR3 (whose ligands are represented by IP-10/CXCL10 and 6Ckine/SLC/CCL21) CCR4+ CXCR5+ (receptor for RANTES, MIP-1α, MIP-1β), CCR6+ and CCR7 may affect homing of engineered γδ T cells. In some cases, an engineered γδ T-cell may home to sites of inflammation and injury, and to diseased cells to perform repair functions. In some cases, an engineered γδ T-cell can home to a cancer. In some cases, an engineered γδ T-cell may home to a thymus, a bone marrow, a skin, a larynx, a trachea, pleurae, a lung, an esophagus, an abdomen, a stomach, a small intestine, a large intestine, a liver, a pancreas, a kidney, a urethra, a bladder, a testis, a prostate, a ductus deferens, am ovary, an uretus, a mamary gland, a parathyroid gland, a spleen or another site in a subject's body. An engineered γδ T-cell can express one or more homing moieties, such as particular TCR allele and/or a lymphocyte homing molecule.

An engineered γδ T-cell may have a particular phenotype and a phenotype can be described in terms of cell-surface marker expression. Various types of γδ T-cells can be engineered as described herein. In preferred embodiments, the engineered γδ T-cell is derived from a human, but the engineered γδ T-cell may also be derived from a different source, such as a mammal or a synthetic cell.

The immunophenotype of the expanded cell populations may be determined using markers including but not limited to CD27, CD45RA, CD45RO, CCR7 and CD62L (Klebanoff et al., Immunol Rev. 211: 214 2006). CD45RA is expressed on naïve T lymphocytes, replaced by CD45RO upon antigen encounter, but re-expressed in late effector cells (Michie et al., Nature 360, 264-265 (1992); CD62L is a cell adhesion molecule that acts as a homing molecule to enter secondary lymphoid tissues and is lost after T-cell activation, when T-cells acquire effector functions (Sallusto et al., Nature. 401:708 (1999). CD27 is costimulation markers that are lost during T-cell differentiations (Appay et al., Nat Med. 8:379 (2002); Klebanoff et al., Immunol Rev. 211: 214 2006).

Antigens

The invention disclosed herein provides an engineered γδ T-cell that expresses an antigen recognition moiety, wherein the antigen recognition moiety recognizes a disease-specific epitope. An antigen may be a molecule that provokes an immune response. This immune response may involve either antibody production, the activation of specific immunologically-competent cells, or both. An antigen may be, for example, a peptide, a protein, a hapten, a lipid, a carbohydrate, bacteria, a pathogen, or a virus. An antigen may be a tumor antigen. A tumor epitope may be presented by the MHC I or MHC II complexes on the surface of tumor cells. An epitope can be the portion of the antigen that is expressed on the cell surface and recognized by the tumor recognition moiety.

Non-limiting examples of antigens recognized by an engineered γδ T-cell include CD19, CD20, CD30, CD22, CD37, CD38, CD56, CD33, CD138, CD123, CD79b, CD70, CD75, CA6, GD2, alphafetoprotein (AFP), carcinoembryonic antigen (CEA), RON, CEACAM5, CA-125, MUC-16, 5T4, NaPi2b, ROR1, ROR2, PLIF, Her2/Neu, EGFRvIII, GPMNB, LIV-1, glycolipidF77,fibroblast activation protein (FAP), PSMA, STEAP-1, STEAP-2, mesothelin, c-Met, CSPG4, PVRL-4, VEGFR2, PSCA, CLEC12a, L1CAM, GPC2, GPC3, folate binding protein/receptor, SLC44A4, Cripto, CTAG1B, AXL, IL-13R, IL-3Ra2, SLTRK6, gp100, MART1, Tyrosinase, SSX2, SSX4, NYESO-1, WT-1, PRAME, epithelial tumor antigen (ETA), MAGEA family genes (such as MAGEA3. MAGEA4), KKLC1, mutated ras, ☐☐af, p53, MHC class I chain-related molecule A (MICA), or MHC class I chain-related molecule B (MICB), or one or more antigens of HPV, CMV, or EBV.

An antigen can be expressed in the intracellular or the extracellular compartment of a cell and an engineered γδ T-cell can recognize an intracellular or an extracellular tumor antigen. In some cases, an αβ TCR in the engineered γδ T-cell recognizes a peptide derived from either an intracellular or an extracellular tumor antigen. For example, an antigen may be a protein intracellularly or extracellularly produced by a cell infected with a virus, such as an HIV, an EBV, a CMV, or an HPV protein. An antigen may also be a protein intracellularly or extracellularly expressed by a cancerous cell.

An antigen recognition moiety may recognize an antigen from a cell in distress, such as a cancerous cell or a cell that has been infected with a virus. For instance, the human MHC class I chain-related genes (MICA and MICB) are located within the HLA class I region of chromosome 6. MICA and MICB proteins are considered to be markers of "stress" in the human epithelia, and act as ligands for cells expressing a common natural killer-cell receptor (NKG2D). As stress markers, MICA and MICB can be highly expressed from cancerous cells. An engineered γδ T-cell can recognize a MICA or a MICB tumor epitope.

A tumor recognition moiety may be engineered to recognize an antigen with certain avidity. For instance, a tumor recognition moiety encoded by a TCR or CAR construct may recognize an antigen with a dissociation constant of at least at least 10 fM, at least 100 fM, at least 1 picomolar (pM), at least 10 pM, at least 20 pM, at least 30 pM, at least 40 pM, at least 50 pM, at least 60 pM, at least 7 pM, at least 80 pM, at least 90 pM, at least 100 pM, at least 200 pM, at least 300 pM, at least 400 pM, at least 500 pM, at least 600 pM, at least 700 pM, at least 800 pM, at least 900 pM, at least 1 nanomolar (nM), at least 2 nM, at least 3 nM, at least 4 nM, at least 5 nM, at least 6 nM, at least 7 nM, at least 8 nM, at least 9 nM, at least 10 nM, at least 20 nM, at least 30 nM, at least 40 nM, at least 50 nm, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, at least 1 µM, at least 2 µM, at least 3 µM, at least 4 µM, at least 5 µM, at least 6 µM, at least 7 µM, at least 8 µM, at least 9 µM, at least 10 µM, at least 20 µM, at least 30 µM, at least 40 µM, at least 50 µM, at least 60 µM, at least 70 µM, at least 80 µM, at least 90 µM, or at least 100 µM.

In some instances, a tumor recognition moiety may be engineered to recognize an antigen with a dissociation constant of at most 10 fM, at most 100 fM, at most 1 picomolar (pM), at most 10 pM, at most 20 pM, at most 30 pM, at most 40 pM, at most 50 pM, at most 60 pM, at most 7 pM, at most 80 pM, at most 90 pM, at most 100 pM, at most 200 pM, at most 300 pM, at most 400 pM, at most 500 pM, at most 600 pM, at most 700 pM, at most 800 pM, at most 900 pM, at most 1 nanomolar (nM), at most 2 nM, at most 3 nM, at most 4 nM, at most 5 nM, at most 6 nM, at most 7 nM, at most 8 nM, at most 9 nM, at most 10 nM, at most 20 nM, at most 30 nM, at most 40 nM, at most 50 nm, at most 60 nM, at most 70 nM, at most 80 nM, at most 90 nM, at most 100 nM, at most 200 nM, at most 300 nM, at most 400 nM, at most 500 nM, at most 600 nM, at most 700 nM, at most 800 nM, at most 900 nM, at most 1 µM, at most 2 µM, at most 3 µM, at most 4 µM, at most 5 µM, at most 6 µM, at most 7 µM, at most 8 µM, at most 9 µM, at most 10 µM, at most 20 µM, at most 30 µM, at most 40 µM, at most 50 µM, at most 60 µM, at most 70 µM, at most 80 µM, at most 90 µM, or at most 100 µM.

Novel Activating Agents

The inventors of the present invention have identified activation agents that bind specific subtypes of γδ TCRs and thereby activate and expand specific populations of γδ T cells. In one aspect, the invention provides novel activating agents which bind the novel activating epitopes identified and described herein in Examples 1 and 2, and FIG. 1. Activation agents include, but are not limited to MAbs δ3-08, δ3-20, δ3-23, δ3-31, δ3-42, δ3-47 and δ3-58. In certain embodiments the activating agent (e.g., antibody) expands and/or activates one or more γδ T-cell populations (e.g., δ3 T cells).

These activation agents further include, but are not limited to activation agents that bind the same epitope or compete with one or more MAbs selected from the group consisting of δ3-08, δ3-20, δ3-23, δ3-31, δ3-42, δ3-47 and δ3-58.

These activation agents further include, but are not limited to activation agents that contain the complementarity determining regions (CDRs) and/or variable regions of a MAb selected from the group consisting of δ3-08, δ3-20, δ3-23, δ3-31, δ3-42, δ3-47 and δ3-58.

The present invention also provides a nucleic acid encoding an activation agent that: (i) contains the complementarity determining regions (CDRs) and/or variable regions of, (ii) binds the same epitope as or competes with; or (iii) is a MAb selected from the group consisting of δ3-08, δ3-20, δ3-23, δ3-31, δ3-42, δ3-47 and δ3-58. In some cases, the nucleic acid is in a host cell (e.g., a heterologous host cell). In some cases, the nucleic acid is operably linked to a heterologous promoter or operably linked to a nucleic acid encoding a heterologous polypeptide. As used herein, the term "heterologous" refers to two components that do not naturally exist together in nature.

The present invention also provides methods of producing one or more of the foregoing activation agents. For example, a host cell containing a nucleic acid encoding an activation agent can be cultured to produce one or more of the foregoing activation agents.

APCs

Also described herein are APCs for expansion of engineered or non-engineered γδ T-cells, such as one or more subpopulations of γδ T-cells. In some embodiments, described herein is an APC that contains a heterologous nucleic acid encoding one or more of the foregoing activation agents. In some embodiments, described herein is an APC that expresses one or more of the foregoing activation agents on a cell surface. In some embodiments, described herein is an APC that expresses one or more Fc receptors on its cell surface, wherein the Fc receptor(s) are in contact with and/or bound to one or more of the foregoing activation agents.

In some cases, the APCs (e.g., APCs having one or more of the foregoing activation agents expressed, on or bound to an Fc receptor expressed on, the cell surface) do not express, or exhibit reduced expression of, HLA class I, HLA class I, invariant chain, and/or HLA-DM. In some cases, the APCs express adhesion molecules such as intercellular adhesion molecule-1, CD11a, CD18, CD54, and/or leukocyte function-associated antigen-3. In some cases, the APCs express an Fc receptor, such as an Fc receptor that is specific for an isotype of an activation agent used in a γδ T-cell expansion method described herein. In some cases, the APCs express one or more Fc receptors selected from the group consisting of CD64, CD32A, CD32B, CD32C, CD16A, CD16B, FcRn, TRIM21, or CD307, or an engineered variant thereof having a higher affinity or altered specificity.

Also described herein cultures comprising one or more of the foregoing APCs. The culture can further contain expanded or unexpanded, engineered or non-engineered, γδ T-cells. The culture can additionally or alternatively contain a selective or non-selective γδ T-cell activation agent including any one of the γδ T-cell activation agents described herein. In some cases, the culture does not contain IL-21. In some cases, the culture does not contain IL-4, IL-2, or IL-15, or a combination thereof. In some cases, the culture does not contain a cytokine that selectively expands a sub-population of γδ T cells.

Epitope Identification

The inventors of the present invention have identified binding regions within the epitope of γδ TCR activating MAbs δ3-08, δ3-20, δ3-23, δ3-31, δ3-42, δ3-47 and δ3-58. Exemplary epitopes include, but are not limited to, the epitopes of γδ TCR activating MAbs δ3-08, δ3-20, δ3-23, δ3-31, δ3-42, δ3-47 and δ3-58. In some embodiments, the epitope is an epitope specifically bound by one or more of γδ TCR activating MAbs δ3-08, δ3-20, δ3-23, δ3-31, 63-42, δ3-47 and δ3-58.

In one aspect, the disclosure provides a method for identifying the epitope of an agent that stimulates the expansion of engineered and non-engineered γδ T-cells at a fast rate of growth. An epitope can include at least 3, 4, 5, 6, 7, 8, 9, 10, 11, 12, 13, 14, 15, 16, 17, 18, 19, or 20 amino acids in a unique spatial conformation. Epitopes can be formed both from contiguous amino acids or noncontiguous amino acids juxtaposed by tertiary folding of a protein. Epitopes formed from contiguous amino acids can be typically retained on exposure to denaturing solvents whereas epitopes formed by tertiary folding can be typically lost on treatment with denaturing solvents.

Epitope mapping can be performed to identify the linear or non-linear, discontinuous amino acid sequence(s), i.e. the epitope, that is (e.g., specifically) recognized by an activating agent of interest, such as the δ3-08, δ3-20, δ3-23, δ3-31, δ3-42, δ3-47 and δ3-58, antibodies. A general approach for epitope mapping can require the expression of the full-length polypeptide sequence that is recognized by an antibody or ligand of interest, as well as various fragments, i.e., truncated forms of the polypeptide sequence, generally in a heterologous expression system. These various recombinant polypeptide sequences or fragments thereof (e.g., fused with an N-terminal protein (e.g., GFP)) can then be used to determine if the antibody or ligand of interest is capable of binding to one or more of the truncated forms of the polypeptide sequence.

In some embodiments, the recombinant polypeptide sequences are chimeras containing joined fragments of two or more homologous parental polypeptides, wherein at least one parental polypeptide binds to the activating agent of interest and at least one parental polypeptide does not bind to the activating agent of interest. For example, segments of a human δ3 chain gene can be joined with segments of a homologous dolphin (or other non-human animal) δ chain gene, and tested for the ability to generate a chimeric TCR in a recombinant expression system. As another segments of a human δ3 chain gene can be joined with segments of a different δ chain subtype. Chimeric TCR genes that form a TCR, as e.g., indicated by detection with a pan-γδ-TCR antibody on a cell surface, can then be tested for binding to the activation agent of interest.

Through the use of reiterative truncation and the generation of recombinant polypeptide sequences with overlapping amino acid regions, it is possible to identify the region of the polypeptide sequence that is recognized by the antibody of interest (see, e.g., Epitope Mapping Protocols in Methods in Molecular Biology, Vol. 66, Glenn E. Morris, Ed (1996)). The methods rely on the ability of an agent such as an antibody of interest to bind to sequences that have been recreated from epitope libraries, such as epitope libraries derived from, synthetic peptide arrays on membrane supports, combinatorial phage display peptide libraries. The epitope libraries then provide a range of possibilities that are screened against an antibody. Additionally, site specific mutagenesis, or random Ala scan, targeting one or more residues of an epitope can be pursued to confirm the identity of an epitope.

A library of epitopes can be created by synthetically designing various possible recombinations of a γδ T-cell receptor (γδ TCR) as cDNA constructs and expressing them in a suitable system. For instance, a plurality of Vδ3 gene segments differing in their Jδ region can be synthetically designed, including Jδ1, Jδ2 and Jδ3 gene segments. Such, Vδ3J segments can, e.g., be ordered as synthetic genes and cloned into suitable vectors. A plurality of synthetically cloned δ3 TCR chains, such as Vδ3J1, Vδ3J2, Vδ3J3, or Vδ3J4 chains can be co-transfected into a host system with synthetically cloned γ TCR chains such as Vγ2, Vγ3, Vγ4, Vγ5,Vγ8, Vγ9 and Vγ10 synthetically designed gene segments. In other cases, δ TCR chains, can be amplified out of Total RNA extracted from human PBMCs or γδ T-cells isolated from human normal and malignant tissue.

The host system can be any suitable expression system such as 293 cells, insect cells, or a suitable in-vitro translation system. The plurality of various possible combinations of synthetically designed γδ T-cell segments transfected into a host system can provide, for instance, more than 25, 30, 35, 40, 45, 50, 55, 60, 65, 70, 75, 80, 85, or 90 possible pairing combinations of γδ TCRs. The binding of an agent to one of the epitopes in the previously described library can be detected by contacting a labeled antibody, such as δ3-08, δ3-20, δ3-23, δ3-31, δ3-42, δ3-47 and δ3-58, with an epitope of the library and detecting a signal from the label. Alternatively, the binding of the agent can be detected using a labeled secondary antibody such a an anti-mouse antibody.

For epitope mapping, computational algorithms have also been developed which have been shown to map conformational discontinuous epitopes. Conformational epitopes can be identified by determining spatial conformation of amino acids with methods that include, e.g., x-ray crystallography and 2-dimensional nuclear magnetic resonance. Some epitope mapping methods, such as, x-ray analyses of crystals of antigen:antibody complexes can provide atomic resolution of the epitope. In other cases, computational combinatorial methods for epitope mapping can be employed to model a potential epitope based on the sequence of the antibody, such as δ3-08, δ3-20, δ3-23, δ3-31, δ3-42, δ3-47 or δ3-58 antibody. In such cases, the antigen binding portion of the antibody is sequenced, and computation models are used to reconstruct and predict a potential binding site of the antibody.

In some cases the disclosure provides a method of determining an epitope of a γδ T-cell receptor, comprising: (a) preparing a library of epitopes from the γδ T-cell receptor; (b) contacting the library of epitopes with an antibody; and (b) identifying the amino acid sequence of at least one epitope in the library of epitopes that is bound by the antibody. In some cases, the antibody is selected from the group consisting of, δ3-08, δ3-20, δ3-23, δ3-31, δ3-42, δ3-47 and δ3-58, antibodies. In one instance, the antibody is attached to a solid support. The library of epitopes can comprise sequences that correspond to continuous and discontinuous epitopes of a T-cell receptor, such as a γ TCR or a δ TCR. In some cases, the library of epitopes comprises fragments from a γδ T-cell receptor ranging from about 10 amino acids to about 30 amino acids in length, from about 10 amino acids to about 20 amino acids in length, or from about 5 amino acids to about 12 amino acids in length. In some cases, the antibody is labeled and the label is a radioactive molecule, a luminescent molecule, a fluorescent molecule, an enzyme, or biotin.

δ3 Epitope Bins

In some embodiments, the activating agent of interest competes with the binding to γ2 δ3TCR of one or more Bin 1A antibodies δ3-23, δ3-42, and/or δ3-58. In some embodiments, the activating agent of interest competes with the binding to γ2 δ3TCR of Bin 1B antibody δ3-08. In some embodiments, the activating agent of interest competes with the binding to γ2 δ3TCR of one or more Bin 1 (Bin1A and Bin1B) antibodies δ3-23, δ3-42, δ3-58, and/or δ3-08. In some embodiments, the activating agent of interest competes with the binding to γ2 δ3TCR of Bin 2 antibody δ3-31.

Generally, the δ3-specific antibodies described herein recognize a conformational epitope in the context of a γδ-TCR. In some cases, the δ3-specific antibodies described herein are specific for one or more pairs of γδ3-TCRs respectively. For example, in some cases, the δ3-specific antibodies described herein are specific for a γ2 δ3-TCR.

Methods of Treatment

Pharmaceutical compositions containing a non-engineered, enriched γδ T-cell population, an engineered, enriched γδ T-cell population, and/or admixtures thereof, as described herein may be administered for prophylactic and/or therapeutic treatments. In therapeutic applications, the compositions can be administered to a subject already suffering from a disease or condition in an amount sufficient to cure or at least partially arrest the symptoms of the disease or condition. A non-engineered, enriched γδ T-cell population, an engineered, enriched γδ T-cell population, and/or admixtures thereof, can also be administered to lessen a likelihood of developing, contracting, or worsening a condition. Effective amounts of a population of a non-engineered, enriched γδ T-cell population, an engineered, enriched γδ T-cell population, and/or admixtures thereof, for therapeutic use can vary based on the severity and course of the disease or condition, previous therapy, the subject's health status, weight, and/or response to the drugs, and/or the judgment of the treating physician.

A non-engineered, enriched γδ T-cell population, an engineered, enriched γδ T-cell population, and/or admixtures thereof, of the disclosure can be used to treat a subject in need of treatment for a condition. Examples of conditions include cancer, infectious disease, autoimmune disorder and sepsis. Subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, or infants.

A method of treating a condition (e.g., ailment) in a subject with an enriched γδ T-cell population of the instant invention may comprise administering to the subject a therapeutically-effective amount of a non-engineered, enriched γδ T-cell population, an engineered, enriched γδ T-cell population, and/or admixtures thereof. An enriched γδ T-cell population, and/or admixtures thereof, of the disclosure may be administered at various regimens (e.g., timing, concentration, dosage, spacing between treatment, and/or formulation). A subject can also be preconditioned with, for example, chemotherapy, radiation, or a combination of both, prior to receiving a an enriched γδ T-cell population and/or admixtures thereof, of the disclosure. As part of a treatment, a non-engineered, enriched γδ T-cell population, an engineered, enriched γδ T-cell population, and/or admixtures thereof, may be administered to a subject at a first regimen and the subject may be monitored to determine whether the treatment at the first regimen meets a given level of therapeutic efficacy. In some cases, the engineered γδ T-cell or another engineered γδ T-cell may be administered to the subject at a second regimen. FIG. 2 schematically illustrates a method for treating a subject. In a first operation 201, at least one engineered γδ T-cell is administered to a subject that has or is suspected of having a given condition (e.g., cancer). The engineered γδ T-cell may be administered at a first regimen. In a second operation 202, the subject may be monitored, for example by a healthcare provider (e.g., treating physician or nurse). In some examples, the subject is monitored to determine or gauge an efficacy of the engineered γδ T-cell in treating the condition of the subject. In some situations, the subject may also be monitored to determine the in vivo expansion of a γδ T-cell population in the subject. Next, in a third operation 203, at least one other engineered γδ T-cell is administered to the subject at a second regimen. The second regimen may be the same as the first regimen or different than the first regimen. In some situations, the third operation 203 is not performed, for example, if the administration of the engineered γδ T-cell in the first operation 201 is found to be effective (e.g., a single round of administration may be sufficient to treat the condition). Due to their allogeneic and universal donor characteristics, a population of engineered γδ T-cells may be administrated to various subjects, with different MHC haplotypes. An engineered γδ T-cell may be frozen or cryopreserved prior to being administered to a subject.

Figure 3:
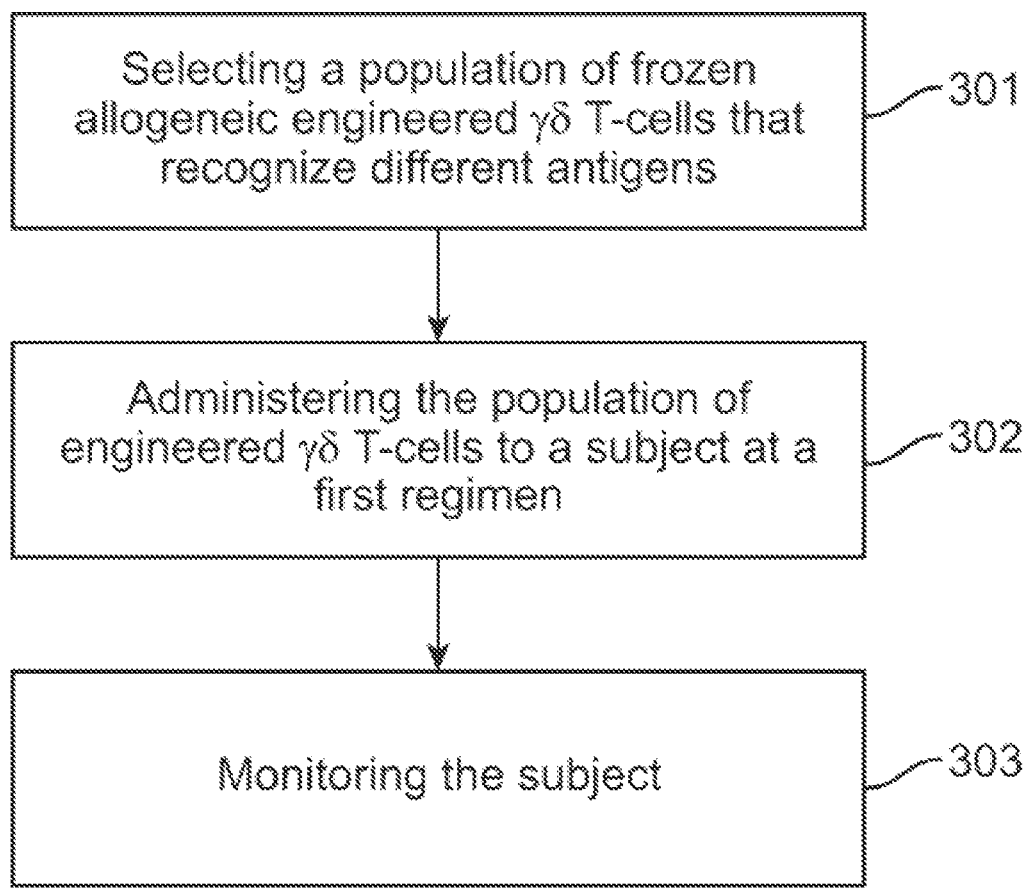
FIG. 3 schematically illustrates a method for administering a population of engineered γδ T cells to a subject.

A enriched population of γδ T-cells (i.e., engineered or non-engineered) and/or admixtures thereof, may also be frozen or cryopreserved prior to being administered to a subject. In certain embodiments, a population of engineered, enriched γδ T-cells can comprise two or more cells that express identical, different, or a combination of identical and different tumor recognition moieties. For instance, a population of engineered, enriched γδ T-cells can comprises several distinct engineered γδ T-cells that are designed to recognize different antigens, or different epitopes of the same antigen. For example, human cells afflicted with melanoma can express the NY-ESO-1 oncogene. Infected cells within the human can process the NY-ESO-1 oncoprotein into smaller fragments and present various portions of the NY-ESO-1 protein for antigen recognition. A population of engineered, enriched γδ T-cells can comprise various engineered γδ T-cells that express different tumor recognition moieties designed to recognize different portions of the NY-ESO-1 protein. FIG. 3 schematically illustrates a method for treating a subject with a population of engineered γδ T-cells that recognizes different epitopes of the melanoma antigen NY-ESO-1. In a first operation 301, a population of engineered γδ T-cells that recognize different epitopes of the same antigen is selected. For example, the population of engineered γδ T-cells may comprise two or more cells that expressing different tumor recognition moieties that recognize different portions of the NY-ESO-1protein. In a second operation 302, The population of engineered γδ T-cells may be administered at a first regimen. In a second operation 303, the subject may be monitored, for example by a healthcare provider (e.g., treating physician or nurse).

An enriched γδ T-cell population, i.e., non-engineered or engineered, and/or admixtures thereof, of the disclosure may be used to treat various conditions. In some cases, a non-engineered, enriched γδ T-cell population, an engineered, enriched γδ T-cell population, and/or admixtures thereof, of the disclosure may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some cases, a non-engineered, enriched γδ T-cell population, an engineered, enriched γδ T-cell population, and/or admixtures thereof, of the disclosure may be used to treat an infectious disease. An infectious disease may be caused, for example, by a pathogenic bacterium or by a virus. Various pathogenic proteins, nucleic acids, lipids, or fragments thereof can be expressed by a diseased cell. An antigen presenting cell can internalize such pathogenic molecules, for instance with phagocytosis or by receptor-mediated endocytosis, and display a fragment of the antigen bound to an appropriate MHC molecule. For instance, various 9 mer fragments of a pathogenic protein may be displayed by an APC. Engineered, enriched γδ T-cell populations of the disclosure may be designed to recognize various antigens and antigen fragments of a pathogenic bacterium or a virus. Non-limiting examples of pathogenic bacteria can be found in the: a) *Bordetella* genus, such as *Bordetella pertussis* species; b) *Borrelia* genus, such *Borrelia burgdorferi* species; c) *Brucelia* genus, such as *Brucella abortus, Brucella canis, Brucela meliterisis*, and/or *Brucella suis* species; d) *Campylobacter* genus, such as *Campylobacter jejuni* species; e) *Chlamydia* and *Chlamydophila* genuses, such as *Chlamydia* pneumonia, *Chlamydia trachomatis*, and/or *Chlamydophila psittaci* species; f) *Clostridium* genus, such as *Clostridium botulinum, Clostridium difficile, Clostridium perfringens, Clostridium tetani* species; g) *Corynebacterium* genus, such as *Corynebacterium diphtheria* species; h) *Enterococcus* genus, such as *Enterococcus faecalis*, and/or *Enterococcus faecium* species; i) *Escherichia* genus, such as *Escherichia coli* species; j) *Francisella* genus, such as *Francisella tularensis* species; k) *Haemophilus* genus, such as *Haemophilus* influenza species; l) *Helicobacter* genus, such as *Helicobacter pylori* species; m) *Legionella* genus, such as *Legionella pneumo-* phila species; n) *Leptospira* genus, such as *Leptospira interrogans* species; o) *Listeria* genus, such as *Listeria monocytogenes* species; p) *Mycobacterium* genus, such as *Mycobacterium leprae, Mycobacterium tuberculosis,* and/or *mycobacterium ulcerans* species; q) *Mycoplasma* genus, such as *Mycoplasma* pneumonia species; r) *Neisseria* genus, such as *Neisseria gonorrhoeae* and/or *Neisseria meningitidia* species; s) *Pseudomonas* genus, such as *Pseudomonas aeruginosa* species; t) *Rickettsia* genus, such as *Rickettsia rickettsii* species; u) *Salmonella* genus, such as *Salmonella typhi* and/or *Salmonella typhimurium* species; v) *Shigella* genus, such as *Shigella sonnei* species; w) *Staphylococcus* genus, such as *Staphylococcus aureus, Staphylococcus epidermidis,* and/or *Staphylococcus saprophyticus* species; x) *Streptpcoccus* genus, such as *Streptococcus agalactiae, Streptococcus pneumonia,* and/or *Streptococcus pyogenes* species; y) *Treponema* genus, such as *Treponema pallidum* species; z) *Vibrio* genus, such as *Vibrio cholera*; and/or aa) *Yersinia* genus, such as *Yersinia pestis* species.

In some cases, a non-engineered, enriched γδ T-cell population, an engineered, enriched γδ T-cell population, and/or admixtures thereof, of the disclosure may be used to treat an infectious disease, an infectious disease may be caused a virus. Non-limiting examples of viruses can be found in the following families of viruses and are illustrated with exemplary species: a) Adenoviridae family, such as Adenovirus species; b) Herpesviridae family, such as Herpes simplex type 1, Herpes simplex type 2, Varicella-zoster virus, Epstein-barr virus, Human cytomegalovirus, Human herpesvirus type 8 species; c) Papillomaviridae family, such as Human papillomavirus species; d) Polyomaviridae family, such as BK virus, JC virus species; e) Poxviridae family, such as Smallpox species; f) Hepadnaviridae family, such as Hepatitis B virus species; g) Parvoviridae family, such as Human bocavirus, Parvovirus B19 species; h) Astroviridae family, such as Human astrovirus species; i) Caliciviridae family, such as Norwalk virus species; j) Flaviviridae family, such as Hepatitis C virus (HCV), yellow fever virus, dengue virus, West Nile virus species; k) Togaviridae family, such as Rubella virus species; l) Hepeviridae family, such as Hepatitis E virus species; m) Retroviridae family, such as Human immunodeficiency virus (HIV) species; n) Orthomyxoviridaw family, such as Influenza virus species; o) Arenaviridae family, such as Guanarito virus, Junin virus, Lassa virus, Machupo virus, and/or Sabia virus species; p) Bunyaviridae family, such as Crimean-Congo hemorrhagic fever virus species; q) Filoviridae family, such as Ebola virus and/or Marburg virus species; Paramyxoviridae family, such as Measles virus, Mumps virus, Parainfluenza virus, Respiratory syncytial virus, Human metapneumovirus, Hendra virus and/or Nipah virus species; r) Rhabdoviridae genus, such as Rabies virus species; s) Reoviridae family, such as Rotavirus, Orbivirus, Coltivirus and/or Banna virus species. In some examples, a virus is unassigned to a viral family, such as Hepatitis D.

In some cases, a non-engineered, enriched γδ T-cell population, an engineered, enriched γδ T-cell population, and/or admixtures thereof, of the disclosure may be used to treat an immune disease, such as an autoimmune disease. Inflammatory diseases, including autoimmune diseases are also a class of diseases associated with B-cell disorders. Examples of immune diseases or conditions, including autoimmune conditions, include: rheumatoid arthritis, rheumatic fever, multiple sclerosis, experimental autoimmune encephalomyelitis, psoriasis, uveitis, diabetes mellitus, systemic lupus erythematosus (SLE), lupus nephritis, eczema, scleroderma, polymyositis/scleroderma, polymyositis/dermatomyositis, uncerative protitis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, HIV, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis, acute idiopathic thrombocytopenic purpura, chronic idiopathic thrombocytopenia purpura, dermatomyositis, Sydenham'a chorea, myasthenia gravis, polyglandular syndromes, bullous pemphigoid, Henoch-Schonlein purpura, poststreptococcalnephritis, erythema nodosum, erythema multiforme, gA nephropathy, Takayasu's arteritis, Addison's disease, sarcoidosis, ulcerative colitis, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, chronic active hepatitis, polychondritis, pamphigus vulgaris, Wegener's granulomatosis, membranous nephropathy, amyotrophic lateral sclerosis, tabes dorsalis, giant cell arteritis/polymyalgia, peraiciousanemia, rapidly progressive glomerulonephritis, psoriasis, fibrosing alveolitis, and cancer.

Treatment with a γδ T-cell population, and/or admixtures thereof, of the disclosure may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can comprise administering to a subject a pharmaceutical composition comprising a non-engineered, enriched γδ T-cell population, an engineered, enriched γδ T-cell population, and/or admixture thereof, of the disclosure.

In some cases, administration of a non-engineered, enriched γδ T-cell population, an engineered, enriched γδ T-cell population, and/or admixture thereof, of the disclosure to a subject modulates the activity of endogenous lymphocytes in a subject's body. In some cases, administration of the non-engineered, enriched γδ T-cell population, an engineered, enriched γδ T-cell population, and/or admixtures thereof, to a subject provides an antigen to an endogenous T-cell and may boost an immune response. In some cases, the memory T-cell is a $CD4^+$ T-cell. In some cases, the memory T-cell is a $CD8^+$ T-cell. In some cases, administration of the non-engineered, enriched γδ T-cell population, an engineered, enriched γδ T-cell population, and/or admixtures thereof, to a subject activates the cytotoxicity of another immune cell. In some cases, the other immune cell is a $CD8^+$ T-cell. In some cases, the other immune cell is a Natural Killer T-cell. In some cases, administration of the non-engineered, enriched γδ T-cell population, an engineered, enriched γδ T-cell population, and/or admixtures thereof, to a subject suppress a regulatory T-cell. In some cases, the regulatory T-cell is a Fox3+ Treg cell. In some cases, the regulatory T-cell is a Fox3− Treg cell. Non-limiting examples of cells whose activity can be modulated by a non-engineered, enriched γδ T-cell population, an engineered, enriched γδ T-cell population, and/or admixtures thereof, of the disclosure include: hematopioietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells.

During most bone marrow transplants, a combination of cyclophosphamide with total body irradiation is conventionally employed to prevent rejection of the hematopietic stem cells (HSC) in the transplant by the subject's immune system. In some cases, incubation of donor bone marrow with interleukin-2 (IL-2) ex vivo is performed to enhance the generation of killer lymphocytes in the donor marrow. Interleukin-2 (IL-2) is a cytokine that is necessary for the growth, proliferation, and differentiation of wild-type lymphocytes. Current studies of the adoptive transfer of γδ T-cells into humans may require the co-administration of γδ T-cells and interleukin-2. However, both low- and high-dosages of IL-2 can have highly toxic side effects. IL-2 toxicity can manifest in multiple organs/systems, most significantly the heart, lungs, kidneys, and central nervous system. In some cases, the disclosure provides a method for administrating a non-engineered, enriched γδ T-cell population, an engineered, enriched γδ T-cell population, and/or admixtures thereof, to a subject without the co-administration of a cytokine, such as IL-2, IL-15, IL-12, or IL-21. In some cases, a non-engineered, enriched γδ T-cell population, an engineered, enriched γδ T-cell population, and/or admixtures thereof, can be administered to a subject without co-administration with IL-2. In some cases, a non-engineered, enriched γδ T-cell population, an engineered, enriched γδ T-cell population, and/or admixtures thereof, is administered to a subject during a procedure, such as a bone marrow transplant without the co-administration of IL-2.

Methods of Administration

One or multiple non-engineered, enriched γδ T-cell population, engineered, enriched γδ T-cell population, and/or admixtures thereof, of the invention can be administered to a subject in any order or simultaneously. If simultaneously, the multiple non-engineered, enriched γδ T-cell population, engineered, enriched γδ T-cell population, and/or admixtures thereof, of the invention can be provided in a single, unified form, such as an intravenous injection, or in multiple forms, for example, as multiple intravenous infusions, s.c, injections or pills. The non-engineered, enriched γδ T-cell population, engineered, enriched γδ T-cell population, and/or admixtures thereof, of the invention can be packed together or separately, in a single package or in a plurality of packages. One or all of the non-engineered, enriched γδ T-cell population, engineered, enriched γδ T-cell population, and/or admixtures thereof, of the invention can be given in multiple doses. If not simultaneous, the timing between the multiple doses may vary to as much as about a week, a month, two months, three months, four months, five months, six months, or about a year. In some cases, a non-engineered, enriched γδ T-cell population, an engineered, enriched γδ T-cell population, and/or admixtures thereof, of the invention can expand within a subject's body, in vivo, after administration to a subject. Non-engineered, enriched γδ T-cell population, engineered, enriched γδ T-cell population, and/or admixtures thereof, can be frozen to provide cells for multiple treatments with the same cell preparation. Non-engineered, enriched γδ T-cell population, engineered, enriched γδ T-cell population, and/or admixtures thereof, of the disclosure, and pharmaceutical compositions comprising the same, can be packaged as a kit. A kit may include instructions (e.g., written instructions) on the use of the non-engineered, enriched γδ T-cell population, the engineered, enriched γδ T-cell population, and/or admixtures thereof, and compositions comprising the same.

In some cases, a method of treating a cancer comprises administering to a subject a therapeutically-effective amount of a non-engineered, enriched γδ T-cell population, an engineered, enriched γδ T-cell population, and/or admixtures thereof, wherein the administration treats the cancer. In some embodiments the therapeutically-effective amount of the non-engineered, enriched γδ T-cell population, the engineered, enriched γδ T-cell population, and/or admixtures thereof, is administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In some embodiments the therapeutically-effective amount of the non-engineered, enriched γδ T-cell population, the engineered, enriched γδ T-cell population, and/or admixtures thereof, is administered for at least one week. In some embodiments the therapeutically-effective amount of the non-engineered, enriched γδ T-cell population, the engineered, enriched γδ T-cell population, and/or admixtures thereof, is administered for at least two weeks.

A non-engineered, enriched γδ T-cell population, an engineered, enriched γδ T-cell population, and/or admixtures thereof, described herein can be administered before, during, or after the occurrence of a disease or condition, and the timing of administering a pharmaceutical composition containing a non-engineered, enriched γδ T-cell population, an engineered, enriched γδ T-cell population, and/or admixtures thereof, can vary. For example, the non-engineered, enriched γδ T-cell population, the engineered, enriched γδ T-cell population, and/or admixtures thereof, can be used as a prophylactic and can be administered continuously to subjects with a propensity to conditions or diseases in order to lessen a likelihood of the occurrence of the disease or condition. The non-engineered, enriched γδ T-cell population, the engineered, enriched γδ T-cell population, and/or admixtures thereof, can be administered to a subject during or as soon as possible after the onset of the symptoms. The administration of the non-engineered, enriched γδ T-cell population, the engineered, enriched γδ T-cell population, and/or admixtures thereof, can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In some examples, the administration of a non-engineered, enriched γδ T-cell population, an engineered, enriched γδ T-cell population, and/or admixtures thereof, of the disclosure is an intravenous administration. One or multiple dosages of a non-engineered, enriched γδ T-cell population, an engineered, enriched γδ T-cell population, and/or admixtures thereof, can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of a non-engineered, enriched γδ T-cell population, an engineered, enriched γδ T-cell population, and/or admixtures thereof, can be administered years after onset of the cancer and before or after other treatments. In some examples, a non-engineered, enriched γδ T-cell population, an engineered, enriched γδ T-cell population, and/or admixtures thereof, can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject.

Dosages

A non-engineered, enriched γδ T-cell population, an engineered, enriched γδ T-cell population, and/or admixtures thereof, as disclosed herein may be formulated in unit dosage forms suitable for single administration of precise dosages. In some cases, the unit dosage forms comprise additional lymphocytes. In unit dosage form, the formulation is divided into unit doses containing appropriate quantities of one or more compounds. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Multiple-dose reclosable containers can be used, for example, in combination with a preservative or without a preservative. In some examples, the pharmaceutical composition does not comprise a preservative. Formulations for parenteral injection can be presented in unit dosage form, for example, in ampoules, or in multi-dose containers with a preservative.

A non-engineered, enriched γδ T-cell population, an engineered, enriched γδ T-cell population, and/or admixtures thereof, as described herein may be present in a composition in an amount of at least 5 cells, at least 10 cells, at least 20 cells, at least 30 cells, at least 40 cells, at least 50 cells, at least 60 cells, at least 70 cells, at least 80 cells, at least 90 cells, at least 100 cells, at least 200 cells, at least 300 cells, at least 400 cells, at least 500 cells, at least 600 cells, at least 700 cells, at least 800 cells, at least 900 cells, at least $1\times10^3$ cells, at least $2\times10^3$ cells, at least $3\times10^3$ cells, at least $4\times10^3$ cells, at least $5\times10^3$ cells, at least $6\times10^3$ cells, at least $7\times10^3$ cells, at least $8\times10^3$ cells, at least $9\times10^3$ cells, at least $1\times10^4$ cells, at least $2\times10^4$ cells, at least $3\times10^4$ cells, at least $4\times10^4$ cells, at least $5\times10^4$ cells, at least $6\times10^4$ cells, at least $7\times10^4$ cells, at least $8\times10^4$ cells, at least $9\times10^4$ cells, at least $1\times10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, at least $1\times10^7$ cells, at least $2\times10^7$ cells, at least $3\times10^7$ cells, at least $4\times10^7$ cells, at least $5\times10^7$ cells, at least $6\times10^7$ cells, at least $7\times10^7$ cells, at least $8\times10^7$ cells, at least $9\times10^7$ cells, at least $1\times10^8$ cells, at least $2\times10^8$ cells, at least $3\times10^8$ cells, at least $4\times10^8$ cells, at least $5\times10^8$ cells, at least $6\times10^8$ cells, at least $7\times10^8$ cells, at least $8\times10^8$ cells, at least $9\times10^8$ cells, at least $1\times10^9$ cells, or more.

The therapeutically effective dose of a non-engineered, enriched γδ T-cell population, an engineered, enriched γδ T-cell population, and/or admixtures thereof, of the invention can be from about 1 cell to about 10 cells, from about 1 cell to about 100 cells, from about 1 cell to about 10 cells, from about 1 cell to about 20 cells, from about 1 cell to about 30 cells, from about 1 cell to about 40 cells, from about 1 cell to about 50 cells, from about 1 cell to about 60 cells, from about 1 cell about 70 cells, from about 1 cell to about 80 cells, from about 1 cell to about 90 cells, from about 1 cell to about 100 cells, from about 1 cell to about $1\times10^3$ cells, from about 1 cell to about $2\times10^3$ cells, from about 1 cell to about $3\times10^3$ cells, from about 1 cell to about $4\times10^3$ cells, from about 1 cell to about $5\times10^3$ cells, from about 1 cell to about $6\times10^3$ cells, from about 1 cell to about $7\times10^3$ cells, from about 1 cell to about $8\times10^3$ cells, from about 1 cell to about $9\times10^3$ cells, from about 1 cell to about $1\times10^4$ cells, from about 1 cell to about $2\times10^4$ cells, from about 1 cell to about $3\times10^4$ cells, from about 1 cell to about $4\times10^4$ cells, from about 1 cell to about $5\times10^4$ cells, from about 1 cell to about $6\times10^4$ cells, from about 1 cell to about $7\times10^4$ cells, from about 1 cell to about $8\times10^4$ cells, from about 1 cell to about $9\times10^4$ cells, from about 1 cell to about $1\times10^5$ cells, from about 1 cell to about $2\times10^5$ cells, from about 1 cell to about $3\times10^5$ cells, from about 1 cell to about $4\times10^5$ cells, from about 1 cell to about $5\times10^5$ cells, from about 1 cell to about $6\times10^5$ cells, from about 1 cell to about $7\times10^5$ cells, from about 1 cell to about $8\times10^5$ cells, from about 1 cell to about $9\times10^5$ cells, from about 1 cell to about $1\times10^6$ cells, from about 1 cell to about $2\times10^6$ cells, from about 1 cell to about $3\times10^6$ cells, from about 1 cell to about $4\times10^6$ cells, from about 1 cell to about $5\times10^6$ cells, from about 1 cell to about $6\times10^6$ cells, from about 1 cell to about $7\times10^6$ cells, from about 1 cell to about $8\times10^6$ cells, from about 1 cell to about $9\times10^6$ cells, from about 1 cell to about $1\times10^7$ cells, from about 1 cell to about $2\times10^7$ cells, from about 1 cell to about $3\times10^7$ cells, from about 1 cell to about $4\times10^7$ cells, from about 1 cell to about $5\times10^7$ cells, from about 1 cell to about $6\times10^7$ cells, from about 1 cell to about $7\times10^7$ cells, from about 1 cell to about $8\times10^7$ cells, from about 1 cell to about $9\times10^7$ cells, from about 1 cell to about $1\times10^8$ cells, from about 1 cell to about $2\times10^8$ cells, from about 1 cell to about $3\times10^8$ cells, from about 1 cell to about $4\times10^8$ cells, from about 1 cell to about $5\times10^8$ cells, from about 1 cell to about $6\times10^8$ cells, from about 1 cell to about $7\times10^8$ cells, from about 1 cell to about $8\times10^8$ cells, from about 1 cell to about $9\times10^8$ cells, or from about 1 cell to about $1\times10^9$ cells.

In some cases, the therapeutically effective dose of a non-engineered, enriched γδ T-cell population, an engineered, enriched γδ T-cell population, and/or admixtures thereof, of the invention can be from about $1\times10^3$ cells to about $2\times10^3$ cells, from about $1\times10^3$ cells to about $3\times10^3$ cells, from about $1\times10^3$ cells to about $4\times10^3$ cells, from about $1\times10^3$ cells to about $5\times10^3$ cells, from about $1\times10^3$ cells to about $6\times10^3$ cells, from about $1\times10^3$ cells to about $7\times10^3$ cells, from about $1\times10^3$ cells to about $8\times10^3$ cells, from about $1\times10^3$ cells to about $9\times10^3$ cells, from about $1\times10^3$ cells to about $1\times10^4$ cells, from about $1\times10^3$ cells to about $2\times10^4$ cells, from about $1\times10^3$ cells to about $3\times10^4$ cells, from about $1\times10^3$ cells to about $4\times10^4$ cells, from about $1\times10^3$ cells to about $5\times10^4$ cells, from about $1\times10^3$ cells to about $6\times10^4$ cells, from about $1\times10^3$ cells to about $7\times10^4$ cells, from about $1\times10^3$ cells to about $8\times10^4$ cells, from about $1\times10^3$ cells to about $9\times10^4$ cells, from about $1\times10^3$ cells to about $1\times10^5$ cells, from about $1\times10^3$ cells to about $2\times10^5$ cells, from about $1\times10^3$ cells to about $3\times10^5$ cells, from about $1\times10^3$ cells to about $4\times10^5$ cells, from about 1×10³ cells to about 5×10⁵ cells, from about 1×10³ cells to about 6×10⁵ cells, from about 1×10³ cells to about 7×10⁵ cells, from about 1×10³ cells to about 8×10⁵ cells, from about 1×10³ cells to about 9×10⁵ cells, from about 1×10³ cells to about 1×10⁶ cells, from about 1×10³ cells to about 2×10⁶ cells, from about 1×10³ cells to about 3×10⁶ cells, from about 1×10³ cells to about 4×10⁶ cells, from about 1×10³ cells to about 5×10⁶ cells, from about 1×10³ cells to about 6×10⁶ cells, from about 1×10³ cells to about 7×10⁶ cells, from about 1×10³ cells to about 8×10⁶ cells, from about 1×10³ cells to about 9×10⁶ cells, from about 1×10³ cells to about 1×10⁷ cells, from about 1×10³ cells to about 2×10⁷ cells, from about 1×10³ cells to about 3×10⁷ cells, from about 1×10³ cells to about 4×10⁷ cells, from about 1×10³ cells to about 5×10⁷ cells, from about 1×10³ cells to about 6×10⁷ cells, from about 1×10³ cells to about 7×10⁷ cells, from about 1×10³ cells to about 8×10⁷ cells, from about 1×10³ cells to about 9×10⁷ cells, from about 1×10³ cells to about 1×10⁸ cells, from about 1×10³ cells to about 2×10⁸ cells, from about 1×10³ cells to about 3×10⁸ cells, from about 1×10³ cells to about 4×10⁸ cells, from about 1×10³ cells to about 5×10⁸ cells, from about 1×10³ cells to about 6×10⁸ cells, from about 1×10³ cells to about 7×10⁸ cells, from about 1×10³ cells to about 8×10⁸ cells, from about 1×10³ cells to about 9×10⁸ cells, or from about 1×10³ cells to about 1×10⁹ cells.

In some cases, the therapeutically effective dose of a non-engineered, enriched γδ T-cell population, an engineered, enriched γδ T-cell population, and/or admixtures thereof, of the invention can be from about 1×10⁶ cells to about 2×10⁶ cells, from about 1×10⁶ cells to about 3×10⁶ cells, from about 1×10⁶ cells to about 4×10⁶ cells, from about 1×10⁶ cells to about 5×10⁶ cells, from about 1×10⁶ cells to about 6×10⁶ cells, from about 1×10⁶ cells to about 7×10⁶ cells, from about 1×10⁶ cells to about 8×10⁶ cells, from about 1×10⁶ cells to about 9×10⁶ cells, from about 1×10⁶ cells to about 1×10⁷ cells, from about 1×10⁶ cells to about 2×10⁷ cells, from about 1×10⁶ cells to about 3×10⁷ cells, from about 1×10⁶ cells to about 4×10⁷ cells, from about 1×10⁶ cells to about 5×10⁷ cells, from about 1×10⁶ cells to about 6×10⁷ cells, from about 1×10⁶ cells to about 7×10⁷ cells, from about 1×10⁶ cells to about 8×10⁷ cells, from about 1×10⁶ cells to about 9×10⁷ cells, from about 1×10⁶ cells to about 1×10⁸ cells, from about 1×10⁶ cells to about 2×10⁸ cells, from about 1×10⁶ cells to about 3×10⁸ cells, from about 1×10⁶ cells to about 4×10⁸ cells, from about 1×10⁶ cells to about 5×10⁸ cells, from about 1×10⁶ cells to about 6×10⁸ cells, from about 1×10⁶ cells to about 7×10⁸ cells, from about 1×10⁶ cells to about 8×10⁸ cells, from about 1×10⁶ cells to about 9×10⁸ cells, from about 1×10⁶ cells to about 1×10⁹ cells, from about 1×10⁶ cells to about 2×10⁹ cells, from about 1×10⁶ cells to about 3×10⁹ cells, from about 1×10⁶ cells to about 4×10⁹ cells, from about 1×10⁶ cells to about 5×10⁹ cells, from about 1×10⁶ cells to about 6×10⁹ cells, from about 1×10⁶ cells to about 7×10⁹ cells, from about 1×10⁶ cells to about 8×10⁹ cells, from about 1×10⁶ cells to about 9×10⁹ cells, from about 1×10⁷ cells to about 1×10⁹ cells, from about 1×10⁷ cells to about 2×10⁹ cells, from about 1×10⁷ cells to about 3×10⁹ cells, from about 1×10⁷ cells to about 4×10⁹ cells, from about 1×10⁷ cells to about 5×10⁹ cells, from about 1×10⁷ cells to about 6×10⁹ cells, from about 1×10⁷ cells to about 7×10⁹ cells, from about 1×10⁷ cells to about 8×10⁹ cells, from about 1×10⁷ cells to about 9×10⁹ cells, from about 1×10⁸ cells to about 1×10⁹ cells, from about 1×10⁸ cells to about 2×10⁹ cells, from about 1×10⁸ cells to about 3×10⁹ cells, from about 1×10⁸ cells to about 4×10⁹ cells, from about 1×10⁸ cells to about 5×10⁹ cells, from about 1×10⁸ cells to about 6×10⁹ cells, from about 1×10⁸ cells to about 7×10⁹ cells, from about 1×10⁸ cells to about 8×10⁹ cells, from about 1×10⁸ cells to about 9×10⁹ cells, or from about 1×10⁹ cells to about 1×10¹⁰ cells.

Preservation

In some embodiments, enriched γδ T cell populations, and/or admixtures thereof, may be formulated in freezing media and placed in cryogenic storage units such as liquid nitrogen freezers (−195° C.) or ultra-low temperature freezers (−65° C., −80° C. or −120° C.) for long-term storage of at least about 1 month, 2 months, 3 months, 4 months, 5 months, 6 months, 1 year, 2 years, 3 years, or at least 5 years. The freeze media can contain dimethyl sulfoxide (DMSO), and/or sodium chloride (NaCl), and/or dextrose, and/or dextran sulfate and/or hydroyethyl starch (HES) with physiological pH buffering agents to maintain pH between about 6.0 to about 6.5, about 6.5 to about 7.0, about 7.0 to about 7.5, about 7.5 to about 8.0 or about 6.5 to about 7.5. The cryopreserved γδ T cells can be thawed and further processed by stimulation with antibodies, proteins, peptides, and/or cytokines as described herein. The cryopreserved γδ T cells can be thawed and genetically modified with viral vectors (including retroviral and lentiviral vectors) or non-viral means (including RNA, DNA, and proteins) as described herein. Alternatively, non-engineered γδ T cells can be expanded by the methods described herein, genetically modified, and cryopreserved.

Thus, genetically engineered and/or non-engineered γδ T cells can be further cryopreserved to generate cell banks in quantities of at least about 1, 5, 10, 100, 150, 200, 500 vials at about at least $10^1$, $10^2$, $10^3$, $10^4$, $10^5$, $10^6$, $10^7$, $10^8$, $10^9$, or at least about $10^{10}$ cells per mL in freeze media. The cryopreserved cell banks may retain their functionality and can be thawed and further stimulated and expanded. In some aspects, thawed cells can be stimulated and expanded in suitable closed vessels such as cell culture bags and/or bioreactors to generate quantities of cells as allogeneic cell product. Cryopreserved γδ T cells can maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In some aspects, no preservatives are used in the formulation. The cryopreserved γδ T cells can be thawed and infused into multiple patients as allogeneic off-the-shelf cell product.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

The present invention is explained in more detail by the following non-limiting examples.

EXAMPLES

Example 1. Generation of Antibodies that Specifically Bind δ3 TCR

γδ TCR activators in the form of murine antibodies were produced by immunization of recombinant human soluble γ2 δ3TCR-FC, comprising the mature ECD of the γδ TCR chains fused to human IgG1FC. Three strains of mice (Balb/c, CD-1 and FVB) were inoculated with human recombinant γδ TCR to provide hybridomas secreting high affinity, murine monoclonal antibody activators.

The γδ TCR-Fc fusion construct was generated by PCR amplification. γ2δ3 TCR chains were amplified from RNA isolated from tumor infiltrating γδ lymphocytes extracted from a fresh specimen of malignant ovary cells from a metastasis to the omentum. Soluble δ3TCR-FC was purified from the supernatant of transiently transfected HEK 293 cells. 10 µg of soluble TCR was emulsified with an equal volume of TITERMAX® Gold (Sigma Aldrich) or Imject Alum Adjuvant (Thermo Fisher) and used for the immunization of each mouse. The resulting emulsions were then injected into three mice (1 each: Balb/c, CD-1 and FVB) via the footpad route.

Solid-phase ELISA assays were used to screen mouse sera for mouse IgG antibodies specific for human γδ3 TCR. Briefly, 96 well plates (VWR International, Cat. #610744) were coated with recombinant γδ3 TCR-at 1 µg/ml in ELISA coating buffer overnight. After washing with PBS containing 0.02% (v/v) Tween 20, the wells were blocked with 3% (w/v) BSA in PBS, 200 µL/well for 1 hour at room temperature (RT). Mouse serum was titrated (1:100, 1:200, 1:400, and 1:800) and added to the γδ TCR coated plates at 50 UL/well and incubated at RT for 1 hour. The plates are washed and then incubated with 50 µL/well HRP-labeled goat anti-mouse IgG diluted 1:10,000 in 3% BSA-PBS or 2% FCS in PBS for 1 hour at RT. Again the plates were washed and 40 µL/well of a TMB substrate solution (Thermo Scientific 34028) was added for 15 minutes at RT. After developing, an equal volume of 2N $H_2SO_4$ was added to stop substrate development and the plates were analyzed by spectrophotometer at OD 450.

Sera-positive immunized mice were sacrificed and draining lymph nodes (popliteal and inguinal) were dissected out and used as a source for antibody producing cells. A single cell suspension of B cells ($766 \times 10^6$ cells) was fused with non-secreting P3x63Ag8.653 myeloma cells (ATCC #CRL-1580) at a ratio of 1:1 by electrofusion. Electrofusion was performed using the BTX Hybrimmune™ System, (BTX Harvard Apparatus) as per the manufacturer's directions. After the fusion, the cells were resuspended in hybridoma selection medium supplemented with Azaserine (Sigma #A9666), high glucose DMEM medium with sodium pyruvate (Cellgro cat #15-017-CM) containing 15% Fetal Clone I serum (Hyclone), 10% BM Condimed (Roche Applied Sciences), 4 mM L-glutamine, 100 IU Penicillin-Streptomycin and 50 µM 2-mercaptoethanol and then plated in three T150 flasks in 50 mL selection medium per flask. The flasks were then placed in a humidified 37° C. incubator containing 5% $CO_2$ and 95% air for 6-7 days.

After six days of growth the library consisting of the cells grown in bulk in the T150 flask was plated at 1 cell per well in Falcon 384 well flat-bottom plates using the Aria II cell sorter. The selected hybridomas were then grown in 90 µL of culture medium containing 15% Fetal Clone I serum (Hyclone), 10% BM-Condimed (Roche Applied Sciences), 1 mM sodium pyruvate, 4 mM L-glutamine, 100 IU Penicillin-Streptamycin, 50 µM 2-mercaptoethanol, and 100 µM hypoxanthine. Any remaining unused hybridoma library cells were frozen for future library testing. After ten days of growth supernatants from each well of the plated cells were assayed for antibodies reactive for δ3 TCR by ELISA.

High bond ELISA 96 well plates were coated with soluble γδ TCR proteins generated by paring the following γδ TCR chains: γ8δ1, γ2δ1, and γ2δ3. Soluble TCRs were diluted and used at 1 µg/ml in sodium carbonate buffer overnight at 4° C. The plates were washed and blocked with 3% BSA in PBS/Tween for one hour at 37° C. and used immediately or kept at 4° C. Undiluted hybridoma supernatants were incubated on the plates for one hour at RT. The plates were washed and probed with HRP labeled goat anti-mouse IgG diluted 1:10,000 in 3% BSA-PBS for one hour at RT. The plates were then incubated with substrate solution as described above and read at OD 450. Wells containing immunoglobulin that preferentially bound human δ3 TCR chain as determined by a signal above background, were transferred and expanded.

The resulting δ3TCR specific clonal hybridomas were cryopreserved in CS-10 freezing medium (Biolife Solutions) and stored in liquid nitrogen Example 2. Sequencing of Murine Antibodies that Specifically Bind δ3 TCR Based on ELISA binding assays a number of exemplary distinct monoclonal antibodies that specifically bind to δ3 soluble TCR were selected for sequencing and further analysis. As shown in a tabular fashion in FIG. 1, sequence analysis of the light chain variable regions (FIG.) and heavy chain variable regions (FIG.) of selected monoclonal antibodies generated in Example 1 confirmed novel complementarity determining regions and display of novel VDJ arrangements. The complementarity determining regions set forth in FIG. 1 as defined by Kabat.

Total RNA was extracted from selected hybridoma cells using the RNeasy isolation kit (RNeasy Mini Kit Qiagen #74106). $10^4$ hybridoma cells were lysed in 350 µl RLT Buffer, an equal volume of 70% ethanol was added, and the sample was loaded to RNeasy Mini spin column. Column was washed twice and RNA was eluted by 100 µl of RNase-free water loaded directly to the spin column membrane. The quality of the RNA preparations was determined by fractionating 3 µL in a 1% agarose gel before being stored at −80° C. until used.

The variable region of the Ig heavy chain of each hybridoma was amplified using a 5' primer mix comprising thirty-two mouse specific leader sequence primers, designed to target the complete mouse VH repertoire, in combination with a 3' mouse Cγ primer specific for all mouse Ig isotypes. A 400 bp PCR fragment of the VH was sequenced from both ends using the same PCR primers. Similarly, a mix of thirty-two 5' Vκ leader sequence primers designed to amplify each of the Vκ mouse families combined with a single reverse primer specific to the mouse kappa constant region were used to amplify and sequence the kappa light chain. The VH and VL transcripts were amplified from 100 ng total RNA using reverse transcriptase polymerase chain reaction (RT-PCR).

A total of eight RT-PCR reactions were run for each hybridoma: four for the Vκ light chain and four for the Vγ heavy chain. The One Step OneStep Ahead RT-PCR kit was used for amplification (Qiagen #220213). This kit provides a blend of Sensiscript and Omniscript Reverse Transcriptases, QuantiNova HotStarTaq DNA Polymerase, dNTP mix, buffer and Q-Solution, a novel additive that enables efficient amplification of any RNA template. Reaction mixtures were prepared that included 5 µL of RNA, 0.5 of 100 µM of either heavy chain or kappa light chain primers (custom synthesized by IDT), 12.5 µL of master mix with DNA polymerases, buffer, dNTPs, 1 µL of enzyme mix containing reverse transcriptase and DNA polymerase, and 0.4 µL of ribonuclease inhibitor RNasin (1 unit). The reaction mixture contains all of the reagents required for both reverse transcription and PCR. The thermal cycler program was set for an RT step 50° C. for 10 minutes, 95° C. for 5 minutes, followed by 30 cycles of PCR (95° C. for 30 seconds, 58° C. for 30 seconds, 72° C. for one minute). There was then a final incubation at 72° C. for 10 minutes.

To prepare the PCR products for direct DNA sequencing, they were purified using the QIAquick™ PCR Purification Kit (Qiagen) according to the manufacturer's protocol. The DNA was eluted from the spin column using 50 µL of sterile water and then sequenced directly from both strands. The extracted PCR products were directly sequenced using specific V region primers. Nucleotide sequences were analyzed using VBase2 to identify germline V. D and J gene members with the highest sequence homology.

Annotated sequences are set forth in FIG. 1. More specifically, FIG. 1 (top) depicts the contiguous amino acid sequences of 7 novel murine heavy chain variable regions from δ3 TCR specific antibodies, and FIG. 1 (bottom) depicts the contiguous amino acid sequences of the corresponding light chain variable regions from the δ3 TCR specific antibodies Taken together FIG. 1 provides the annotated sequences of seven murine anti δ3 TCR antibodies (termed δ3-08, δ3-20, δ3-23, δ3-31, δ3-42, δ3-47 and δ3-58).

Example 3. γδ T Cell Expansion with δ3-Specific Antibodies 24-well plates (Corning) were coated with 300 µL of goat anti-mouse IgG antibodies at 5 g/mL overnight. The next day wells were washed once with PBS and blocked with 5% FBS in PBS for 1 h at 37° C. Vδ3 antibodies were prepared at 1 µg/mL in PBS containing 2% FBS. 300 µL of antibody solution was dispensed into each well and incubated for 2 h at room temperature for capture.

Figure 4A:
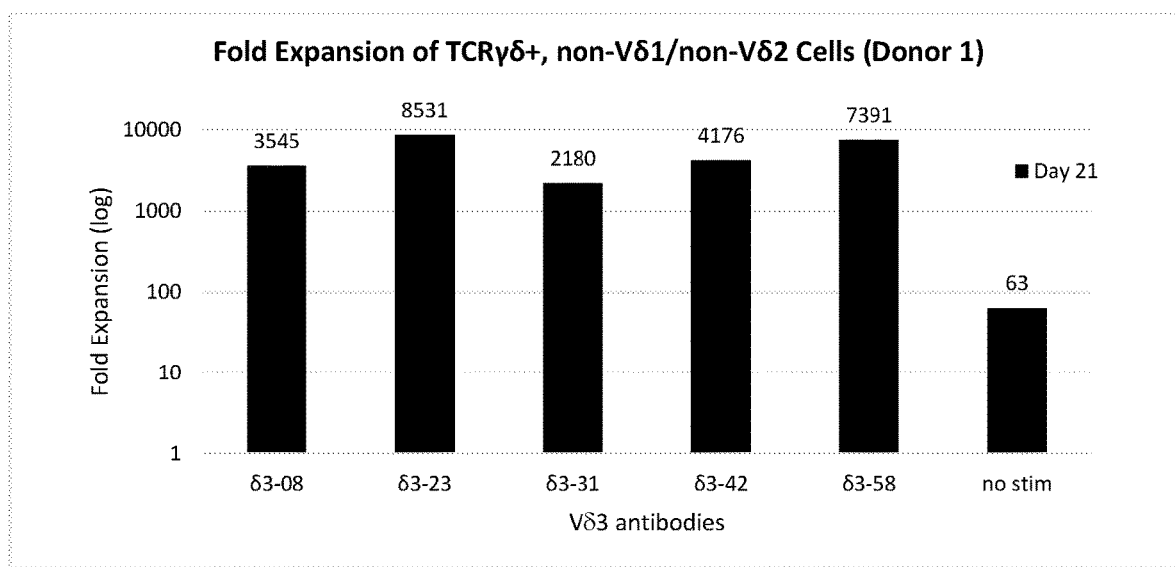
FIGS. 4A-B illustrate selective expansion of Vδ3 γδ T cells using a 21-day expansion culture protocol. Fold-expansion is measured on Day 21. A) PBMCs are isolated from Donor 1 and directly activated and expanded using the indicated antibody. B) PBMCs are isolated from Donor 2 and directly activated and expanded using the indicated antibody.
Figure 4B:
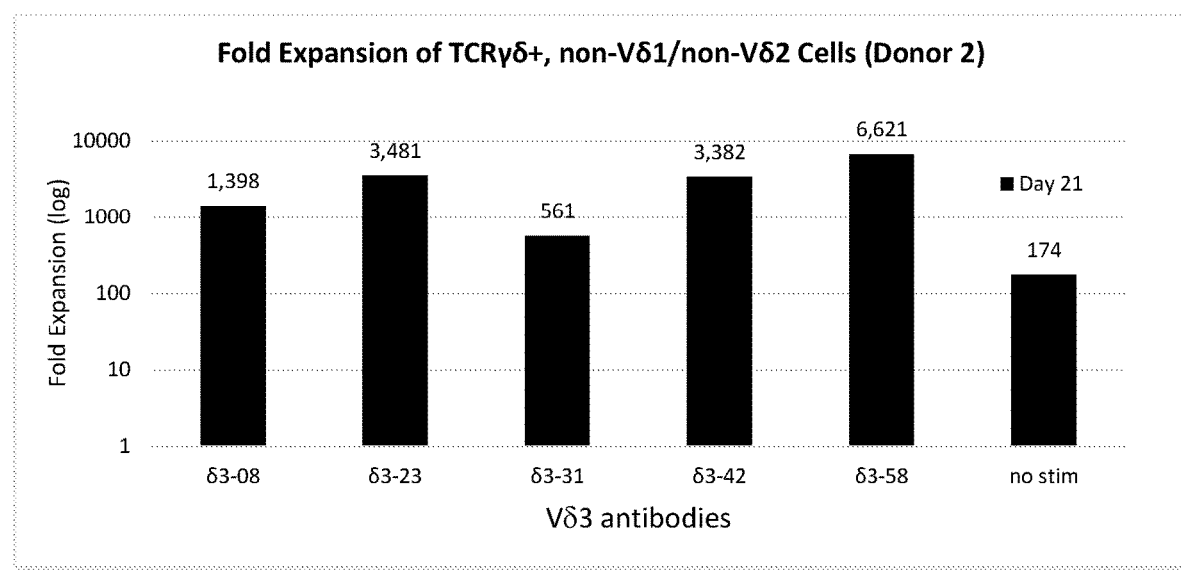

Human PBMCs from healthy individuals were plated into wells with captured Vδ3 antibodies at 1×10$^6$/mL/well in RPMI-1640 media containing 10% FBS, 2 mM Glutamine, 100 IU/mL of rhIL-2 and supplemented with antibiotics. Cells in culture were fed every 2-3 days by media replenishment. On Day 7 cells were harvested and re-plated at 1×10$^6$/mL into new plates without activating antibodies and further expanded by feeding every 2-3 days. Cells were re-plated on Day 14 to 1×10$^6$/mL cell density. Cell analysis (counts and flow cytometry) was performed on Day 21 to determine purity and fold expansion of non-Vδ1 (as determined with R9 Vd1 specific antibody, Beckman-Coulter) and non-Vδ2 (as determined with B6 Vd2 specific antibody, BioLegend) cells. FIG. 4A-B shows fold expansion of non-Vδ1/non-Vδ2 cells in PBMC cultures of two donors. Vδ3 specific antibodies induced expansion of up to 8531 fold (donor 1) and up 6621 fold (donor 2) depending on Vδ3 antibody.

Figure 5A:
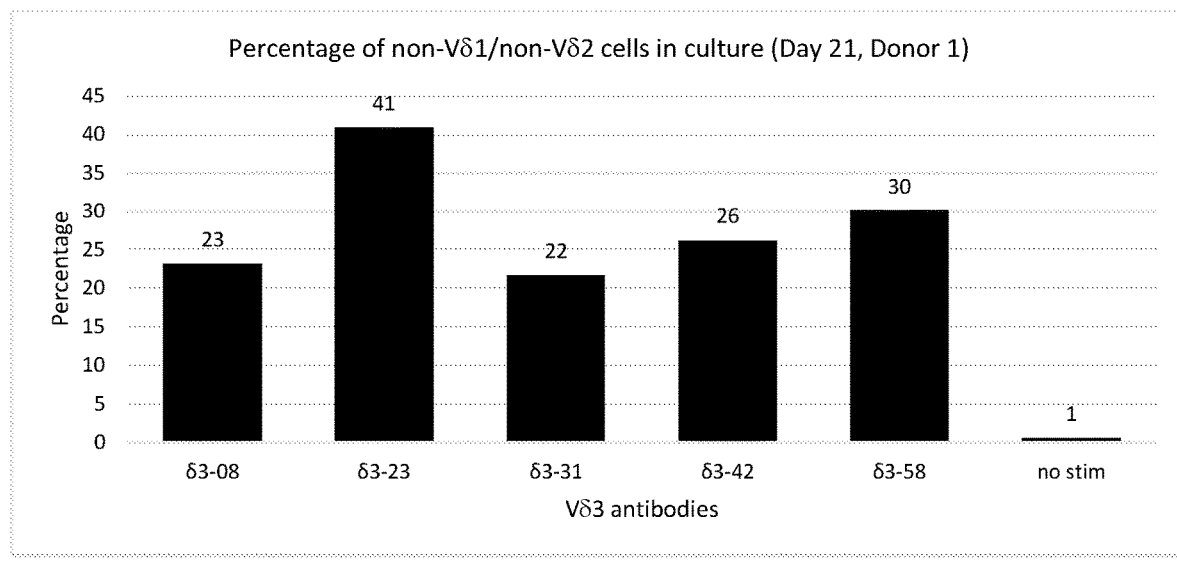
FIGS. 5A-B illustrates the proportion of Vδ1⁻/Vδ2⁻ γδ T cells in the expanded cell population illustrated in FIGS. 4A-B.
Figure 5B:
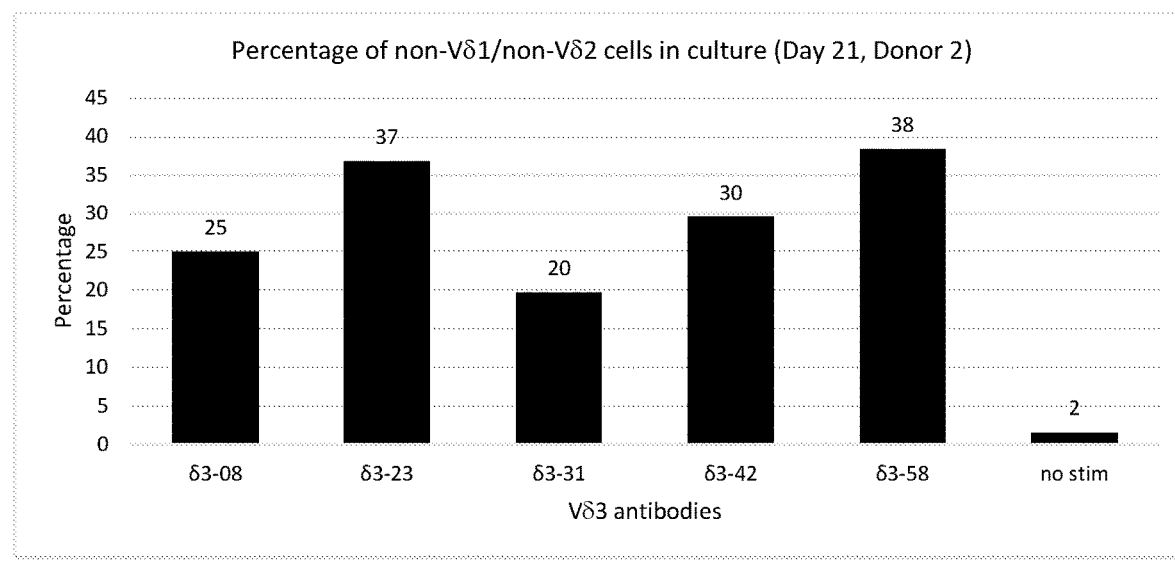

Purity of non-Vδ1/non-Vδ2 cells in the expanded cultures on Day 21 is shown in FIG. 5A-B for the two donors. Up to 41% of the cell culture on Day 21 was comprised of non-Vδ1/non-Vδ2 γδ T cells for Donor 1 PBMCs expanded with the δ3-23 antibody.

Figure 6A:
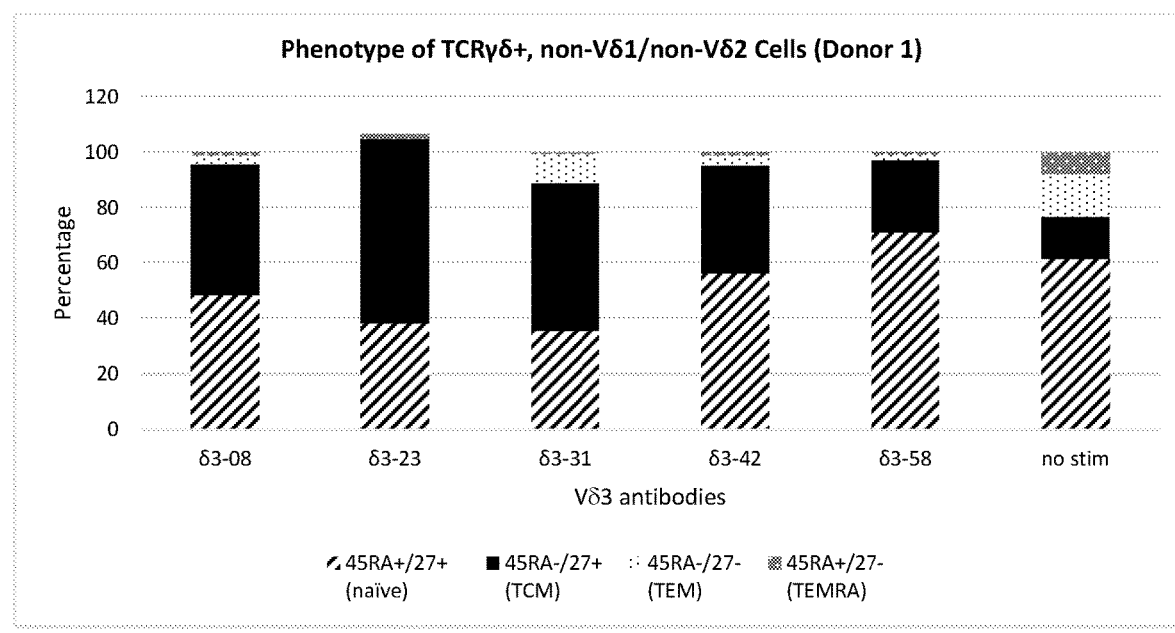
FIGS. 6A-B illustrates the phenotype of the γδ T cells in the expanded cell population illustrated in FIGS. 4A-B. The phenotype of Vδ3 T-cells activated and expanded with the indicated antibodies after 21 days of expansion culture is predominantly (>50%) CD27+CD45RA+ (naïve) and CD27+CD45RA− (central memory).
Figure 6B:
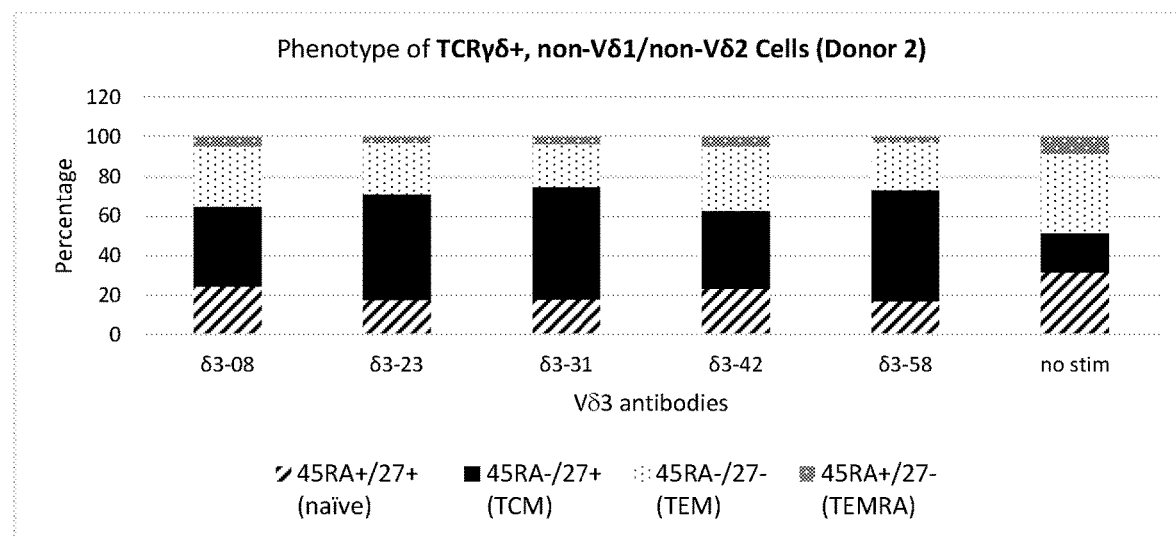

Phenotype of expanded δ1$^-$/δ2$^-$ T cells on Day 21 was evaluated by CD27 and CD45 surface marker expression. FIG. 6A-B shows that phenotype of δ1$^-$/δ2$^-$ T-cells activated with of MAbs on Day 21 is predominantly (>50%) CD27+CD45RA+ (naïve) and CD27+CD45RA− (central memory).

Example 4. Epitope Grouping of Vδ3 Antibodies by Competition Binding to γ2 δ3TCR-hFc Selected Vδ3 antibodies were grouped into epitope bins based on paired competition patterns using ForteBio Octet instrument and anti-human Fc AHC biosensors (ForteBio, Pall Corporation, Fremont, CA). Briefly, γ2 δ3TCR-hFc recombinant protein and all Vδ3 antibodies were diluted to 5 µg/mL in HBS-PB buffer (10 mM HEPES, 150 mM NaCl, 0.005% Tween-20, pH 7.4) containing 20 µg/mL of BSA. All samples (300 µl) were arranged in the 96-well plate and competition experiment was performed using Octet 384 instrument as per manufacturer's suggestion. First, the γ2 δ3TCR-hFc was captured on anti-human Fc biosensors for 5 minutes. Then, pairs of Vδ3 antibodies were allowed to bind to γ2 δ3TCR-hFc to saturation in succession (10 min each association phase) to determine if pairs of antibodies compete for binding sites on γ2 δ3TCR-hFc. If the second antibody did not bind, the two antibodies were considered to be in the same epitope bin and recognize the same, very similar, or largely overlapping, epitopes. ForteBio HT9.0 data analysis tool was applied to determine competition between Vδ3 antibodies.

The competition pattern of five anti-Vδ3 antibodies is presented in FIG. 7. The tested anti-Vδ3 antibodies were grouped into 3 epitope bins. δ3-23, δ3-42 and δ3-58 were all found to compete with each other in a paired binding assay and constitute one epitope bin designated 1A. δ3-31 did not compete with any of the antibodies tested that placed it into a separate Bin 2. δ3-08 antibody, did not compete with δ3-31 antibody, but appeared to be displaced by δ3-23, δ3-42 and δ3-58, suggesting that δ3-08 antibody likely has an overlapping epitope but δ3-08 affinity may be lower. Epitope of δ3-08 is designated Bin 1B.

Example 5. Activation, Transduction, and Selective Expansion of Vδ3 γδ T cells 12-well plates (Corning, CellBIND®) were directly coated overnight with purified δ3-08 or δ3-23 antibodies at 1 µg/mL in PBS at 600 µL/well, 4° C. The next day wells were washed with PBS and PBMCs (2×10$^6$ total cells) from two donors (Donor 3 and Donor 4) were added for activation at 1×10$^6$ cells/mL in RPMI-1640 media supplemented with 10% FBS, 2 mM Glutamine, 100 IU/mL of rhIL-2 (Pepro-tech). Starting PBMCs were characterized by flow cytometry for the content of Vδ1, Vδ2, and the non-Vδ1/Vδ2 γδ T (DN, double negative) fraction containing the Vδ3 cells. The non-Vδ1/Vδ2 γδ T cells content was <0.5% of total cells. Cell cultures were fed with fresh media supplemented with rhIL-2 by demi-exchange on day 2 and day 4.

On day 5, cells were washed in HBSS and transduced with retroviral construct encoding an anti-CD20 (Rituxan) chimeric antigen receptor ACT2 (scFv linked to CD28 transmembrane, co-stimulatory domains and CD3ζ). Briefly, wells of 12-well non-tissue culture treated plates were pre-coated with Retronectin® (TaKaRa Bio) at 10 µg/mL and 2×10$^6$ activated PBMCs were added to the wells (per donor, per activating antibody) followed by appropriate volume of viral supernatant to achieve MOI=1. Total volume of media was brought to 2 mL to achieve a cell concentration of 1×10$^6$ cells/mL and rhIL-2 was supplemented to 100 IU/mL. A portion of cells were not transduced but had undergone the same manipulation as CAR transduced cells (untransduced, mock transduction).

Figure 8A:
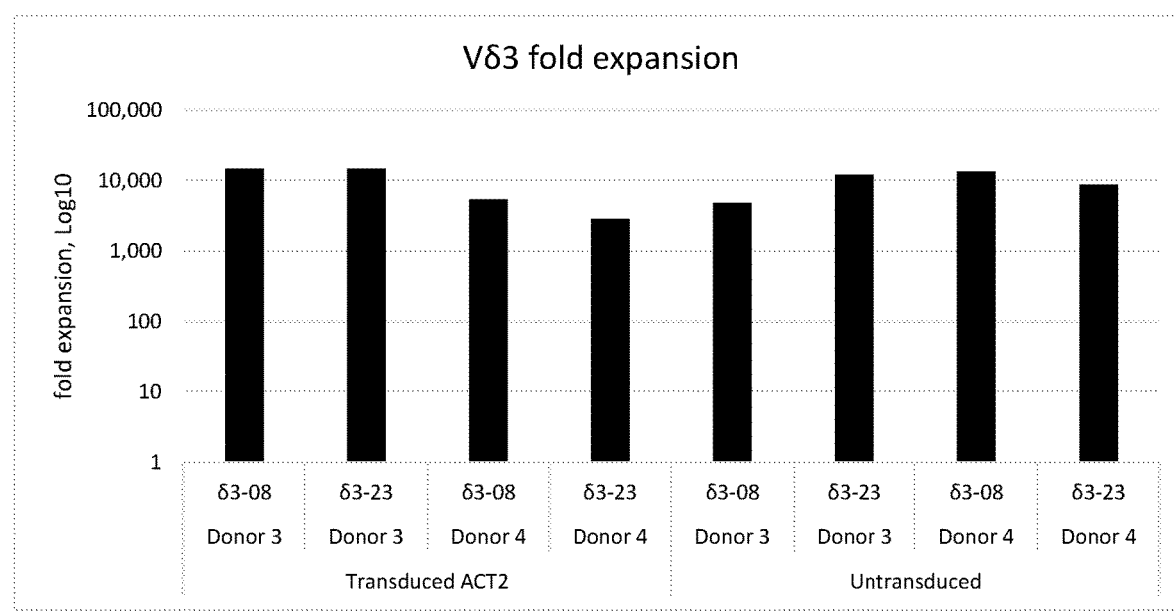
FIGS. 8A-C illustrate selective expansion of Vδ3 γδ T cells. A) Untransduced and anti-CD20 CAR Vδ3 γδ T cells are expanded approximately 10,000-fold. Vδ3 γδ T cells are detected as δ1-, δ2-, and δ3+ using antibodies specific for the δ1, δ2, and δ3 sub-types respectively. B) Before αβ T cell depletion, Vδ3 γδ T cells represent a major fraction of the expanded cell culture. C) anti-CD20 CAR construct is expressed on the surface of expanded and transduced Vδ3 γδ T cells.
Figure 8B:
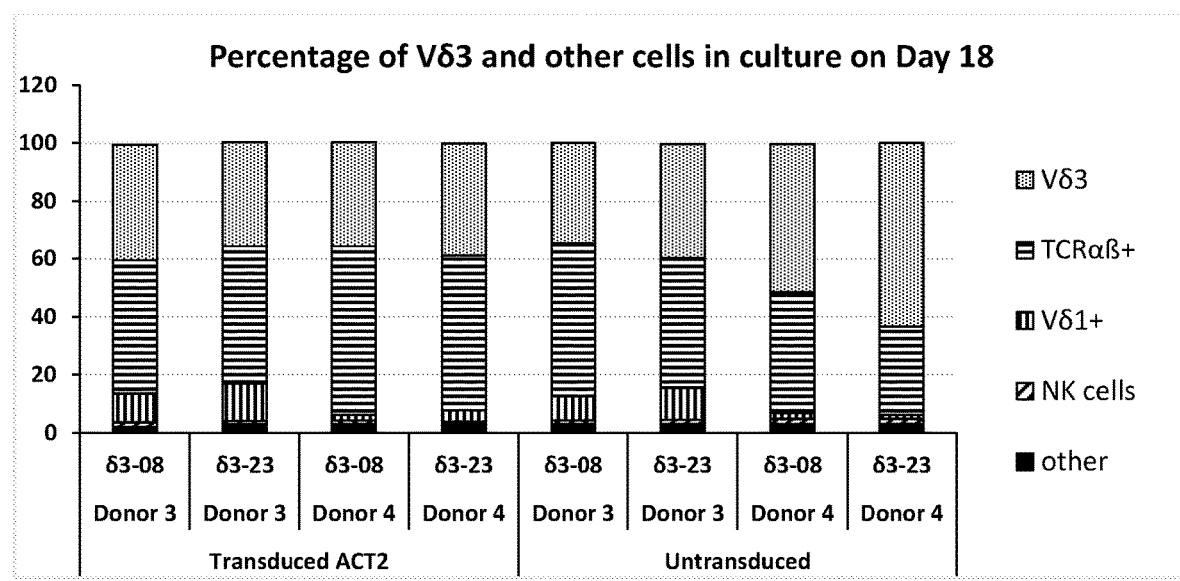
Figure 8C:
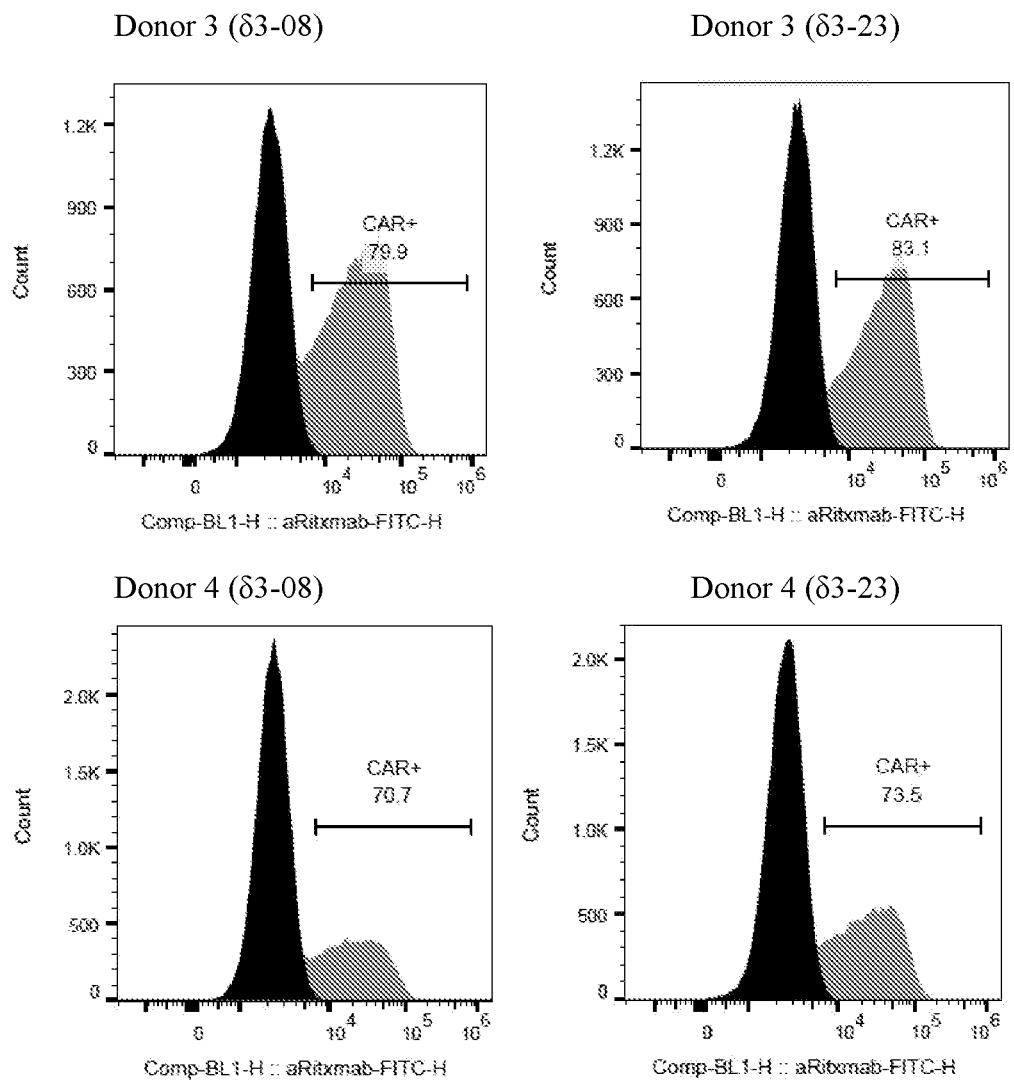
Figure 9:
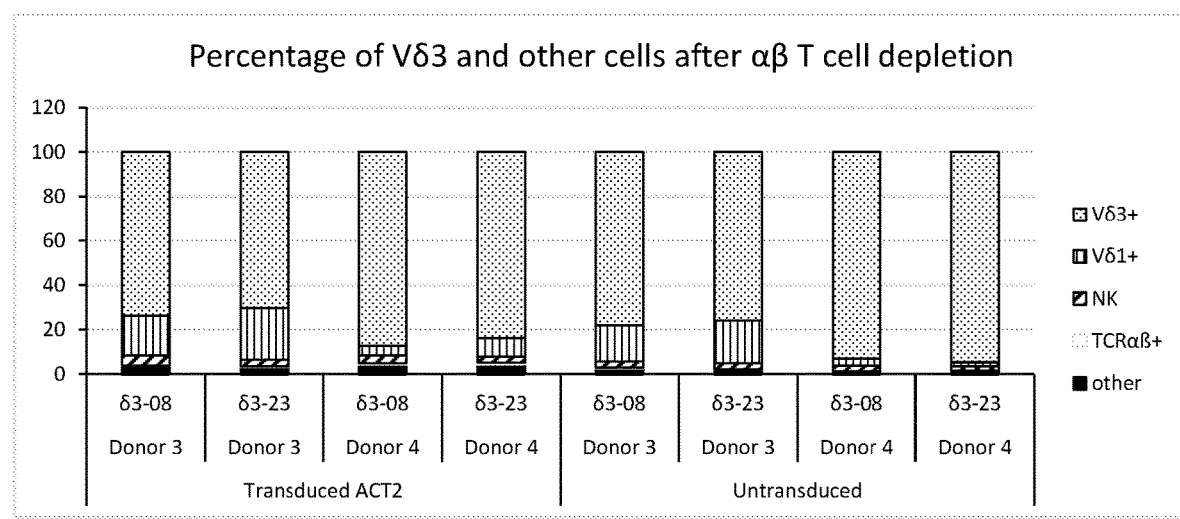
FIG. 9 illustrates successful depletion of αβ T cells from culture of activated expanded Vδ3 γδ T cells (left cells are transduced with anti-CD20 CAR construct; right cells are untransduced).

The next day cells were transferred to a 6-well plate for expansion and maintained for additional 11 days by feeding every other day by media demi-exchange. At the end of the expansion, cells were harvested, washed and analyzed by flow cytometry for Vδ3 fold expansion, purity, and CAR expression (FIG. 8 A-C). Briefly, cells were stained with antibodies to TCRαβ (Clone IP26), anti-TCRγδ (Immuno510, Beckman Coulter), anti-Vδ2 (B6, Biolegend), anti-Vδ1 (R9.12, Beckman Coulter), anti-CD16 and anti-CD56 (both BioLegend) and analyzed on BD FACS Canto II. To determine anti-CD20 CAR transduction efficiency, cells were stained with rat anti-Rituximab-FITC conjugate (BioRad, FIG. 8C). Data were analyzed using FlowJo software. αβ T cells in the culture were depleted using αβ T cell depletion kit (Miltenyi Biotec) using a manual procedure with LS columns. Purity and CAR expression after αβ T cell depletion were confirmed by flow cytometry and cells were used for cytotoxicity assay. The percentage of residual αβ T cells was <1% in all samples; and, the purity of Vδ3 cells was >70% depending on donor and antibody used for Vδ3 cell expansion (FIG. 9).

Figure 10:
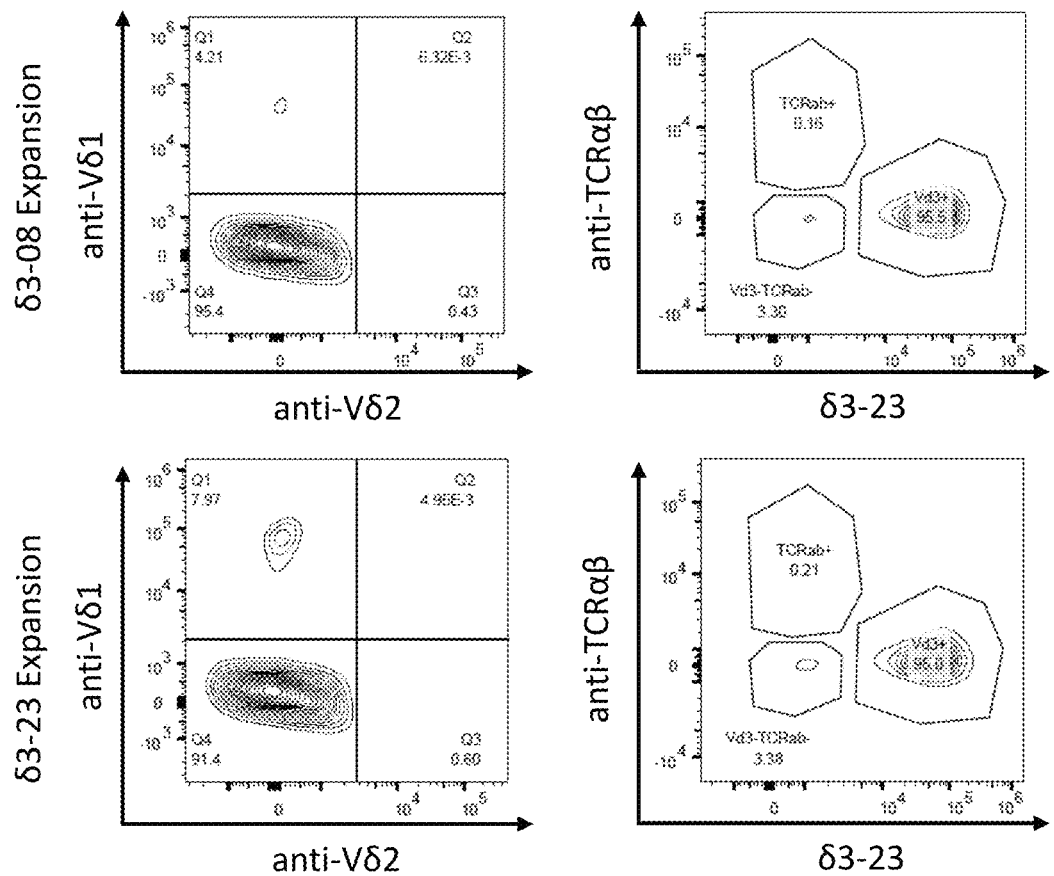
FIG. 10 illustrates results from staining an activated, expanded, and αβ T cell depleted population of γδ T cells to detect surface expression of Vδ1 and Vδ2 (left panels) or Vδ3 (right panels).

Untransduced cells from Donor 4 expanded using both δ3-08 and δ3-23 MAbs were depleted of residual αβ T cells and stained with δ3-23 MAb as well as other T cell markers (TCRαβ, anti-Vδ1, anti-Vδ2). As shown in FIG. 10, majority of cells after αβ T cell depletion (90%) are non-Vδ1/non-Vδ2 cells (left panels), of which>95% are stained positive for V δ 3 with δ3-23 MAb (right panels).

Example 6. Cytotoxicity Assay with Engineered Vδ3 γδ T Cells

Human PBMCs from Donor 3 were activated and transduced with CD20 CAR construct using δ3-08 and δ3-23 MAbs as described in Example 5. As described in Example 5, at the end of the expansion, cells were characterized for purity and transduction efficiency, and depleted of αβ T cells. The αβ T cell depleted cultures were then used in cytotoxicity assays against CD20+ Raji-NucLight Red cells. CD20+ Raji-NucLight Red cells have been transduced with IncuCyte® NucLight Red lentiviral particles allowing fluorescent detection of Raji cells on IncuCyte® platform.

Figure 11:
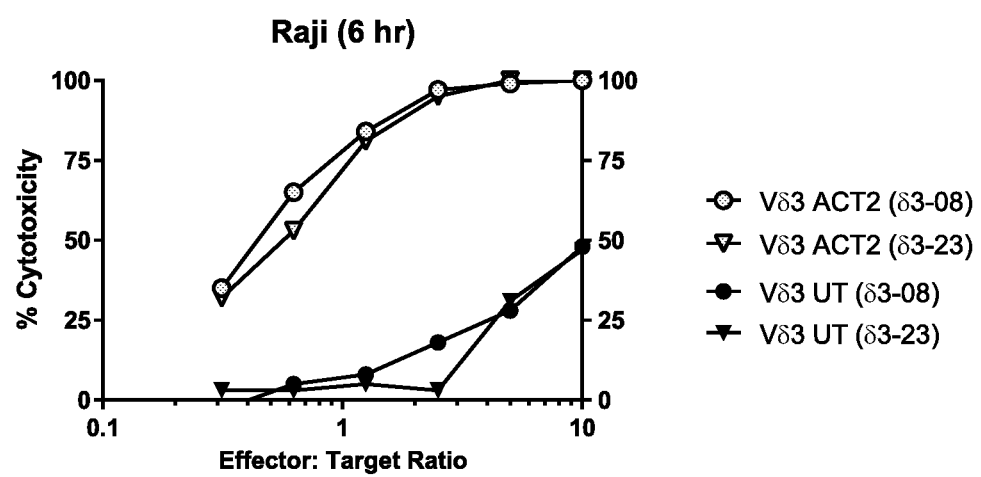
FIG. 11 illustrates cytotoxicity of activated and expanded Vδ3 γδ T cells against CD20+ Raji cells. Untransduced Vδ3 γδ T cells exhibited slight cytotoxicity against the CD20+ Raji cells at Effector:Target (E/T) ratios>1 and moderate cytotoxic activity at E/T ratios>5. Anti-CD20 CAR transduced Vδ3 γδ T cells exhibited moderate cytotoxic activity at an E/T ratio of 0.5 and strong cytotoxic activity at E/T ratios>0.75.

CD20 CAR-transduced or untransduced Vδ3 cells were co-incubated with Raji-NucLight Red cells at various E/T ratios for 6 hours in 384 well plates in RPMI-1640 media supplemented with 10% FBS, 2 mM Glutamine. Raji-NucLight Red cell viability was assessed as total fluorescence quantified from the entire well at 6 hour time point. As shown in FIG. 11, both anti-CD20 CAR transduced and untransduced Vδ3 cells expanded from Donor 3 using δ3-08 (A) or δ3-23 (B) MAbs exhibited cytotoxicity against CD20+ Raji-NucLight Red cells. Transduced Vδ3 cells significantly augmented cytotoxicity against CD20+ Raji-NucLight Red cells as compared to untransduced expanded Vδ3 cells.

Example 7. Fine Epitope Mapping of anti-Vδ3 Antibodies by Mutagenesis

Figure 12:
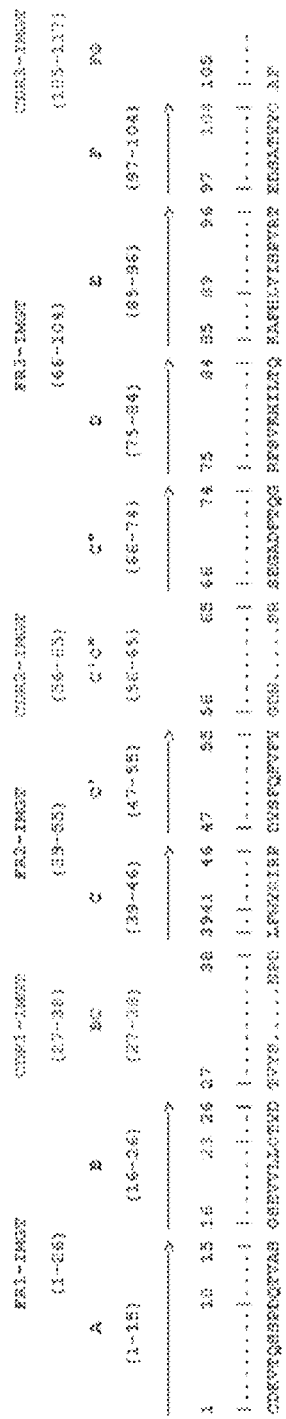
FIG. 12 discloses SEQ ID NO: 15 and illustrates an amino acid sequence of Vδ3, numbered according to IMGT nomenclature.

To determine amino acid residues in the variable Vδ3 region of the human γδTCR that are critical for binding of Vδ3 antibodies, several point mutations, or combination of thereof, were introduced into the δ3 chain and MAb binding was assessed using Luminex. Briefly, a computer model of Vδ3Vγ9 dimer molecule was created using crystal structures of Vδ2Vγ9 TCR deposited in PDB (Accession NOs 1HXM and 1TVD). Substitutions were introduced into the wild type sequence of the Vδ3 chain based on potential immunogenicity as shown in Table 1. Residue numbering of Vδ3 amino acids is as shown in FIG. 12. The mutated Vδ3 chains indicated in Table 1 were co-expressed with Vγ2 chain as human-Fc heterodimer fusion proteins in 293 Expi cells as described in Example 1 and purified using affinity chromatography on Protein A. Mutant and wt δ3γ2-hFc proteins were captured on Luminex® beads conjugated with goat-anti-human Fc polyclonal antibodies and $EC_{50}$ binding of various Vδ3 antibodies was determined. Loss or drop in $EC_{50}$ binding to a particular mutant δ3γ2-TCR fusion was monitored to determine contribution of the mutated amino acid to antigen binding. Without wishing to be bound by theory, it is hypothesized that the residues exhibiting a decrease in binding upon mutation are in contact with the δ3-specific antibody when bound to a Vδ3 γδ TCR.

TABLE 1

| Mutations in Vδ3 chain | Mutant Sequence ## | Vδ3 MAb ($EC_{50}$, nM) | | | | |
|---|---|---|---|---|---|---|
| | | δ3-08 | δ3-23 | δ3-31 | δ3-42 | δ3-58 |
| Wild type γ2δ3 | WT | 0.06 | 0.04 | 0.05 | 0.05 | 0.03 |
| D10N | S1 | 0.08 | 0.04 | 0.06 | 0.07 | 0.02 |
| D26N, K85L | S2 | 0.07 | 0.04 | 0.05 | 0.17 | 0.03 |
| K79L, H88F | S3 | 0.05 | 137.10* | 0.05 | 105.70* | 508.30* |
| E18Q | S4 | 0.06 | 0.06 | 0.05 | 0.05 | 0.02 |
| D70N, E67Q | S5 | 0.05 | 0.04 | 4.99 | 0.08 | 0.02 |
| R75Q, R95Q | S6 | 0.06 | 0.04 | 44.35* | 0.13 | 0.02 |
| D57N, R65Q | S7 | 0.07 | 0.04 | 0.05 | 0.15 | 0.04 |
| K79L, E18Q, H88F | S8 | 0.04 | 95.78* | 0.06 | 258.00* | 3366.00* |
| E67Q, D70N, R75Q, R95Q, E97Q | S9 | 0.07 | 0.05 | 37.66* | 49.29* | 0.05 |
| K3A, K79L, H88T | S10 | 2.50 | 117.00-* | 0.08 | 449.00-* | 336.00-* |
| K79L, L82K, H88F | S11 | 0.03 | 112.30-* | 0.06 | 198.70-* | 135.70-* |

*-extrapolated values; no saturation achieved

Close grouping of selected residues indicated to contribute to antigen binding by the fine epitope mapping described herein is illustrated in FIG. 13 and FIGS. 14A-C, suggesting that the δ3-specific epitopes recognized by the antibodies described herein can be at least partially, or entirely, conformational and/or non-linear. As indicated by FIG. 13, δ3-specific γδ TCR binding antibodies can bind an epitope that of Vδ3 that is distal from the γ-chain binding interface of Vδ3.

Figure 14A:
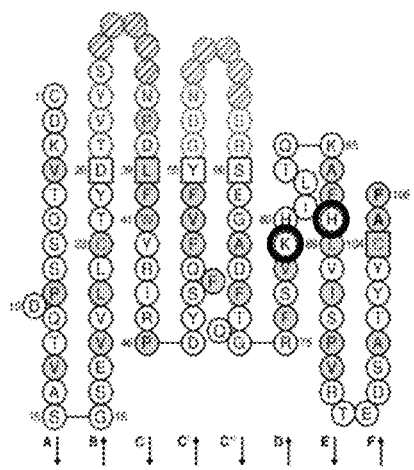
FIGS. 14A-C each disclose SEQ ID NO: 15 and illustrate IMGT Collier de Perles, with residues shown by fine epitope mapping to contribute to antigen binding highlighted by dark double circles. A) K79 and H88 contribute to antigen binding of δ3-23, δ3-42, and δ3-58. B) E67 and D70 contribute to antigen binding of δ3-31; R75 and R95 also contribute to antigen binding of δ3-31; the combination of E67, D70, R75, R95, and E97 contributes to antigen binding of δ3-31 and δ3-42. C) E18 contributes to antigen binding of δ3-58; and K3 contributes to antigen binding of δ3-08.
Figure 14B:
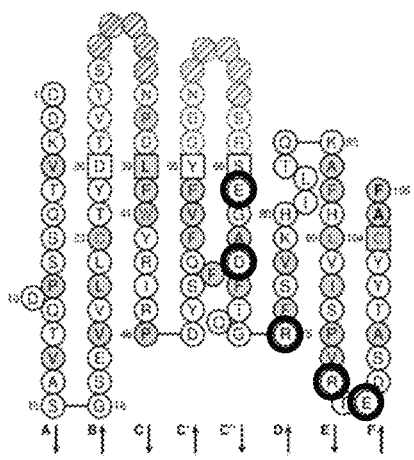
Figure 14C:
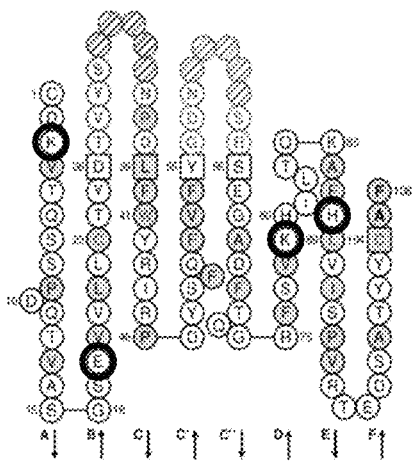

As shown in Table 1 and FIGS. 13-14C, the δ3-specific antibodies can be grouped into 2 major epitope binding groups, where δ3-08, δ3-23, δ3-42, and δ3-58 form the first group and δ3-31 forms the second group. The first major group can be separated into two sub-groups with δ3-23, δ3-42, and δ3-58 forming sub-group 1A and δ3-08 forming sub-group 1B. These results are in good agreement with the competition binding data illustrated in FIG. 7. However, in addition to highlighting specific residues involved in antigen binding, the fine mapping uncovers a third grouping formed by antibodies δ3-31 and δ3-42, which both show a reduction in binding to an E67Q, D70N, R75Q, R95Q, E97Q mutant Vδ3 γδ TCR.

FIGS. 14A-C also highlight β sheet strands D and E (IMGT nomenclature) as hot spots for antigen binding of δ3-specific antibodies. Thus, in some cases, δ3-specific antibodies can include those that bind a residue in β sheet strands D and E of Vδ3 (IMGT nomenclature); those that additionally or alternatively, bind a residue in β sheet strand C" and D and a residue in the loop between β strands E and F of Vδ3 of Vδ3 (IMGT nomenclature); and/or those that bind a residue in β sheet strand A, B, D, and E of Vδ3 (IMGT nomenclature).

At the amino acid level, it is hypothesized that some δ3 γδ TCR specific antibodies bind to residues K79 and H88 of Vδ3 (IMGT nomenclature). Additionally, or alternatively, some δ3 γδ TCR specific antibodies bind to residues R75 and R95 of Vδ3 (IMGT nomenclature). Additionally, or alternatively, some δ3 γδ TCR specific antibodies bind to residues K79, E18, and H88 of Vδ3 (IMGT nomenclature). Additionally, or alternatively, some δ3 γδ TCR specific antibodies bind to residues E67, D70, R75, R95, and E97 of Vδ3 (IMGT nomenclature). Additionally, or alternatively, some δ3 γδ TCR specific antibodies bind to residues K3, K79, and H88 of Vδ3 (IMGT nomenclature). Additionally, or alternatively, some δ3 γδ TCR specific antibodies bind to residues K79, L82, and H88 of Vδ3 (IMGT nomenclature).

What is claimed is:

1. An antibody or fragment thereof that binds an epitope specific to a δ3 γδ TCR, wherein the antibody or fragment thereof comprises:

(i) a heavy chain variable region/light chain variable region (HCVR/LCVR) sequence pair selected from the group consisting of SEQ ID NOs: 1/8, 2/9, 3/10, 4/11, 5/12, 6/13, and 7/14; or a HCVR/LCVR pair comprising (ii) the six complementarity determining regions (CDRs) of a HCVR/LCVR sequence pair selected from the group consisting of SEQ ID NOs: 1/8, 2/9, 3/10, 4/11, 5/12, 6/13, and 7/14.

2. The antibody or fragment thereof of claim 1, wherein the antibody or fragment thereof comprises:

a) the six CDRs of a HCVR/LCVR sequence pair selected from the group consisting of SEQ ID NOs: 1/8, 3/10, 4/11, 5/12, 6/13, and 7/14;

b) the six CDRs of a HCVR/LCVR sequence pair selected from the group consisting of SEQ ID NOs: 1/8, 3/10, 5/12, and 7/14;

c) the six CDRs of a HCVR/LCVR sequence pair selected from the group consisting of SEQ ID NOs: 3/10, 5/12, and 7/14;

d) the six CDRs of a HCVR/LCVR sequence pair selected from the group consisting of SEQ ID NOs: 4/11 and 5/12;

e) the six CDRs of a HCVR/LCVR sequence pair consisting of SEQ ID NOs: 1/8; or f) the six CDRs of a HCVR/LCVR sequence pair consisting of SEQ ID NOs: 4/11.

3. The antibody or fragment thereof of claim 1, wherein the antibody binds to:
  i) a region distal from the γ-chain binding interface of Vδ3;
  ii) β strand D and E of the Vδ3 of the γδ TCR according to IMGT nomenclature;
  iii) β strand C" and D and a loop between β strands E and F of the Vδ3 of the γδ TCR according to IMGT nomenclature; or
  iv) β strand A, B, D, and E of the Vδ3 of the γδ TCR according to IMGT nomenclature.

4. The antibody or fragment thereof of claim 2 or claim 3, wherein:
  (i) the antibody or fragment thereof selectively expands a δ3 γδ T cell as compared to αβ T cells in a mixed cell population comprising γδ T cells and αβ T cells;
  (ii) the antibody or fragment thereof is bound to a δ3 γδ TCR, optionally wherein the δ3 γδ TCR is expressed on the surface of a δ3 γδ T cell; or
  (iii) the antibody or fragment thereof is bound to an extracellular surface of an antigen presenting cell (APC), optionally wherein the antibody or fragment thereof is anchored in the membrane of the APC or wherein an Fc region of the antibody or fragment thereof is bound to an Fc-receptor expressed by the APC.

5. A nucleic acid encoding any one of the antibodies or fragments thereof according to claim 1, wherein the nucleic acid is operably linked to a heterologous promoter.

6. A host cell comprising any one of the antibodies or fragments thereof according to claim 1, or a nucleic acid according to claim 5; optionally wherein the host cell is an artificial antigen presenting cell (aAPC).

7. A method of making an antibody or fragment thereof that binds an epitope specific to a δ3 γδ TCR, the method comprising culturing the host cell of claim 6 under conditions sufficient to produce the antibody or fragment thereof.

8. An ex vivo method for producing an enriched γδ T cell population, comprising contacting a first cell population comprising γδ T cells with one or more antibodies or fragments thereof according to claim 1.

9. The method of claim 8, wherein:
  (i) the first cell population is an isolated mixed cell population comprising αβ T cells and γδ T cells, optionally wherein the first cell population comprises, or is, a sample of peripheral blood mononuclear cells (PBMCs) or wherein the first cell population is selected from a peripheral blood sample, a leukapheresis sample, a cord blood sample, a tumor sample, or a tissue sample;
  (ii) the first cell population comprises less than 1% δ3 γδ T cells;
  (iv) the first cell population comprises uncultured primary cells or unpassaged primary cells; and/or
  (v) the method comprises directly contacting the isolated mixed cell population with the one or more antibodies or fragments thereof.

10. The method of claim 8, wherein:
  (i) the first cell population comprises one or more engineered γδ T cells; and/or
  (ii) the first cell population comprises expanded γδ T cells, optionally wherein the method comprises a first γδ T cell expansion and a second γδ T cell expansion.

11. The method of claim 8, wherein:
  (i) the method comprises producing an enriched γδ T cell population comprising at least $10^8$ δ3 γδ T cells, optionally wherein the enriched γδ cell population comprising at least $10^8$ δ3 γδ T cells is produced within 12 to 21 days; and/or
  (ii) wherein the method comprises expanding the δ3 γδ T cells in the first cell population at least 1,000-fold, optionally wherein the specified-fold expansion is achieved within 12 to 21 days.

12. An ex vivo method for producing an enriched γδ T cell population, comprising:
  a) contacting a first cell population comprising γδ T cells with one or more first activating agents that activate and expand γδ T cells, thereby producing an expanded first γδ T cell population; and
  b) contacting the expanded first γδ T cell population with one or more second activating agents that activate and expand γδ T cells, thereby producing the enriched γδ T cell population,
wherein at least one of the one or more first activating agents or at least one of the one or more second activating agents is an antibody or fragment thereof according to claim 1.

13. The method of claim 12, wherein:
  (i) the method comprises isolating the expanded first γδ T cell population after a) and before b);
  (ii) a) comprises culturing the first cell population in the presence of an antigen presenting cell (APC) and the one or more first activating agents or b) comprises culturing the expanded first γδ T cell population in the presence of an antigen presenting cell (APC) and the one or more second activating agents;
  (iii) the first cell population is:
    (I) an isolated mixed cell population comprising αβ T cells and γδ T cells, optionally wherein the first cell population is selected from a peripheral blood sample, a leukapheresis sample, a cord blood sample, a tumor sample, or a tissue sample or wherein the first cell population comprises, or is, a sample of peripheral blood mononuclear cells (PBMCs); optionally wherein the first cell population comprises uncultured primary cells, unpassaged primary cells; or
    (II) a population of engineered γδ T cells;
  (iv) the method comprises genetically engineering the expanded first γδ T cell population or genetically engineering the enriched γδ T cell population;
  (v) the method comprises producing an enriched γδ T cell population comprising at least $10^8$ δ3 γδ T cells, optionally wherein the enriched γδ T cell population comprising at least $10^8$ δ3 γδ T cells is produced within 12 to 21 days;
  (vi) the method comprises expanding the δ3 γδ T cells in the first cell population at least 1,000-fold, optionally wherein the specified-fold expansion is achieved within 12 to 21 days;
  (vii) at least one of the one or more first activating agents is structurally identical to at least one of the one or more second activating agents;
  (viii) at least one of the one or more first activating agents is structurally different than at least one of the one or more second activating agents; and/or
  (ix) at least one of the one or more first activating agents or at least one of the one or more second activating agents is immobilized, optionally wherein the immobilized activating agent is immobilized on a surface of a culture vessel or on a surface of an antigen presenting cell (APC) or an artificial antigen presenting cell (aAPC); optionally wherein immobilized activating agent is the antibody or fragment thereof that binds the epitope specific to a δ3 γδ TCR.

14. A method according to claim 8, wherein the method achieves greater than 30% δ3 γδ T cells prior to, or in the absence of, αβ T cell depletion, preferably greater than 40%.

15. An enriched γδ T cell population, which is produced by a method according to claim 8 or 12, wherein greater than 30% of the γδ T cells are δ3 γδ T cells, preferably greater than 40%, more preferably greater than 60%, yet more preferably greater than 70%, even more preferably greater than 80% before positive or negative selection for δ3 γδ T cells; optionally wherein:
   (i) the γδ T cell population comprises polyclonal TCR diversity, optionally wherein greater than 60% or 70% the δ3 T-cells express the phenotype CD45RA+/CD27+ and/or CD45RA-/CD27+;
   (ii) the γδ T cell population is derived from tumor infiltrating lymphocytes;
   (iii) the γδ T-cells express an endogenous or heterologous tumor recognition moiety;
   (iv) the population comprises a therapeutically effective amount of γδ T-cells;
   (v) the γδ T cell population comprises anti-tumor cytotoxicity that is independent of NKp30 activity, NKp44 activity, and/or NKp46 activity, optionally wherein the γδ T cell population does not comprise NKp30 activity-dependent anti-tumor cytotoxicity, NKp44 activity-dependent anti-tumor cytotoxicity, and/or NKp46 activity-dependent anti-tumor cytotoxicity; and/or
   (vi) wherein less than 40% of the γδ T cells express a detectable level of NKp30, NKp44, and/or NKp46.

16. An enriched γδ T cell population, which is produced by a method according to claim 8 or 12, wherein the enriched γδ T cell population comprises from 20% to 50% δ3 γδ T cells before positive or negative selection for δ3 γδ T cells.

17. A method of treating cancer, an inflammatory disease, or an autoimmune disease in a subject in need thereof, the method comprising:
   a) providing a therapeutically effective amount of an enriched γδ T cell population according to claim 15 or claim 16; and
   b) administering the therapeutically effective amount of the enriched γδ T cell population to the subject.

18. The method according to claim 17, wherein the method further comprises admixing the enriched γδ T cell population with a second expanded γδ T cell population to form an admixed population and administering the admixed population to the subject; optionally wherein:
   (i) the second expanded γδ T cell population comprises>60% δ1 or>60% δ2 γδ T cells;
   (ii) the admixed γδ T cell population comprises>60% δ1 or>60% δ2 γδ T cells; or
   (iii) the admixed γδ T cell population comprises>60% δ3 γδ T cells.

19. The method of claim 8 or 12, further comprising genetically engineering the γδ T cells.

20. The method of claim 19, wherein the method comprises genetically engineering the enriched γδ T cell population.

21. The method of claim 19, wherein the γδ T cells are engineered to express one or more tumor recognition moieties.

22. The method according to 20 or 21, wherein:
   a) the engineered γδ T cells lack an HLA locus;
   b) the engineered γδ T cells are universal donor cells;
   c) the engineered γδ T cells are tumor-specific allogeneic γδ T cells; or
   d) the γδ T cells are engineered to express two or more tumor recognition moieties.

23. The method according to claim 22(d):
   i) wherein the two or more tumor recognition moieties are different, wherein each different tumor recognition moiety is engineered to recognize different epitopes of the same antigen; or
   ii) wherein the two or more tumor recognition moieties are different, wherein each different tumor recognition moiety is engineered to recognize different epitopes of different antigens.

24. The method according to claim 21, wherein:
   a) the tumor recognition moiety is derived from a tumor infiltrating lymphocyte;
   b) the tumor recognition moiety is cloned from a T-cell;
   c) the tumor recognition moiety is an engineered T-cell receptor;
   d) the tumor recognition moiety is an antibody, an antibody fragment, a scFv, a single domain antibody, or a Fab, that recognizes a tumor antigen; or
   e) the tumor antigen is a peptide-MHC complex, and the tumor recognition moiety recognizes the peptide-MHC complex.

25. The method according to claim 24(c), wherein:
   i) the engineered T-cell receptor is derived from a human or a mouse T-cell receptor;
   ii) the engineered T-cell receptor is an engineered αβ TCR; or
   iii) the engineered T-cell receptor is an engineered γδ TCR.

26. The method according to claim 20 or 21, wherein the γδ T cells are engineered to express an antigen recognition moiety, wherein the antigen recognition moiety recognizes an antigen associated with an autoimmune disease, or wherein the antigen recognition moiety recognizes a pathogenic antigen, wherein the pathogenic antigen is derived from a pathogenic bacterium or a virus.

27. The method of claim 8 or 12, further comprising depleting αβ T cells, B cells and/or NK cells in the enriched γδ T-cell population.

28. A composition comprising the enriched γδ T cell population of claim 16; and the at least one antibody or fragment thereof of claim 1.

* * * * *

SEQUENCE LISTING

```
<160> NUMBER OF SEQ ID NOS: 15

<210> SEQ ID NO 1
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Glu Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Ile Tyr
            20                  25                  30

Trp Met Asn Trp Val Arg Gln Ser Pro Glu Lys Gly Leu Glu Trp Val
        35                  40                  45

Gly Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Met Tyr Tyr Gly Ser Ser Tyr Glu Arg Phe Ala Tyr Trp Gly
            100                 105                 110

Gln Gly Thr Leu Val Thr Val Ser Ala
        115                 120

<210> SEQ ID NO 2
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Gln Gln Ser Gly Ala Glu Leu Val Arg Pro Gly Thr
1               5                   10                  15

Ser Val Lys Met Ser Cys Lys Ala Thr Gly Tyr Thr Phe Ser Asn Tyr
            20                  25                  30

Trp Thr Gly Trp Val Lys Gln Arg Pro Gly His Gly Leu Glu Arg Ile
```

```
                    35                  40                  45
Gly Asp Ile Tyr Pro Gly Gly Tyr Thr Asn Tyr Asn Glu Glu Phe
 50                  55                  60

Lys Gly Lys Ala Thr Leu Thr Ala Asp Thr Ser Ser Thr Val Tyr
 65                  70                  75                  80

Met Leu Leu Ser Ser Leu Thr Phe Glu Asp Ser Ala Ile Tyr Tyr Cys
                 85                  90                  95

Ala Arg Trp Gly Ser Asp Tyr Ala Met Asp Tyr Trp Gly Gln Gly Thr
             100                 105                 110

Ser Val Thr Val Ser Ser
         115

<210> SEQ ID NO 3
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Gln Gln Ser Gly Ala Glu Leu Val Lys Pro Gly Ala
  1               5                  10                  15

Ser Val Lys Leu Ser Cys Thr Ala Ser Gly Phe Asn Ile Arg Asp Thr
                 20                  25                  30

Tyr Met His Trp Val Lys Gln Arg Pro Glu Gln Gly Leu Glu Trp Ile
             35                  40                  45

Gly Arg Ile Asp Pro Ala Asn Gly Asn Thr Lys Tyr Asp Pro Lys Phe
 50                  55                  60

Arg Gly Lys Ala Thr Ile Thr Ala Asp Thr Ser Ser Asn Thr Ala Tyr
 65                  70                  75                  80

Leu Gln Leu Ser Ser Leu Thr Ser Glu Gly Thr Ala Val Tyr Tyr Cys
                 85                  90                  95

Ser Glu Gly Ile Tyr Phe Asp Tyr Trp Gly Gln Gly Thr Thr Leu Thr
             100                 105                 110

Val Ser Ser
         115

<210> SEQ ID NO 4
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ser Asp Val Gln Leu Gln Glu Ser Gly Pro Asp Leu Val Lys Pro Ser
  1               5                  10                  15

Gln Ser Leu Ser Leu Thr Cys Thr Val Thr Gly Tyr Ser Ile Thr Ser
                 20                  25                  30

Gly Tyr Gly Trp His Trp Ile Arg Gln Phe Pro Gly Asn Lys Leu Glu
             35                  40                  45

Trp Met Gly Tyr Ile Ser Phe Ser Gly Ser Asn Lys Tyr Asn Pro Ser
 50                  55                  60

Leu Lys Ser Arg Ile Ser Ile Thr Arg Asp Thr Ser Lys Asn Gln Phe
 65                  70                  75                  80
```

-continued

```
Phe Leu Gln Leu Asn Ser Val Thr Thr Glu Asp Thr Ala Thr Tyr Tyr
                85                  90                  95

Cys Ala Asn Leu Asp Tyr Trp Gly Gln Gly Thr Thr Leu Thr Val Ser
            100                 105                 110

Ser

<210> SEQ ID NO 5
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ser Asp Val Gln Leu Gln Glu Ser Gly Pro Asp Leu Val Lys Pro Ser
1               5                   10                  15

Gln Ser Leu Ser Leu Thr Cys Thr Val Thr Gly Tyr Ser Ile Thr Ser
            20                  25                  30

Gly Tyr Asn Trp His Trp Ile Arg Gln Phe Pro Gly Asn Lys Leu Glu
        35                  40                  45

Trp Met Gly Tyr Ile His Tyr Ser Gly Asn Thr Asp Tyr Asn Pro Ser
    50                  55                  60

Leu Arg Ser Arg Ile Ser Ile Thr Arg Asp Thr Ser Lys Asn Gln Phe
65                  70                  75                  80

Phe Leu His Leu Asn Ser Val Pro Thr Glu Asp Thr Ala Thr Tyr Tyr
                85                  90                  95

Cys Ala Arg Ser Gly Ile Thr Thr Asp Trp Tyr Phe Asp Val Trp Gly
            100                 105                 110

Ala Gly Thr Thr Val Thr Val Ser Ser
        115                 120

<210> SEQ ID NO 6
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met Asn Trp Val Lys Gln Arg Pro Glu Gln Gly Leu Asp Trp Ile
        35                  40                  45

Gly Gly Ile Asp Pro Ala Asn Gly Asn Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Phe Tyr Cys
                85                  90                  95

Ala Arg Tyr Arg Asp Tyr Ala Val Asp Tyr Trp Gly Gln Gly Trp Gly
            100                 105                 110

Gln Gly Thr Ser Val Thr Val Ser Ser
```

115                 120

<210> SEQ ID NO 7
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Tyr Ile Arg Asp Gly Gly Gly Thr Tyr Tyr Pro Asp Thr Val
    50                  55                  60

Glu Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Pro Pro Met Asn Asp Trp Phe Leu Tyr Trp Gly Gln Gly
            100                 105                 110

Thr Leu Val Thr Val Ser Ala
        115

<210> SEQ ID NO 8
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Ile Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Lys Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Trp Thr Phe Gly Gly Gly Thr Lys Leu Glu Ile Lys
            100                 105

<210> SEQ ID NO 9
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:

-continued

```
                Synthetic polypeptide"

<400> SEQUENCE: 9

Gln Ile Val Leu Thr Gln Ser Pro Ala Ile Met Ala Ser Pro Gly
1               5                   10                  15

Glu Lys Val Thr Met Thr Cys Ser Ala Ser Ser Val Ser Ser Arg
            20                  25                  30

Tyr Leu His Trp Tyr Gln Gln Lys Ser Gly Ala Ser Pro Lys Phe Trp
        35                  40                  45

Ile Tyr Gly Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr His Ser Asp Pro
                85                  90                  95

Pro Thr Phe Gly Gly Gly Thr Lys Leu Glu Ile Lys
            100                 105

<210> SEQ ID NO 10
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ile
            20                  25                  30

Ile His Trp Tyr Gln Gln Arg Ala Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Tyr
                85                  90                  95

Thr Phe Gly Gly Gly Thr Lys Leu Glu Ile Lys Arg
            100                 105

<210> SEQ ID NO 11
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Arg Thr Ser Ser Leu Ser Ala Ser Leu Gly
1               5                   10                  15

Asp Arg Val Thr Ile Ser Cys Ser Ala Ser Gln Asp Ile Thr Asn Tyr
            20                  25                  30

Leu His Trp Phe Gln Gln Lys Pro Asp Gly Thr Val Lys Leu Leu Ile
        35                  40                  45
```

```
Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Thr Arg
            100                 105
```

<210> SEQ ID NO 12
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Lys Val Glu Ala Glu
65                  70                  75                  80

Asp Ala Ala Thr Tyr Tyr Cys Gln Gln Trp Ser Ser His Gln Pro Thr
                85                  90                  95

Phe Gly Ala Gly Thr Lys Leu Glu Leu Lys
            100                 105
```

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Asp Ile Arg Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
                20                  25                  30

Leu Arg Trp Cys Gln Gln Lys Pro Gly Lys Ser Pro Lys Thr Leu Ile
            35                  40                  45

Tyr Gly Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105
```

```
<210> SEQ ID NO 14
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser His
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys Arg
            100                 105

<210> SEQ ID NO 15
<211> LENGTH: 96
<212> TYPE: PRT
<213> ORGANISM: Homo sapiens

<400> SEQUENCE: 15

Cys Asp Lys Val Thr Gln Ser Ser Pro Asp Gln Thr Val Ala Ser Gly
1               5                   10                  15

Ser Glu Val Val Leu Leu Cys Thr Tyr Asp Thr Val Tyr Ser Asn Pro
            20                  25                  30

Asp Leu Phe Trp Tyr Arg Ile Arg Pro Asp Tyr Ser Phe Gln Phe Val
        35                  40                  45

Phe Tyr Gly Asp Asn Ser Arg Ser Glu Gly Ala Asp Phe Thr Gln Gly
    50                  55                  60

Arg Phe Ser Val Lys His Ile Leu Thr Gln Lys Ala Phe His Leu Val
65                  70                  75                  80

Ile Ser Pro Val Arg Thr Glu Asp Ser Ala Thr Tyr Tyr Cys Ala Phe
                85                  90                  95
```